(12) United States Patent
Nagy et al.

(10) Patent No.: US 10,774,352 B2
(45) Date of Patent: Sep. 15, 2020

(54) ENZYMATIC PRODUCTION OF ALPHA-1,3-GLUCAN

(71) Applicant: DUPONT INDUSTRIAL BIOSCIENCES USA, LLC, Wilmington, DE (US)

(72) Inventors: Kevin D. Nagy, Wilmington, DE (US); Susan Marie Hennessey, Avondale, PA (US); Yefim Brun, Wilmington, DE (US); Michael Reichman, San Francisco, CA (US)

(73) Assignee: DUPONT INDUSTRIAL BIOSCIENCES USA, LLC, Wilmington, DE (US)

( * ) Notice: Subject to any disclaimer, the term of this patent is extended or adjusted under 35 U.S.C. 154(b) by 0 days.

(21) Appl. No.: 15/985,831

(22) Filed: May 22, 2018

(65) Prior Publication Data
US 2018/0340199 A1 Nov. 29, 2018

Related U.S. Application Data

(60) Provisional application No. 62/509,915, filed on May 23, 2017, provisional application No. 62/519,217, filed on Jun. 14, 2017.

(51) Int. Cl.
*C12P 19/04* (2006.01)
*C12N 9/10* (2006.01)
(Continued)

(52) U.S. Cl.
CPC .......... *C12P 19/04* (2013.01); *C08B 37/0009* (2013.01); *C08B 37/0021* (2013.01);
(Continued)

(58) Field of Classification Search
None
See application file for complete search history.

(56) References Cited

U.S. PATENT DOCUMENTS 5,952,205 A 9/1999 Catani et al.
6,242,225 B1 6/2001 Catani et al.
(Continued)

FOREIGN PATENT DOCUMENTS

EP 2292803 B1 2/2013
WO 2013/036918 A2 3/2013
(Continued)

OTHER PUBLICATIONS

Koga et al., Role of Primers in Glucan Synthesis by Glucosyltransferases From *Streptococcus mutans* Strain OMZ176, vol. 129 (1983), J. Gen. Microbiol., pp. 751-754.
(Continued)

*Primary Examiner* — Yong D Pak

(57) ABSTRACT

A method for producing insoluble alpha-1,3-glucan is disclosed. Embodiments of the method comprise providing (i) oligosaccharides that comprise alpha-1,3 and alpha-1,6 glycosidic linkages, or (ii) oligosaccharides derived from a glucosyltransferase reaction; and contacting at least water, sucrose, a glucosyltransferase enzyme, and the oligosaccharides provided in the first step. Glucosyltransferase reaction compositions embodying such a method, and insoluble products thereof, are also disclosed. Yield and other product benefits can be realized when practicing the disclosed subject matter.

18 Claims, 2 Drawing Sheets

Figure 1:
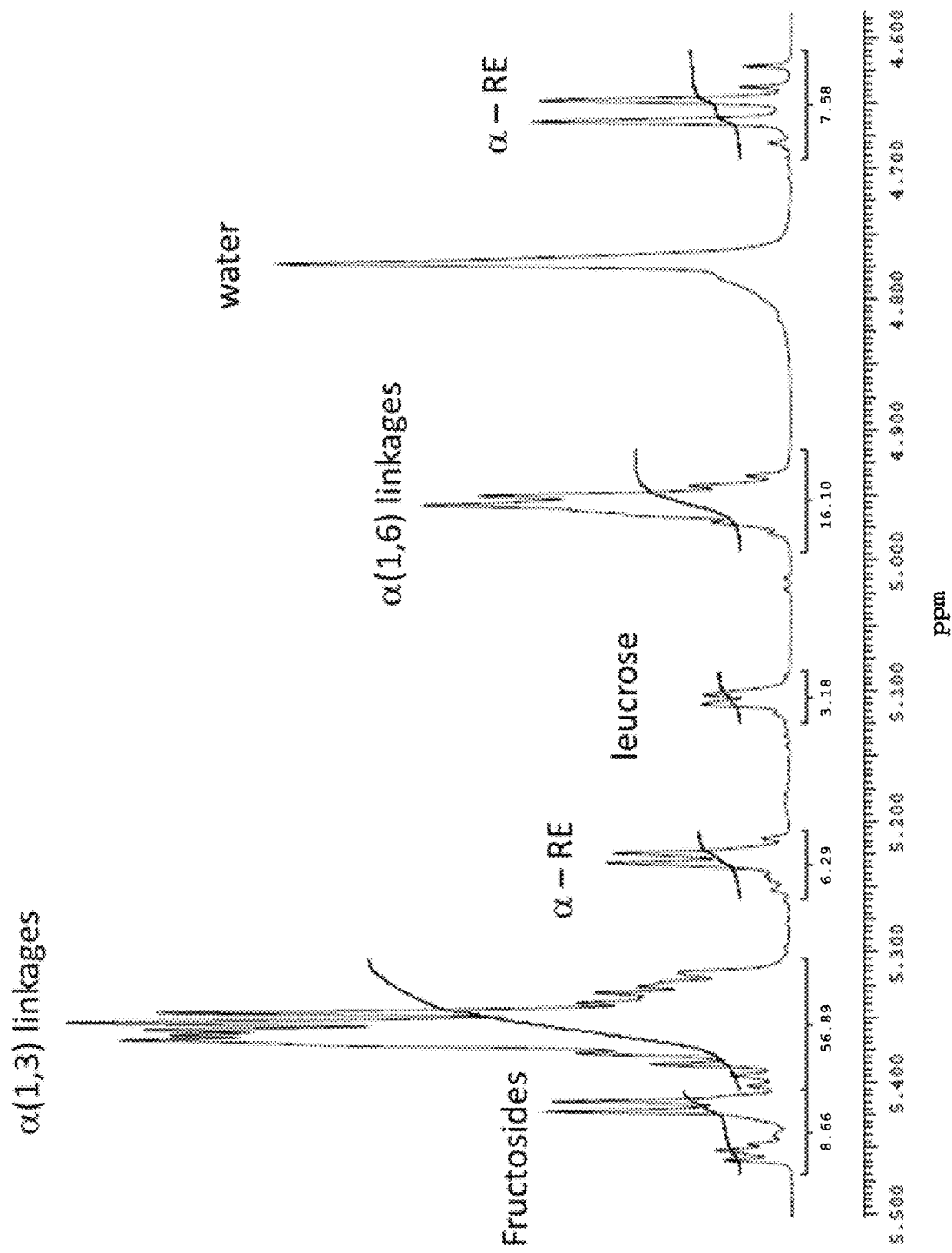

Specification includes a Sequence Listing.

(51) Int. Cl.
| | |
|---|---|
| *C12N 15/00* | (2006.01) |
| *C08B 37/02* | (2006.01) |
| *C08L 5/00* | (2006.01) |
| *C08B 37/00* | (2006.01) |
| *C12N 15/10* | (2006.01) |
| *C12P 19/18* | (2006.01) |
| *C12Q 1/48* | (2006.01) |

(52) U.S. Cl.
CPC .............. *C08L 5/00* (2013.01); *C12N 9/1048* (2013.01); *C12N 15/102* (2013.01); *C12P 19/18* (2013.01); *C12Q 1/48* (2013.01); *C12Y 204/01027* (2013.01)

(56) References Cited

U.S. PATENT DOCUMENTS

| | | | |
|---|---|---|---|
| 6,660,502 | B2 | 12/2003 | Catani et al. |
| 6,867,026 | B2 | 3/2005 | Van Geel-Schutten et al. |
| 7,000,000 | B1 | 2/2006 | O'Brien |
| 7,670,811 | B2 | 3/2010 | Vercauteren et al. |
| 8,642,757 | B2 | 2/2014 | O'Brien et al. |
| 8,871,474 | B2 * | 10/2014 | Payne ................ C08B 37/0009 435/97 |
| 2003/0153746 | A1 | 8/2003 | Van Lengerich et al. |
| 2005/0249853 | A1 | 11/2005 | Merrill et al. |
| 2013/0157316 | A1 | 6/2013 | Caimi et al. |
| 2013/0196384 | A1 | 8/2013 | Caimi et al. |
| 2013/0244287 | A1 | 9/2013 | O'Brien et al. |
| 2013/0244288 | A1 | 9/2013 | O'Brien et al. |
| 2014/0087431 | A1 | 3/2014 | Payne et al. |
| 2015/0167243 | A1 | 6/2015 | Bilodeau et al. |
| 2015/0232819 | A1 | 8/2015 | Paullin et al. |
| 2015/0240278 | A1 | 8/2015 | Nagy et al. |
| 2015/0240279 | A1 | 8/2015 | Nagy et al. |
| 2015/0275256 | A1 | 10/2015 | Fake et al. |
| 2016/0002693 | A1 | 1/2016 | Caimi et al. |
| 2017/0002335 | A1 * | 1/2017 | Payne ..................... C12Q 1/48 |
| 2017/0002336 | A1 | 1/2017 | Payne et al. |
| 2017/0166938 | A1 | 6/2017 | Nagy et al. |
| 2017/0204203 | A1 | 7/2017 | Massouda et al. |
| 2017/0208823 | A1 | 7/2017 | Massouda et al. |
| 2018/0021238 | A1 | 1/2018 | Huh et al. |
| 2018/0072998 | A1 | 3/2018 | Li et al. |

FOREIGN PATENT DOCUMENTS

| | | |
|---|---|---|
| WO | 2015/130881 A1 | 9/2015 |
| WO | 2015130881 A1 | 9/2015 |
| WO | 2015200590 A1 | 12/2015 |
| WO | 2015200612 A1 | 12/2015 |
| WO | 2016126685 A1 | 8/2016 |
| WO | 2017079595 A1 | 5/2017 |

OTHER PUBLICATIONS

Cantarel et al., The Carbohydrate-Active Enzymes Database (CAZY): An Expert Resource For Glycogenomics, Nucleic Acids Research, vol. 37 (2009), Database Issued, pp. 233-238.
Chun et al., On the Intrinsic Viscosity of Anionic and Nonionic Rodlike Polysaccharide Solutions, Macromol. Chem. Phys., vol. 195 (1994), pp. 701-711.
Komatsu et al., Kinetics of Dextran-Independent α-(1→3)-Glucan Synthesis by Strepto-Coccus Sobrinus Glucosyltransferase I, FEBS J., vol. 278 (2011), pp. 531-540.
Eifuku et al., Production and Partial Characterization of the Extra-Cellular Polysaccharides From Oral *Streptococcus salivarius*, Carbohydrate Research, vol. 194 (1999), pp. 247-260.
Goffin et al., A Systematic NMR Determination of α-D-Glucooligosaccharides, Effect of Linkage Type, Anomeric Configuration and Combination of Different Linkages Type on 13C Chemical Shifts for the Determination of Unknown Isomaltooligosaccharides, Bull. Korean Chem. Soc., vol. 30, (2009), pp. 2535-2541.
Kingston et al., Role of the C-Terminal YG Repeats of the Primer-Dependent Streptococcal Glucosyltransferase, GTFJ, in Binding to Dextran and Mutan, Microbiology, vol. 148 (2002), pp. 549-558.
Konishi et al., Structure and Enzymatic Properties of Genetically Truncated Forms of the Water-Insoluble Glucan-Synthesizing Glucosyltransferase From *Streptococcus sobrinus*, J. Biochem., vol. 126 (1999), pp. 287-295.
Leemhuis et al., Glucansucrases: Three-Dimensional Structures, Reactions, Mechanism, α-Glucan Analysis and Their Implications in Biotechnology and Food Applications, Journal of Biotechnology, vol. 163 (2013), pp. 250-272.
Monchois et al., Isolation of an Active Catalytic Core of *Streptococcus downei* MFE28 GTF-I Glucosyltransferase, Journal of Bacteriology, vol. 181, No. 7 (1999), pp. 2290-2292.
Monchois et al., Glucansucrases: Mechanism of Action and Structure-Function Relationships, FEMS Microbiology Reviews, vol. 23 (1999), pp. 131-151.
Rogers, Chapter 5: The Molecular Biology of Cariogenic Bacteria, From Molecular Biology, Horizon Scientific Press, Roy RB Russell (2008), pp. 120-122.
Simpson et al., Four Glucosyltransferases, GTJ, GTK, GTFL, and GTFM, From *Streptococcus salivarius* ATCC 25975, Microbiology, vol. 141 (1995), pp. 1451-1460.
Weaver et al., Weighted Intrinsic Viscosity Relationships for Polysaccharide Mixtures in Dilute Aqueous Solutions, Journal of Applied Polymer Sciences, vol. 35 (1988), pp. 1631-1637.
International Search Report—PCT/US2018/033854—dated Sep. 20, 2018.
Koga, Toshihiko et al., Role of Primers in Glucan Synthesis by Glucosyltransferases from *Streptococcus mutans* strain OMZ176, Journal of General Microbiology, 1983, pp. 751-774, vol. 129.
International Search Report and Written Opinion, PCT/US2018/033854, dated Sep. 20, 2018.

* cited by examiner

SEQUENCE LISTING

```
<160> NUMBER OF SEQ ID NOS: 16

<210> SEQ ID NO 1
<211> LENGTH: 4434
<212> TYPE: DNA
<213> ORGANISM: Artificial sequence
<220> FEATURE:
<223> OTHER INFORMATION: Codon-optimized sequence encoding GtfJ/7527

<400> SEQUENCE: 1
atggacgaaa cgcaggataa gaccgtgacg cagagcaaca gcggcaccac cgcttccctg      60
gtcactagcc ctgaagccac gaaagaggcg gacaaacgca cgaacactaa agaggccgac     120
gttctgacgc ctgcaaaaga aacgaacgca gtcgagactg cgaccaccac taacacccag     180
gcgacggcgg aggccgccac gaccgcgacc accgcggacg tcgcggtggc tgcggtgccg     240
aacaaagaag cggtcgttac cacggatgct ccggcggtca cgaccgagaa agcggaagaa     300
cagccggcta ccgttaaagc agaagtcgtc aatacggaag tgaaagcgcc ggaagcggct     360
ctgaaagaca gcgaggttga ggcagcgctg agcctgaaga acatcaagaa cattgatggc     420
aagtattact atgttaatga ggatggcagc cacaaagaga atttcgctat taccgtgaat     480
ggccagctgc tgtactttgg taaagacggt gcgctgacgt cctctagcac gtattctttt     540
accccaggca ctaccaatat cgtggacggt tttagcatta caaccgcgc ttacgacagc     600
```

```
agcgaggcga gctttgagct gatcgacggt tacttgaccg cagacagctg gtatcgtccg    660
gctagcatca tcaaagatgg tgttacgtgg caagcgtcca ccgccgagga ttttcgtccg    720
ctgctgatgg catggtggcc gaatgtggat acgcaggtga actatttgaa ttacatgtcc    780
aaagttttca acctggacgc gaaatactct agcaccgaca acaggaaac cctgaaagtg     840
gcagcaaaag acattcaaat caagattgaa caaaagattc aagcggagaa gagcacgcag    900
tggctgcgtg aaactatcag cgcctttgtg aaaacccagc cgcagtggaa caaagaaacc    960
gagaattaca gcaagggtgg tggtgaggac cacctgcaag gtggcgcact gctgtatgtt   1020
aacgacagcc gtacccttg gcgaatagc gattaccgtc gtctgaatcg caccgcaacc     1080
aatcagacgg gcacgatcga taagtctatt ctggacgagc agtctgaccc aaaccacatg   1140
ggcggtttcg actttctgct ggcgaacgac gtcgacctga gcaatccggt cgtgcaggct   1200
gagcagctga atcaaatcca ctatctgatg aattggggtt ccattgtgat gggtgacaag   1260
gatgcgaact ttgacggcat tcgtgtcgat gcagttgaca acgtggacgc ggacatgttg   1320
caactgtata ccaattactt ccgtgagtac tacggtgtga acaagagcga agctaacgca   1380
ctggctcaca tcagcgttct ggaggcgtgg agcctgaatg ataatcatta caatgacaag   1440
accgatggtg cggcactggc aatggagaat aagcaacgtc tggcgctgtt gttttcgttg   1500
gcgaaaccga tcaaagagcg taccccggca gtgagcccgc tgtataacaa caccttcaat   1560
accacccagc gtgatgaaaa gaccgattgg attaacaaag acggtagcaa ggcttacaac   1620
gaagatggca cggtcaaaca atcgaccatc ggtaagtaca acgagaaata cggtgacgca   1680
tccggtaact acgtttttcat ccgtgcccac gataacaacg tccaggacat catcgccgag   1740
atcatcaaga aagagatcaa cccgaaaagc gacggcttca ccatcaccga cgccgaaatg   1800
aagcaagcct ttgaaatcta taacaaagat atgctgtcga gcgacaaaaa gtataccctg   1860
aataacattc cggcagcgta tgccgtgatg ttgcagaata tggaaacgat taccgcgtc    1920
tattacggtg atctgtatac ggacgacggt cactacatgg aaaccaaatc tccgtattac   1980
gataccatcg tgaatttgat gaagagccgt atcaagtatg tttcgggtgg ccaggcgcaa   2040
cgtagctatt ggctgccgac cgacggtaag atggacaata gcgacgttga gctgtaccgc   2100
acgaatgagg tttacacgag cgtgcgctat ggtaaggata tcatgaccgc taatgatacc   2160
gaaggctcta gtattcccg caccagcggc caagtcacct tggtcgcgaa caatccgaag    2220
ctgaatctgg accaaagcgc caagttgaat gtggagatgg gcaaaatcca tgcgaatcag   2280
aagtatcgcg cactgattgt cggcactgcg gacggcatta gaactttac ttccgacgcg    2340
gacgccattg cagcgggtta tgtgaaagaa accgatagca acggcgtgct gaccttcggt   2400
gctaacgaca ttaagggcta cgaaacgttt gatatgagcg gtttcgtggc ggtgtgggtt   2460
ccggtgggtg catctgacaa tcaggacatt cgtgttgcgc cgagcaccga ggcaaagaaa   2520
gaaggtgagc tgaccttgaa ggcgacggaa gcgtatgata ccagctgat ttacgaaggc    2580
tttagcaatt ccagacgat cccagatggc agcgatccgt ccgtgtatac gaaccgcaag    2640
attgcggaga acgtggatct gttcaaaagc tggggtgtca ccagctttga gatggcaccg   2700
caatttgtct cggcggatga tggcaccttt ctggatagcg ttattcagaa tggctacgcc   2760
ttcgccgacc gttatgacct ggccatgtcc aagaacaaca gtatggtag caaagaggac    2820
ctgcgtgatg cactgaaagc actgcataag gcgggtattc aagctatcgc agactgggtt   2880
ccagaccaga tctaccagct gccgggcaaa gaagttgtca ccgccacccg tacgatggt    2940
gctggccgta agatcgcaga cgcgattatc gaccattctc tgtatgttgc aaacagcaaa   3000
```

```
agcagcggca aagattatca agcaaagtac ggtggcgagt tcctggccga gctgaaagcc    3060
aaatacccgg aaatgttcaa agttaacatg attagcacgg gtaagccgat tgatgactcc    3120
gtgaaattga agcaatggaa agccgagtac ttcaatggca ccaacgtttt ggaacgtggt    3180
gtcggctatg ttctgagcga cgaggcgacc ggtaagtatt tcacggtgac caaagaaggc    3240
aatttcattc cgctgcaact gacgggtaaa gagaaagtta tcacgggttt ctccagcgat    3300
ggtaagggta tcacctattt cggtacgagc ggtacgcagg cgaagtctgc gtttgttacc    3360
ttcaatggta acacctacta tttcgacgcg cgtggccaca tggttaccaa tagcgaatac    3420
agcccgaatg caaggacgt ctaccgtttt ctgccgaacg gtatcatgct gagcaatgcg    3480 tttacattg atgcgaacgg taatacctac ctgtacaact ctaagggtca aatgtacaaa    3540
ggcggttaca cgaaattcga tgtttctgaa acgataagg acggtaaaga gtccaaggtc    3600
gtcaagttcc gctactttac gaacgaaggc gtcatggcca agggtgttac cgtcattgat    3660
ggttttaccc aatacttcgg tgaggacggc tttcaagcga aggataagct ggtcaccttc    3720
aagggcaaga cgtattactt cgacgcacac actggtaatg gtatcaaaga tacctggcgc    3780
aatatcaatg gtaaatggta ctatttcgac gcgaatggcg ttgctgcgac cggtgcgcag    3840
gtgattaacg ccagaaact gtacttcaac gaggatggct cccaagtcaa aggcggcgtg    3900
gttaagaacg cagacggcac ctatagcaaa tacaaagaag ttttggtga gctggttact    3960 aacgagtttt tcacgactga tggcaatgtt tggtactacg ccggtgcaaa tggtaaaacc    4020
gttaccggtg cacaagtgat caacggccaa catttgtact tcaatgcgga cggttcccag    4080
gtgaagggtg gcgttgtcaa aacgcggat ggcacctaca gcaagtacaa tgctagcact    4140
ggtgaacgtc tgacgaacga gttctttacg accggtgata caattggta ttacattggc    4200 gcaaacggta agagcgtgac gggtgaggtc aagattggtg atgatactta cttttcgcg    4260 aaggatggca aacaagttaa aggtcaaacc gtcagcgccg gtaatggtcg cattagctac    4320
tactacggtg acagcggcaa cgtgcggtt agcacctgga ttgagattca gccgggtgtt    4380
tatgtgtatt tcgacaaaaa cggtttggcg taccctccgc gtgttctgaa ttaa          4434
```

<210> SEQ ID NO 2
<211> LENGTH: 1477
<212> TYPE: PRT
<213> ORGANISM: Artificial sequence
<220> FEATURE:
<223> OTHER INFORMATION: GtfJ/7527_N-terminally truncated enzyme with added start-methionine.

<400> SEQUENCE: 2

Met Asp Glu Thr Gln Asp Lys Thr Val Thr Gln Ser Asn Ser Gly Thr
1               5                   10                  15

Thr Ala Ser Leu Val Thr Ser Pro Glu Ala Thr Lys Glu Ala Asp Lys
            20                  25                  30

Arg Thr Asn Thr Lys Glu Ala Asp Val Leu Thr Pro Ala Lys Glu Thr
        35                  40                  45

Asn Ala Val Glu Thr Ala Thr Thr Thr Asn Thr Gln Ala Thr Ala Glu
    50                  55                  60

Ala Ala Thr Thr Ala Thr Ala Asp Val Val Ala Val Ala Val Pro
65                  70                  75                  80

Asn Lys Glu Ala Val Val Thr Thr Asp Ala Pro Ala Val Thr Thr Glu
                85                  90                  95

Lys Ala Glu Glu Gln Pro Ala Thr Val Lys Ala Glu Val Val Asn Thr

-continued

```
                100                 105                 110
Glu Val Lys Ala Pro Glu Ala Leu Lys Asp Ser Glu Val Glu Ala
            115                 120                 125
Ala Leu Ser Leu Lys Asn Ile Lys Asn Ile Asp Gly Lys Tyr Tyr
        130                 135                 140
Val Asn Glu Asp Gly Ser His Lys Glu Asn Phe Ala Ile Thr Val Asn
145                 150                 155                 160
Gly Gln Leu Leu Tyr Phe Gly Lys Asp Gly Ala Leu Thr Ser Ser Ser
                165                 170                 175
Thr Tyr Ser Phe Thr Pro Gly Thr Thr Asn Ile Val Asp Gly Phe Ser
                180                 185                 190
Ile Asn Asn Arg Ala Tyr Asp Ser Ser Glu Ala Ser Phe Glu Leu Ile
            195                 200                 205
Asp Gly Tyr Leu Thr Ala Asp Ser Trp Tyr Arg Pro Ala Ser Ile Ile
        210                 215                 220
Lys Asp Gly Val Thr Trp Gln Ala Ser Thr Ala Glu Asp Phe Arg Pro
225                 230                 235                 240
Leu Leu Met Ala Trp Trp Pro Asn Val Asp Thr Gln Val Asn Tyr Leu
                245                 250                 255
Asn Tyr Met Ser Lys Val Phe Asn Leu Asp Ala Lys Tyr Ser Ser Thr
                260                 265                 270
Asp Lys Gln Glu Thr Leu Lys Val Ala Ala Lys Asp Ile Gln Ile Lys
            275                 280                 285
Ile Glu Gln Lys Ile Gln Ala Glu Lys Ser Thr Gln Trp Leu Arg Glu
        290                 295                 300
Thr Ile Ser Ala Phe Val Lys Thr Gln Pro Gln Trp Asn Lys Glu Thr
305                 310                 315                 320
Glu Asn Tyr Ser Lys Gly Gly Glu Asp His Leu Gln Gly Gly Ala
                325                 330                 335
Leu Leu Tyr Val Asn Asp Ser Arg Thr Pro Trp Ala Asn Ser Asp Tyr
                340                 345                 350
Arg Arg Leu Asn Arg Thr Ala Thr Asn Gln Thr Gly Thr Ile Asp Lys
            355                 360                 365
Ser Ile Leu Asp Glu Gln Ser Asp Pro Asn His Met Gly Gly Phe Asp
        370                 375                 380
Phe Leu Leu Ala Asn Asp Val Asp Leu Ser Asn Pro Val Val Gln Ala
385                 390                 395                 400
Glu Gln Leu Asn Gln Ile His Tyr Leu Met Asn Trp Gly Ser Ile Val
                405                 410                 415
Met Gly Asp Lys Asp Ala Asn Phe Asp Gly Ile Arg Val Asp Ala Val
                420                 425                 430
Asp Asn Val Asp Ala Asp Met Leu Gln Leu Tyr Thr Asn Tyr Phe Arg
            435                 440                 445
Glu Tyr Tyr Gly Val Asn Lys Ser Glu Ala Asn Ala Leu Ala His Ile
        450                 455                 460
Ser Val Leu Glu Ala Trp Ser Leu Asn Asp Asn His Tyr Asn Asp Lys
465                 470                 475                 480
Thr Asp Gly Ala Ala Leu Ala Met Glu Asn Lys Gln Arg Leu Ala Leu
                485                 490                 495
Leu Phe Ser Leu Ala Lys Pro Ile Lys Glu Arg Thr Pro Ala Val Ser
                500                 505                 510
Pro Leu Tyr Asn Asn Thr Phe Asn Thr Thr Gln Arg Asp Glu Lys Thr
            515                 520                 525
```

```
Asp Trp Ile Asn Lys Asp Gly Ser Lys Ala Tyr Asn Glu Asp Gly Thr
            530                 535                 540
Val Lys Gln Ser Thr Ile Gly Lys Tyr Asn Glu Lys Tyr Gly Asp Ala
545                 550                 555                 560
Ser Gly Asn Tyr Val Phe Ile Arg Ala His Asp Asn Asn Val Gln Asp
                565                 570                 575
Ile Ile Ala Glu Ile Ile Lys Lys Glu Ile Asn Pro Lys Ser Asp Gly
            580                 585                 590
Phe Thr Ile Thr Asp Ala Glu Met Lys Gln Ala Phe Glu Ile Tyr Asn
                595                 600                 605
Lys Asp Met Leu Ser Ser Asp Lys Lys Tyr Thr Leu Asn Asn Ile Pro
610                 615                 620
Ala Ala Tyr Ala Val Met Leu Gln Asn Met Glu Thr Ile Thr Arg Val
625                 630                 635                 640
Tyr Tyr Gly Asp Leu Tyr Thr Asp Asp Gly His Tyr Met Glu Thr Lys
                645                 650                 655
Ser Pro Tyr Tyr Asp Thr Ile Val Asn Leu Met Lys Ser Arg Ile Lys
                660                 665                 670
Tyr Val Ser Gly Gly Gln Ala Gln Arg Ser Tyr Trp Leu Pro Thr Asp
            675                 680                 685
Gly Lys Met Asp Asn Ser Asp Val Glu Leu Tyr Arg Thr Asn Glu Val
    690                 695                 700
Tyr Thr Ser Val Arg Tyr Gly Lys Asp Ile Met Thr Ala Asn Asp Thr
705                 710                 715                 720
Glu Gly Ser Lys Tyr Ser Arg Thr Ser Gly Gln Val Thr Leu Val Ala
                725                 730                 735
Asn Asn Pro Lys Leu Asn Leu Asp Gln Ser Ala Lys Leu Asn Val Glu
            740                 745                 750
Met Gly Lys Ile His Ala Asn Gln Lys Tyr Arg Ala Leu Ile Val Gly
            755                 760                 765
Thr Ala Asp Gly Ile Lys Asn Phe Thr Ser Asp Ala Asp Ala Ile Ala
    770                 775                 780
Ala Gly Tyr Val Lys Glu Thr Asp Ser Asn Gly Val Leu Thr Phe Gly
785                 790                 795                 800
Ala Asn Asp Ile Lys Gly Tyr Glu Thr Phe Asp Met Ser Gly Phe Val
                805                 810                 815
Ala Val Trp Val Pro Val Gly Ala Ser Asp Asn Gln Asp Ile Arg Val
                820                 825                 830
Ala Pro Ser Thr Glu Ala Lys Lys Glu Gly Glu Leu Thr Leu Lys Ala
        835                 840                 845
Thr Glu Ala Tyr Asp Ser Gln Leu Ile Tyr Gly Phe Ser Asn Phe
    850                 855                 860
Gln Thr Ile Pro Asp Gly Ser Asp Pro Ser Val Tyr Thr Asn Arg Lys
865                 870                 875                 880
Ile Ala Glu Asn Val Asp Leu Phe Lys Ser Trp Gly Val Thr Ser Phe
                885                 890                 895
Glu Met Ala Pro Gln Phe Val Ser Ala Asp Asp Gly Thr Phe Leu Asp
            900                 905                 910
Ser Val Ile Gln Asn Gly Tyr Ala Phe Ala Asp Arg Tyr Asp Leu Ala
    915                 920                 925
Met Ser Lys Asn Asn Lys Tyr Gly Ser Lys Glu Asp Leu Arg Asp Ala
    930                 935                 940
```

Leu Lys Ala Leu His Lys Ala Gly Ile Gln Ala Ile Ala Asp Trp Val
945                 950                 955                 960

Pro Asp Gln Ile Tyr Gln Leu Pro Gly Lys Glu Val Val Thr Ala Thr
            965                 970                 975

Arg Thr Asp Gly Ala Gly Arg Lys Ile Ala Asp Ala Ile Ile Asp His
        980                 985                 990

Ser Leu Tyr Val Ala Asn Ser Lys Ser Ser Gly Lys Asp Tyr Gln Ala
    995                 1000                1005

Lys Tyr Gly Gly Glu Phe Leu Ala Glu Leu Lys Ala Lys Tyr Pro
1010                1015                1020

Glu Met Phe Lys Val Asn Met Ile Ser Thr Gly Lys Pro Ile Asp
1025                1030                1035

Asp Ser Val Lys Leu Lys Gln Trp Lys Ala Glu Tyr Phe Asn Gly
1040                1045                1050

Thr Asn Val Leu Glu Arg Gly Val Gly Tyr Val Leu Ser Asp Glu
1055                1060                1065

Ala Thr Gly Lys Tyr Phe Thr Val Thr Lys Glu Gly Asn Phe Ile
1070                1075                1080

Pro Leu Gln Leu Thr Gly Lys Glu Lys Val Ile Thr Gly Phe Ser
1085                1090                1095

Ser Asp Gly Lys Gly Ile Thr Tyr Phe Gly Thr Ser Gly Thr Gln
1100                1105                1110

Ala Lys Ser Ala Phe Val Thr Phe Asn Gly Asn Thr Tyr Tyr Phe
1115                1120                1125

Asp Ala Arg Gly His Met Val Thr Asn Ser Glu Tyr Ser Pro Asn
1130                1135                1140

Gly Lys Asp Val Tyr Arg Phe Leu Pro Asn Gly Ile Met Leu Ser
1145                1150                1155

Asn Ala Phe Tyr Ile Asp Ala Asn Gly Asn Thr Tyr Leu Tyr Asn
1160                1165                1170

Ser Lys Gly Gln Met Tyr Lys Gly Gly Tyr Thr Lys Phe Asp Val
1175                1180                1185

Ser Glu Thr Asp Lys Asp Gly Lys Glu Ser Lys Val Val Lys Phe
1190                1195                1200

Arg Tyr Phe Thr Asn Glu Gly Val Met Ala Lys Gly Val Thr Val
1205                1210                1215

Ile Asp Gly Phe Thr Gln Tyr Phe Gly Glu Asp Gly Phe Gln Ala
1220                1225                1230

Lys Asp Lys Leu Val Thr Phe Lys Gly Lys Thr Tyr Tyr Phe Asp
1235                1240                1245

Ala His Thr Gly Asn Gly Ile Lys Asp Thr Trp Arg Asn Ile Asn
1250                1255                1260

Gly Lys Trp Tyr Tyr Phe Asp Ala Asn Gly Val Ala Ala Thr Gly
1265                1270                1275

Ala Gln Val Ile Asn Gly Gln Lys Leu Tyr Phe Asn Glu Asp Gly
1280                1285                1290

Ser Gln Val Lys Gly Gly Val Val Lys Asn Ala Asp Gly Thr Tyr
1295                1300                1305

Ser Lys Tyr Lys Glu Gly Phe Gly Glu Leu Val Thr Asn Glu Phe
1310                1315                1320

Phe Thr Thr Asp Gly Asn Val Trp Tyr Tyr Ala Gly Ala Asn Gly
1325                1330                1335

Lys Thr Val Thr Gly Ala Gln Val Ile Asn Gly Gln His Leu Tyr

-continued

```
                      1340              1345              1350

Phe Asn Ala Asp Gly Ser Gln Val Lys Gly Gly Val Val Lys Asn
    1355              1360              1365

Ala Asp Gly Thr Tyr Ser Lys Tyr Asn Ala Ser Thr Gly Glu Arg
    1370              1375              1380

Leu Thr Asn Glu Phe Phe Thr Thr Gly Asp Asn Asn Trp Tyr Tyr
    1385              1390              1395

Ile Gly Ala Asn Gly Lys Ser Val Thr Gly Glu Val Lys Ile Gly
    1400              1405              1410

Asp Asp Thr Tyr Phe Phe Ala Lys Asp Gly Lys Gln Val Lys Gly
    1415              1420              1425

Gln Thr Val Ser Ala Gly Asn Gly Arg Ile Ser Tyr Tyr Tyr Gly
    1430              1435              1440

Asp Ser Gly Lys Arg Ala Val Ser Thr Trp Ile Glu Ile Gln Pro
    1445              1450              1455

Gly Val Tyr Val Tyr Phe Asp Lys Asn Gly Leu Ala Tyr Pro Pro
    1460              1465              1470

Arg Val Leu Asn
    1475

<210> SEQ ID NO 3
<211> LENGTH: 4308
<212> TYPE: DNA
<213> ORGANISM: Artificial sequence
<220> FEATURE:
<223> OTHER INFORMATION: Codon-optimized sequence encoding Gtf 0874

<400> SEQUENCE: 3
atggttgacg gcaaatacta ctattatgat caggacggta acgtaaagaa gaatttcgcg     60
gtgagcgttg gtgacaaaat ctactacttc gatgaaactg gtgcatataa ggataccagc    120
aaagtggacg ccgacaagag cagcagcgcg gttagccaaa acgcgaccat ctttgcggcg    180
aataaccgtg cgtacagcac ctctgcaaag aattttgaag cggtggataa ctacctgacc    240
gcagacagct ggtatcgtcc gaaatccatc ctgaaggacg gcaaaacctg gaccgagagc    300
ggtaaggatg atttccgtcc actgctgatg gcatggtggc tgacaccgga actaagcgc     360 aactacgtga actatatgaa taaagtggtc ggtattgaca agacgtacac tgcggaaacg    420
tcgcaagcgg atttgaccgc agcggcggag ctggttcaag cgcgtatcga gcagaagatt    480
accagcgaaa caacaccaa atggctgcgc gaagcaatct ccgcgttcgt taagacgcag    540
cctcagtgga cggcgagtc cgaaaagccg tatgacgatc acttgcagaa cggtgcgctg    600
ctgtttgata ccaaaccga cctgacgcca gacacccaaa gcaattaccg tttgctgaac    660
cgtaccccga ccaatcagac tggtagcctg atagccgtt ttacgtataa tccgaatgac    720
ccgttgggcg gctacgattt cttgctggcg aacgacgttg acaatagcaa tccggtcgtc    780
caggctgaac agttgaactg gctgcattat ctgctgaact ttggctctat ttacgctaac    840
gatgccgacg ccaattttga cagcattcgc gttgatgccg tcgataatgt cgatgctgat    900
ctgctgcaaa tcagcagcga ttacctgaaa gcagcgtatg catcgacaa gaataacaag    960 aatgcgaaca accatgttag catcgtcgaa gcgtggagcg acaatgatac cccgtatttg   1020
cacgacgatg gcgataatct gatgaacatg gacaacaaat tcgcctgtc catgctgtgg   1080 agcctggcaa agccgctgga caaacgtagc ggtttgaacc gctgattca caatagcctg   1140 gtggaccgcg aggtggacga tcgtgaagtg gaaaccgtgc gtcctacag ctttgctcgt   1200
```

```
gcacatgata gcgaggtgca ggacatcatc cgtgacatta tcaaggctga gattaaccca    1260
aatagctttg gttatagctt cactcaagaa gagatcgagc aagcctttaa gatttacaac    1320
gaggatttga agaaaacgga caagaaatac acccactaca atgtgccgct gagctacacc    1380
ctgctgctga ccaacaaggg cagcatcccg cgtgtgtact atggtgatat gttcaccgat    1440
gatggccaat acatggcaaa caagaccgtc aactacgacg caatcgagag cctgctgaaa    1500
gcccgtatga aatatgtcag cggtggccaa gcaatgcaga actatcaaat tggtaatggc    1560
gagattttga ccagcgtgcg ctatggtaaa ggtgccctga agcagagcga taagggtgac    1620
gcgacgacgc gcactagcgg tgttggcgtg gttatgggta atcagccgaa cttctccctg    1680
gacggtaaag ttgtggccct gaatatgggt gcggcccatg cgaatcaaga ataccgtgca    1740
ctgatggtca gcactaaaga cggtgtggca acttacgcaa ccgatgctga cgcatccaaa    1800
gcgggcctgg tcaagcgtac cgacgagaac ggctacctgt acttcctgaa tgatgatctg    1860
aagggcgtcg cgaaccctca ggtttccggc ttcttgcaag tgtgggttcc agttggtgcc    1920
gccgatgacc aggacattcg cgtcgccgcc agcgacacgg cgagcacgga tggtaaaagc    1980
ctgcatcaag atgcggcgat ggacagccgc gtcatgtttg agggtttcag caattttcaa    2040
tccttcgcga ccaaagaaga agaatacacg aatgttgtta tcgcgaacaa tgtcgataag    2100
ttcgttagct ggggtatcac cgattttgaa atggctccgc agtatgttag cagcaccgac    2160
ggtcagttct tggacagcgt catccagaat ggctatgcgt ttactgatcg ctatgatctg    2220
ggtatgtcca aggcgaacaa gtatggcacg gcagaccaac tggttaaggc aatcaaagcc    2280
ctgcacgcta aaggcctgaa agttatgcgg gactgggtcc cggatcaaat gtacaccttt    2340
ccaaaacagg aagttgtgac cgttacccgc accgacaaat tcggtaaacc gatcgccggc    2400
tctcaaatca atcacagctt gtatgtgacc gacaccaaat ccagcggcga cgactaccaa    2460
gcgaagtacg gcggtgcctt cctggatgaa ctgaaagaaa agtacccgga actgttcacg    2520
aaaaagcaaa ttagcacggg ccaagcgatt gatccgagcg tgaaaatcaa gcagtggagc    2580
gcaaaatact tcaatggttc gaatatcctg ggtcgcggtg cggactatgt gctgagcgac    2640
caggtcagca ataagtattt caacgtgcg agcgacacct tgttcctgcc gtccagcctg    2700
ctgggcaagg tcgtggagag cggcattcgt tacgacggca agggttacat ctacaacagc    2760
tccgcgaccg gcgatcaggt caaagcgtct ttcattacgg aagccggtaa cctgtattac    2820
ttcggcaaag acggttacat ggttactggt gcccagacga ttaatggcgc caactacttc    2880
ttcctggaaa acggtacggc actgcgtaat acgatttaca ccgatgctca aggtaatagc    2940
cactattacg cgaatgatgg caaacgctat gaaaatggct atcaacagtt cggtaacgat    3000
tggcgctact ttaaagatgg taacatggca gtcggcctga ccacggttga tggcaacgtg    3060
caatactttg acaaagacgg cgtccaggca aaggataaga ttatcgtcac ccgtgatggc    3120
aaggtccgtt acttcgatca gcacaacggt aacgcggcga ccaacacgtt cattgctgat    3180
aaaactggcc attggtatta cctgggtaaa gatggcgtcg cggtgactgg cgcccagacc    3240
gtcggcaaac aaaaactgta cttcgaggcc aacggtcaac aagttaaagg tgactttgtt    3300
acgtccgatg agggcaaact gtatttctat gacgttgatt ctggtgacat gtggacggac    3360
accttcatcg aggataaggc gggcaactgg ttctatttgg gcaaggatgg tgcggcagtt    3420
acgggtgccc aaacgattcg cggtcagaag ctgtacttca aggccaatgg tcaacaggtc    3480
aagggtgaca ttgttaaggg caccgacggt aaaatccgct actatgatgc aaaatccggt    3540
gaacaggtgt tcaacaaaac ggtgaaagct gcggatggca aaacgtatgt tatcggtaat    3600
```

```
gatggtgtcg cggtggaccc tagcgtggtt aaaggtcaaa cctttaagga cgcttcgggc   3660
gctctgcgtt tctacaactt gaagggtcaa ctggtcactg gcagcggctg gtatgaaacc   3720
gcgaaccatg actgggttta cattcagtcc ggcaaggcac tgaccggcga cagaccatt    3780 aacggtcaac acctgtattt caagaagat ggtcaccaag tcaagggtca gttggtcacg   3840
ggcaccgatg gtaaagtgcg ttactatgac gccaacagcg gtgaccaagc attcaacaag   3900
agcgtcactg tgaatggtaa aacctattac tttggcaacg atggtacggc gcagactgct   3960
ggcaacccga agggtcagac gttcaaggat ggctccgaca tccgttttta ctctatggaa   4020
ggccaactgg tgaccggctc gggttggtac gagaacgcgc aaggccagtg gctgtatgtg   4080
aaaaacggta aggtgctgac tggtctgcaa accgttggca gccagcgtgt ttacttcgac   4140
gagaatggta ttcaggccaa gggcaaagca gtgcgtacca gcgatggcaa aattcgttat   4200
ttcgacgaaa acagcggcag catgatcacg aatcaatgga agttcgtcta tggtcagtat   4260
tactactttg gtaacgacgg tgcacgtatt taccgtggtt ggaactaa                4308
```

<210> SEQ ID NO 4
<211> LENGTH: 1435
<212> TYPE: PRT
<213> ORGANISM: Artificial sequence
<220> FEATURE:
<223> OTHER INFORMATION: Gtf 0874_N-terminally truncated enzyme with
      added start-methionine.

<400> SEQUENCE: 4

```
Met Val Asp Gly Lys Tyr Tyr Tyr Asp Gln Asp Gly Asn Val Lys
1               5                   10                  15

Lys Asn Phe Ala Val Ser Val Gly Asp Lys Ile Tyr Tyr Phe Asp Glu
            20                  25                  30

Thr Gly Ala Tyr Lys Asp Thr Ser Lys Val Asp Ala Asp Lys Ser Ser
        35                  40                  45

Ser Ala Val Ser Gln Asn Ala Thr Ile Phe Ala Ala Asn Asn Arg Ala
    50                  55                  60

Tyr Ser Thr Ser Ala Lys Asn Phe Glu Ala Val Asp Asn Tyr Leu Thr
65                  70                  75                  80

Ala Asp Ser Trp Tyr Arg Pro Lys Ser Ile Leu Lys Asp Gly Lys Thr
                85                  90                  95

Trp Thr Glu Ser Gly Lys Asp Asp Phe Arg Pro Leu Leu Met Ala Trp
            100                 105                 110

Trp Pro Asp Thr Glu Thr Lys Arg Asn Tyr Val Asn Tyr Met Asn Lys
        115                 120                 125

Val Val Gly Ile Asp Lys Thr Tyr Thr Ala Glu Thr Ser Gln Ala Asp
    130                 135                 140

Leu Thr Ala Ala Ala Glu Leu Val Gln Ala Arg Ile Glu Gln Lys Ile
145                 150                 155                 160

Thr Ser Glu Asn Asn Thr Lys Trp Leu Arg Gly Ala Ile Ser Ala Phe
                165                 170                 175

Val Lys Thr Gln Pro Gln Trp Asn Gly Glu Ser Glu Lys Pro Tyr Asp
            180                 185                 190

Asp His Leu Gln Asn Gly Ala Leu Leu Phe Asp Asn Gln Thr Asp Leu
        195                 200                 205

Thr Pro Asp Thr Gln Ser Asn Tyr Arg Leu Leu Asn Arg Thr Pro Thr
    210                 215                 220

Asn Gln Thr Gly Ser Leu Asp Ser Arg Phe Thr Tyr Asn Pro Asn Asp
```

```
                225                 230                 235                 240
        Pro Leu Gly Gly Tyr Asp Phe Leu Leu Ala Asn Asp Val Asp Asn Ser
                        245                 250                 255
        Asn Pro Val Val Gln Ala Glu Gln Leu Asn Trp Leu His Tyr Leu Leu
                        260                 265                 270
        Asn Phe Gly Ser Ile Tyr Ala Asn Asp Ala Asp Ala Asn Phe Asp Ser
                        275                 280                 285
        Ile Arg Val Asp Ala Val Asp Asn Val Asp Ala Asp Leu Leu Gln Ile
                    290                 295                 300
        Ser Ser Asp Tyr Leu Lys Ala Ala Tyr Gly Ile Asp Lys Asn Asn Lys
        305                 310                 315                 320
        Asn Ala Asn Asn His Val Ser Ile Val Glu Ala Trp Ser Asp Asn Asp
                            325                 330                 335
        Thr Pro Tyr Leu His Asp Asp Gly Asp Asn Leu Met Asn Met Asp Asn
                        340                 345                 350
        Lys Phe Arg Leu Ser Met Leu Trp Ser Leu Ala Lys Pro Leu Asp Lys
                        355                 360                 365
        Arg Ser Gly Leu Asn Pro Leu Ile His Asn Ser Leu Val Asp Arg Glu
                    370                 375                 380
        Val Asp Asp Arg Glu Val Glu Thr Val Pro Ser Tyr Ser Phe Ala Arg
        385                 390                 395                 400
        Ala His Asp Ser Glu Val Gln Asp Ile Ile Arg Asp Ile Ile Lys Ala
                            405                 410                 415
        Glu Ile Asn Pro Asn Ser Phe Gly Tyr Ser Phe Thr Gln Glu Glu Ile
                        420                 425                 430
        Glu Gln Ala Phe Lys Ile Tyr Asn Glu Asp Leu Lys Lys Thr Asp Lys
                        435                 440                 445
        Lys Tyr Thr His Tyr Asn Val Pro Leu Ser Tyr Thr Leu Leu Leu Thr
                    450                 455                 460
        Asn Lys Gly Ser Ile Pro Arg Val Tyr Tyr Gly Asp Met Phe Thr Asp
        465                 470                 475                 480
        Asp Gly Gln Tyr Met Ala Asn Lys Thr Val Asn Tyr Asp Ala Ile Glu
                            485                 490                 495
        Ser Leu Leu Lys Ala Arg Met Lys Tyr Val Ser Gly Gly Gln Ala Met
                        500                 505                 510
        Gln Asn Tyr Gln Ile Gly Asn Gly Glu Ile Leu Thr Ser Val Arg Tyr
                        515                 520                 525
        Gly Lys Gly Ala Leu Lys Gln Ser Asp Lys Gly Asp Ala Thr Thr Arg
                    530                 535                 540
        Thr Ser Gly Val Gly Val Val Met Gly Asn Gln Pro Asn Phe Ser Leu
        545                 550                 555                 560
        Asp Gly Lys Val Val Ala Leu Asn Met Gly Ala Ala His Ala Asn Gln
                            565                 570                 575
        Glu Tyr Arg Ala Leu Met Val Ser Thr Lys Asp Gly Val Ala Thr Tyr
                        580                 585                 590
        Ala Thr Asp Ala Asp Ala Ser Lys Ala Gly Leu Val Lys Arg Thr Asp
                        595                 600                 605
        Glu Asn Gly Tyr Leu Tyr Phe Leu Asn Asp Asp Leu Lys Gly Val Ala
                    610                 615                 620
        Asn Pro Gln Val Ser Gly Phe Leu Gln Val Trp Val Pro Val Gly Ala
        625                 630                 635                 640
        Ala Asp Asp Gln Asp Ile Arg Val Ala Ala Ser Asp Thr Ala Ser Thr
                            645                 650                 655
```

```
Asp Gly Lys Ser Leu His Gln Asp Ala Ala Met Asp Ser Arg Val Met
        660                 665                 670

Phe Glu Gly Phe Ser Asn Phe Gln Ser Phe Ala Thr Lys Glu Glu Glu
        675                 680                 685

Tyr Thr Asn Val Val Ile Ala Asn Asn Val Asp Lys Phe Val Ser Trp
690                 695                 700

Gly Ile Thr Asp Phe Glu Met Ala Pro Gln Tyr Val Ser Ser Thr Asp
705                 710                 715                 720

Gly Gln Phe Leu Asp Ser Val Ile Gln Asn Gly Tyr Ala Phe Thr Asp
                725                 730                 735

Arg Tyr Asp Leu Gly Met Ser Lys Ala Asn Lys Tyr Gly Thr Ala Asp
                740                 745                 750

Gln Leu Val Lys Ala Ile Lys Ala Leu His Ala Lys Gly Leu Lys Val
                755                 760                 765

Met Ala Asp Trp Val Pro Asp Gln Met Tyr Thr Phe Pro Lys Gln Glu
                770                 775                 780

Val Val Thr Val Thr Arg Thr Asp Lys Phe Gly Lys Pro Ile Ala Gly
785                 790                 795                 800

Ser Gln Ile Asn His Ser Leu Tyr Val Thr Asp Thr Lys Ser Ser Gly
                805                 810                 815

Asp Asp Tyr Gln Ala Lys Tyr Gly Gly Ala Phe Leu Asp Glu Leu Lys
                820                 825                 830

Glu Lys Tyr Pro Glu Leu Phe Thr Lys Lys Gln Ile Ser Thr Gly Gln
                835                 840                 845

Ala Ile Asp Pro Ser Val Lys Ile Lys Gln Trp Ser Ala Lys Tyr Phe
850                 855                 860

Asn Gly Ser Asn Ile Leu Gly Arg Gly Ala Asp Tyr Val Leu Ser Asp
865                 870                 875                 880

Gln Val Ser Asn Lys Tyr Phe Asn Val Ala Ser Asp Thr Leu Phe Leu
                885                 890                 895

Pro Ser Ser Leu Leu Gly Lys Val Val Glu Ser Gly Ile Arg Tyr Asp
                900                 905                 910

Gly Lys Gly Tyr Ile Tyr Asn Ser Ser Ala Thr Gly Asp Gln Val Lys
                915                 920                 925

Ala Ser Phe Ile Thr Glu Ala Gly Asn Leu Tyr Tyr Phe Gly Lys Asp
                930                 935                 940

Gly Tyr Met Val Thr Gly Ala Gln Thr Ile Asn Gly Ala Asn Tyr Phe
945                 950                 955                 960

Phe Leu Glu Asn Gly Thr Ala Leu Arg Asn Thr Ile Tyr Thr Asp Ala
                965                 970                 975

Gln Gly Asn Ser His Tyr Tyr Ala Asn Asp Gly Lys Arg Tyr Glu Asn
                980                 985                 990

Gly Tyr Gln Gln Phe Gly Asn Asp Trp Arg Tyr Phe Lys Asp Gly Asn
                995                 1000                1005

Met Ala Val Gly Leu Thr Thr Val Asp Gly Asn Val Gln Tyr Phe
        1010                1015                1020

Asp Lys Asp Gly Val Gln Ala Lys Asp Lys Ile Ile Val Thr Arg
        1025                1030                1035

Asp Gly Lys Val Arg Tyr Phe Asp Gln His Asn Gly Asn Ala Ala
        1040                1045                1050

Thr Asn Thr Phe Ile Ala Asp Lys Thr Gly His Trp Tyr Tyr Leu
        1055                1060                1065
```

Gly Lys Asp Gly Val Ala Val Thr Gly Ala Gln Thr Val Gly Lys
    1070                1075                1080

Gln Lys Leu Tyr Phe Glu Ala Asn Gly Gln Gln Val Lys Gly Asp
    1085                1090                1095

Phe Val Thr Ser Asp Glu Gly Lys Leu Tyr Phe Tyr Asp Val Asp
    1100                1105                1110

Ser Gly Asp Met Trp Thr Asp Thr Phe Ile Glu Asp Lys Ala Gly
    1115                1120                1125

Asn Trp Phe Tyr Leu Gly Lys Asp Gly Ala Ala Val Thr Gly Ala
    1130                1135                1140

Gln Thr Ile Arg Gly Gln Lys Leu Tyr Phe Lys Ala Asn Gly Gln
    1145                1150                1155

Gln Val Lys Gly Asp Ile Val Lys Gly Thr Asp Gly Lys Ile Arg
    1160                1165                1170

Tyr Tyr Asp Ala Lys Ser Gly Glu Gln Val Phe Asn Lys Thr Val
    1175                1180                1185

Lys Ala Ala Asp Gly Lys Thr Tyr Val Ile Gly Asn Asp Gly Val
    1190                1195                1200

Ala Val Asp Pro Ser Val Val Lys Gly Gln Thr Phe Lys Asp Ala
    1205                1210                1215

Ser Gly Ala Leu Arg Phe Tyr Asn Leu Lys Gly Gln Leu Val Thr
    1220                1225                1230

Gly Ser Gly Trp Tyr Glu Thr Ala Asn His Asp Trp Val Tyr Ile
    1235                1240                1245

Gln Ser Gly Lys Ala Leu Thr Gly Glu Gln Thr Ile Asn Gly Gln
    1250                1255                1260

His Leu Tyr Phe Lys Glu Asp Gly His Gln Val Lys Gly Gln Leu
    1265                1270                1275

Val Thr Gly Thr Asp Gly Lys Val Arg Tyr Tyr Asp Ala Asn Ser
    1280                1285                1290

Gly Asp Gln Ala Phe Asn Lys Ser Val Thr Val Asn Gly Lys Thr
    1295                1300                1305

Tyr Tyr Phe Gly Asn Asp Gly Thr Ala Gln Thr Ala Gly Asn Pro
    1310                1315                1320

Lys Gly Gln Thr Phe Lys Asp Gly Ser Asp Ile Arg Phe Tyr Ser
    1325                1330                1335

Met Glu Gly Gln Leu Val Thr Gly Ser Gly Trp Tyr Glu Asn Ala
    1340                1345                1350

Gln Gly Gln Trp Leu Tyr Val Lys Asn Gly Lys Val Leu Thr Gly
    1355                1360                1365

Leu Gln Thr Val Gly Ser Gln Arg Val Tyr Phe Asp Glu Asn Gly
    1370                1375                1380

Ile Gln Ala Lys Gly Lys Ala Val Arg Thr Ser Asp Gly Lys Ile
    1385                1390                1395

Arg Tyr Phe Asp Glu Asn Ser Gly Ser Met Ile Thr Asn Gln Trp
    1400                1405                1410

Lys Phe Val Tyr Gly Gln Tyr Tyr Phe Gly Asn Asp Gly Ala
    1415                1420                1425

Arg Ile Tyr Arg Gly Trp Asn
    1430                1435

<210> SEQ ID NO 5
<211> LENGTH: 4311
<212> TYPE: DNA

<213> ORGANISM: Artificial sequence
<220> FEATURE:
<223> OTHER INFORMATION: Codon-optimized sequence encoding Gtf 1724

<400> SEQUENCE: 5

| | | | | | |
|---|---|---|---|---|---|
| atggttgacg | gcaaatacta | ctactacgat | caggacggca | acgtaaagaa | aaacttcgcg | 60 |
| gttagcgtgg | gcgagaaaat | ctattacttt | gacgaaactg | gcgcctacaa | agacaccagc | 120 |
| aaagttgagg | cggacaaaag | cggcagcgac | attagcaagg | aagagactac | cttcgcggca | 180 |
| aacaaccgcg | cctacagcac | cagcgcggag | aattttgagg | cgatcgacaa | ttatctgacc | 240 |
| gcggactcct | ggtatcgtcc | taaatccatc | ctgaaggatg | gcaaaacgtg | gacggaaagc | 300 |
| agcaaagatg | actttcgtcc | gctgctgatg | gcgtggtggc | cggataccga | aacgaagcgc | 360 |
| aattacgtga | actacatgaa | caaagttgtt | ggcatcgaca | agacctatac | cgcggaaacc | 420 |
| agccaggccg | acttgaccgc | tgcggcggaa | ctggtgcaag | cacgcattga | gcagaagatc | 480 |
| acgaccgaac | agaacacgaa | atggctgcgt | gaggcaatct | cggcatttgt | taaaacgcaa | 540 |
| ccgcagtgga | acggtgaaag | cgagaagccg | tacgacgatc | acctgcaaaa | cggtgctctg | 600 |
| aaatttgata | tcagagcga | cctgaccccg | gatacgcaaa | gcaactaccg | tctgttgaac | 660 |
| cgtaccccga | ctaatcagac | gggtagcctg | acagccgct | tcacttataa | cgcgaacgac | 720 |
| cctttgggcg | ttatgagct | gctgctggca | aatgacgtcg | ataacagcaa | tccgatcgtg | 780 |
| caggcggagc | agctgaactg | gctgcattac | ctgctgaatt | ttggtacgat | ctacgccaaa | 840 |
| gatgccgacg | ctaacttcga | tagcattcgt | gtggacgcgg | ttgataacgt | cgatgcggat | 900 |
| ctgctgcaaa | ttagcagcga | ttacctgaaa | gcagcctacg | gcattgataa | gaataacaaa | 960 |
| aacgcgaaca | accacgtgag | cattgtcgaa | gcctggagcg | ataatgatac | cccgtacctg | 1020 |
| catgacgatg | gtgacaacct | gatgaatatg | gataacaaat | ttcgcctgtc | catgctgtgg | 1080 |
| tcgctggcca | aaccgctgga | caagcgtagc | ggtctgaacc | cgctgattca | taacagcttg | 1140 |
| gtggatcgtg | aagttgatga | ccgcgaggtt | gaaacggttc | cgagctattc | ttttgcacgt | 1200 |
| gcgcatgata | gcgaggtcca | ggacttgatc | cgtgacatca | tcaaggcaga | gatcaatccg | 1260 |
| aacgcattcg | gttatagctt | tacccaagac | gagattgacc | aggcctttaa | gatttacaat | 1320 |
| gaggatctga | agaaaacgga | taagaaatac | acccactata | atgtgccgtt | gagctacacc | 1380 |
| ctgctgctga | cgaataaggg | tagcatccca | cgtgtctact | atggtgatat | gtttaccgac | 1440 |
| gatggtcagt | atatggcgaa | caaaaccgtc | aactatgacg | ccattgaatc | tctgctgaaa | 1500 |
| gcgcgtatga | gtatgtcgc | tggcggtcaa | gcaatgcaga | actaccaaat | cggtaatggt | 1560 |
| gagatcctga | ccagcgttcg | ttatggtaag | ggtgccctga | acagagcga | caaaggtgat | 1620 |
| gcgaccacgc | gcaccagcgg | tgtcggtgtc | gttatgggca | atcagccaaa | ctttagcttg | 1680 |
| gacggcaaag | tggtggctct | gaacatgggc | gcagctcatg | cgaatcagga | gtatcgtgcg | 1740 |
| ctgatggtta | gcacgaaaga | cggtgttgcc | acgtatgcga | ccgatgcaga | tgcgagcaaa | 1800 |
| gccggtctgg | tcaaacgtac | cgacgaaaac | ggctacctgt | atttcctgaa | tgacgacctg | 1860 |
| aagggtgtgg | ccaatcctca | ggtgagcggt | ttcttgcagg | tgtgggttcc | ggtgggtgcc | 1920 |
| gcggatgatc | aagatatccg | tgttgcagct | agcgataccg | catccaccga | tggcaagagc | 1980 |
| ctgcaccaag | acgccgcgat | ggatagccgt | gttatgtttg | aaggcttctc | taactttcag | 2040 |
| tcctttgcca | cgaaagaaga | ggaatatacc | aacgtcgtta | tcgccaacaa | tgtggataag | 2100 |
| ttcgttagct | ggggtatcac | ggatttcgag | atggccccac | aatatgtttc | cagcaccgac | 2160 |
| ggtcaattcc | tggactctgt | cattcagaac | ggttatgctt | ttacggaccg | ttatgacttg | 2220 |

```
ggcatgtcta aggcaaacaa atacggcacg gccgatcaac tggttaaggc cattaaggcc    2280
ctgcacgcga agggcctgaa ggttatggca gattgggtgc cggatcagat gtataccttc    2340
ccgaaacagg aagtcgtgac cgttacccgt accgacaaat tggcaaacc gatcgcaggt     2400
tcccaaatca atcatagcct gtatgttacc gataccaagt ccagcggcga tgactatcag    2460
gccaaatatg gtggtgcgtt tctggacgag ctgaaggaga aatatccgga gctgttcacg    2520
aagaaacaaa tcagcacggg tcaagctatt gacccgagcg tgaaaatcaa acagtggtct    2580
gctaagtatt tcaatggctc caacatcctg ggtcgcggtg cggactacgt actgtcggat    2640
caggcgagca caaataccct gaacgtgtct gacgataaac tgttcctgcc gaaaaccttg    2700
ctgggccaag ttgtcgagag cggtatccgc tttgacggca ctggttatgt gtacaactct    2760
agcactacgg gtgaaaaagt taccgattcc ttcattacgg aggcaggtaa tctgtactac    2820
ttcggtcaag acggctatat ggtgaccggc gcacagaaca ttaagggcag caactattac    2880
ttcctggcca atggtgcggc cctgcgtaac accgtttaca ccgatgcgca aggtcagaat    2940
cactattacg gcaacgacgg caagcgttat gagaatggtt accaacagtt cggcaacgat    3000
tcttggcgtt acttcaaaaa tggcgtgatg gcgctgggtc tgactacggt ggatggtcac    3060
gtgcagtatt tcgataaaga tggtgtccag gccaaggata agatcattgt caccccgcgat   3120
ggcaaagtcc gctatttcga ccagcacaac ggtaatgcgg ttactaacac gttcgttgcg    3180
gacaagacgg gtcactggta ctatctgggc aaagacggcg tcgcggttac cggtgcgcag    3240
actgtgggta aacagcattt gtactttgaa gcgaacggtc aacaagtcaa gggtgacttc    3300
gtgacggcta agacggtaa actgtacttc tatgatgtgg acagcggcga catgtggacc    3360
aataccttta tcgaggataa agcgggtaat tggttctacc tgggtaagga cggtgcggcc    3420
gtcaccggtg cacagacgat caaaggccag aaattgtatt tcaaagccaa cggtcagcaa    3480
gttaaaggtg acattgtcaa ggacgcggac ggtaagatcc gttattacga cgctcagacc    3540
ggtgaacagg tctttaacaa gtccgttagc gtcaacggta agacctacta tttcggtagc    3600
gacggcaccg cgcaaacccca ggcgaatccg aaaggccaaa cctttaagga tggtagcggc    3660
gttctgcgtt tctacaattt ggagggccag tatgtctcgg cagcggctg gtacgaaacg    3720
gccgagcacg agtgggtata tgtgaaatcc ggtaaagttc tgaccggtgc ccagacgatt    3780
ggtaatcaac gtgtttactt caaggacaat ggtcaccagt gaaaggcca gctggtcacg    3840
ggtaatgacg gtaaattgcg ttactacgac gcgaacagcg tgatcaagc attcaacaaa    3900
tccgtcacgg ttaacggtaa aacctactac tttggcagcg atggtacggc gcagacgcag    3960
gctaatccta gggtcagac cttcaaagat ggtagcggcg tgctgcgttt tacaacttg     4020
gaaggccaat acgtgtctgg cagcggttgg tacaagaatg cgcagggcca gtggctgtac    4080
gtgaaagatg gcaaggtcct gaccggtctg caaacggtcg gcaatcagaa ggtctacttc    4140
gacaaaaatg gcatccaagc aaagggtaag gccgttcgca cgtccgatgg taaagtgcgc    4200
tactttgatg agaatagcgg tagcatgatt acgaaccaat ggaagttcgt ttacggtcaa    4260
tactattact tcggttctga cggcgcagcg gtttaccgtg gttggaacta a             4311
```

<210> SEQ ID NO 6
<211> LENGTH: 1436
<212> TYPE: PRT
<213> ORGANISM: Artificial sequence
<220> FEATURE:
<223> OTHER INFORMATION: Gtf 1724_N-terminally truncated enzyme with added start-methionine.

<400> SEQUENCE: 6

Met Val Asp Gly Lys Tyr Tyr Tyr Asp Gln Asp Gly Asn Val Lys
1               5                   10                  15

Lys Asn Phe Ala Val Ser Val Gly Glu Lys Ile Tyr Tyr Phe Asp Glu
            20                  25                  30

Thr Gly Ala Tyr Lys Asp Thr Ser Lys Val Glu Ala Asp Lys Ser Gly
        35                  40                  45

Ser Asp Ile Ser Lys Glu Glu Thr Thr Phe Ala Ala Asn Asn Arg Ala
50                  55                  60

Tyr Ser Thr Ser Ala Glu Asn Phe Glu Ala Ile Asp Asn Tyr Leu Thr
65                  70                  75                  80

Ala Asp Ser Trp Tyr Arg Pro Lys Ser Ile Leu Lys Asp Gly Lys Thr
                85                  90                  95

Trp Thr Glu Ser Ser Lys Asp Asp Phe Arg Pro Leu Leu Met Ala Trp
            100                 105                 110

Trp Pro Asp Thr Glu Thr Lys Arg Asn Tyr Val Asn Tyr Met Asn Lys
        115                 120                 125

Val Val Gly Ile Asp Lys Thr Tyr Thr Ala Glu Thr Ser Gln Ala Asp
130                 135                 140

Leu Thr Ala Ala Ala Glu Leu Val Gln Ala Arg Ile Glu Gln Lys Ile
145                 150                 155                 160

Thr Thr Glu Gln Asn Thr Lys Trp Leu Arg Glu Ala Ile Ser Ala Phe
                165                 170                 175

Val Lys Thr Gln Pro Gln Trp Asn Gly Glu Ser Glu Lys Pro Tyr Asp
            180                 185                 190

Asp His Leu Gln Asn Gly Ala Leu Lys Phe Asp Asn Gln Ser Asp Leu
        195                 200                 205

Thr Pro Asp Thr Gln Ser Asn Tyr Arg Leu Leu Asn Arg Thr Pro Thr
210                 215                 220

Asn Gln Thr Gly Ser Leu Asp Ser Arg Phe Thr Tyr Asn Ala Asn Asp
225                 230                 235                 240

Pro Leu Gly Gly Tyr Glu Leu Leu Ala Asn Asp Val Asp Asn Ser
                245                 250                 255

Asn Pro Ile Val Gln Ala Glu Gln Leu Asn Trp Leu His Tyr Leu Leu
            260                 265                 270

Asn Phe Gly Thr Ile Tyr Ala Lys Asp Ala Asp Ala Asn Phe Asp Ser
        275                 280                 285

Ile Arg Val Asp Ala Val Asp Asn Val Asp Ala Asp Leu Leu Gln Ile
        290                 295                 300

Ser Ser Asp Tyr Leu Lys Ala Ala Tyr Gly Ile Asp Lys Asn Asn Lys
305                 310                 315                 320

Asn Ala Asn Asn His Val Ser Ile Val Glu Ala Trp Ser Asp Asn Asp
                325                 330                 335

Thr Pro Tyr Leu His Asp Asp Gly Asp Asn Leu Met Asn Met Asp Asn
            340                 345                 350

Lys Phe Arg Leu Ser Met Leu Trp Ser Leu Ala Lys Pro Leu Asp Lys
        355                 360                 365

Arg Ser Gly Leu Asn Pro Leu Ile His Asn Ser Leu Val Asp Arg Glu
370                 375                 380

Val Asp Asp Arg Glu Val Glu Thr Val Pro Ser Tyr Ser Phe Ala Arg
385                 390                 395                 400

Ala His Asp Ser Glu Val Gln Asp Leu Ile Arg Asp Ile Ile Lys Ala

-continued

```
                405                 410                 415
Glu Ile Asn Pro Asn Ala Phe Gly Tyr Ser Phe Thr Gln Asp Glu Ile
                420                 425                 430

Asp Gln Ala Phe Lys Ile Tyr Asn Glu Asp Leu Lys Lys Thr Asp Lys
                435                 440                 445

Lys Tyr Thr His Tyr Asn Val Pro Leu Ser Tyr Thr Leu Leu Leu Thr
                450                 455                 460

Asn Lys Gly Ser Ile Pro Arg Val Tyr Gly Asp Met Phe Thr Asp
465                 470                 475                 480

Asp Gly Gln Tyr Met Ala Asn Lys Thr Val Asn Tyr Asp Ala Ile Glu
                485                 490                 495

Ser Leu Leu Lys Ala Arg Met Lys Tyr Val Ala Gly Gly Gln Ala Met
                500                 505                 510

Gln Asn Tyr Gln Ile Gly Asn Gly Glu Ile Leu Thr Ser Val Arg Tyr
                515                 520                 525

Gly Lys Gly Ala Leu Lys Gln Ser Asp Lys Gly Asp Ala Thr Thr Arg
                530                 535                 540

Thr Ser Gly Val Gly Val Met Gly Asn Gln Pro Asn Phe Ser Leu
545                 550                 555                 560

Asp Gly Lys Val Val Ala Leu Asn Met Gly Ala Ala His Ala Asn Gln
                565                 570                 575

Glu Tyr Arg Ala Leu Met Val Ser Thr Lys Asp Gly Val Ala Thr Tyr
                580                 585                 590

Ala Thr Asp Ala Asp Ala Ser Lys Ala Gly Leu Val Lys Arg Thr Asp
                595                 600                 605

Glu Asn Gly Tyr Leu Tyr Phe Leu Asn Asp Asp Leu Lys Gly Val Ala
                610                 615                 620

Asn Pro Gln Val Ser Gly Phe Leu Gln Val Trp Val Pro Val Gly Ala
625                 630                 635                 640

Ala Asp Asp Gln Asp Ile Arg Val Ala Ala Ser Asp Thr Ala Ser Thr
                645                 650                 655

Asp Gly Lys Ser Leu His Gln Asp Ala Ala Met Asp Ser Arg Val Met
                660                 665                 670

Phe Glu Gly Phe Ser Asn Phe Gln Ser Phe Ala Thr Lys Glu Glu
                675                 680                 685

Tyr Thr Asn Val Val Ile Ala Asn Asn Val Asp Lys Phe Val Ser Trp
                690                 695                 700

Gly Ile Thr Asp Phe Glu Met Ala Pro Gln Tyr Val Ser Ser Thr Asp
705                 710                 715                 720

Gly Gln Phe Leu Asp Ser Val Ile Gln Asn Gly Tyr Ala Phe Thr Asp
                725                 730                 735

Arg Tyr Asp Leu Gly Met Ser Lys Ala Asn Lys Tyr Gly Thr Ala Asp
                740                 745                 750

Gln Leu Val Lys Ala Ile Lys Ala Leu His Ala Lys Gly Leu Lys Val
                755                 760                 765

Met Ala Asp Trp Val Pro Asp Gln Met Tyr Thr Phe Pro Lys Gln Glu
                770                 775                 780

Val Val Thr Val Thr Arg Thr Asp Lys Phe Gly Lys Pro Ile Ala Gly
785                 790                 795                 800

Ser Gln Ile Asn His Ser Leu Tyr Val Thr Asp Thr Lys Ser Ser Gly
                805                 810                 815

Asp Asp Tyr Gln Ala Lys Tyr Gly Gly Ala Phe Leu Asp Glu Leu Lys
                820                 825                 830
```

```
Glu Lys Tyr Pro Glu Leu Phe Thr Lys Lys Gln Ile Ser Thr Gly Gln
        835                 840                 845

Ala Ile Asp Pro Ser Val Lys Ile Lys Gln Trp Ser Ala Lys Tyr Phe
850                 855                 860

Asn Gly Ser Asn Ile Leu Gly Arg Gly Ala Asp Tyr Val Leu Ser Asp
865                 870                 875                 880

Gln Ala Ser Asn Lys Tyr Leu Asn Val Ser Asp Asp Lys Leu Phe Leu
            885                 890                 895

Pro Lys Thr Leu Leu Gly Gln Val Val Glu Ser Gly Ile Arg Phe Asp
        900                 905                 910

Gly Thr Gly Tyr Val Tyr Asn Ser Ser Thr Thr Gly Glu Lys Val Thr
    915                 920                 925

Asp Ser Phe Ile Thr Glu Ala Gly Asn Leu Tyr Tyr Phe Gly Gln Asp
930                 935                 940

Gly Tyr Met Val Thr Gly Ala Gln Asn Ile Lys Gly Ser Asn Tyr Tyr
945                 950                 955                 960

Phe Leu Ala Asn Gly Ala Ala Leu Arg Asn Thr Val Tyr Thr Asp Ala
            965                 970                 975

Gln Gly Gln Asn His Tyr Tyr Gly Asn Asp Gly Lys Arg Tyr Glu Asn
        980                 985                 990

Gly Tyr Gln Gln Phe Gly Asn Asp Ser Trp Arg Tyr Phe Lys Asn Gly
        995                 1000                1005

Val Met Ala Leu Gly Leu Thr Thr Val Asp Gly His Val Gln Tyr
    1010                1015                1020

Phe Asp Lys Asp Gly Val Gln Ala Lys Asp Lys Ile Ile Val Thr
    1025                1030                1035

Arg Asp Gly Lys Val Arg Tyr Phe Asp Gln His Asn Gly Asn Ala
    1040                1045                1050

Val Thr Asn Thr Phe Val Ala Asp Lys Thr Gly His Trp Tyr Tyr
    1055                1060                1065

Leu Gly Lys Asp Gly Val Ala Val Thr Gly Ala Gln Thr Val Gly
    1070                1075                1080

Lys Gln His Leu Tyr Phe Glu Ala Asn Gly Gln Gln Val Lys Gly
    1085                1090                1095

Asp Phe Val Thr Ala Lys Asp Gly Lys Leu Tyr Phe Tyr Asp Val
    1100                1105                1110

Asp Ser Gly Asp Met Trp Thr Asn Thr Phe Ile Glu Asp Lys Ala
    1115                1120                1125

Gly Asn Trp Phe Tyr Leu Gly Lys Asp Gly Ala Ala Val Thr Gly
    1130                1135                1140

Ala Gln Thr Ile Lys Gly Gln Lys Leu Tyr Phe Lys Ala Asn Gly
    1145                1150                1155

Gln Gln Val Lys Gly Asp Ile Val Lys Asp Ala Asp Gly Lys Ile
    1160                1165                1170

Arg Tyr Tyr Asp Ala Gln Thr Gly Glu Gln Val Phe Asn Lys Ser
    1175                1180                1185

Val Ser Val Asn Gly Lys Thr Tyr Tyr Phe Gly Ser Asp Gly Thr
    1190                1195                1200

Ala Gln Thr Gln Ala Asn Pro Lys Gly Gln Thr Phe Lys Asp Gly
    1205                1210                1215

Ser Gly Val Leu Arg Phe Tyr Asn Leu Glu Gly Gln Tyr Val Ser
    1220                1225                1230
```

Gly Ser Gly Trp Tyr Glu Thr Ala Glu His Glu Trp Val Tyr Val
    1235                1240                1245

Lys Ser Gly Lys Val Leu Thr Gly Ala Gln Thr Ile Gly Asn Gln
    1250                1255                1260

Arg Val Tyr Phe Lys Asp Asn Gly His Gln Val Lys Gly Gln Leu
    1265                1270                1275

Val Thr Gly Asn Asp Gly Lys Leu Arg Tyr Tyr Asp Ala Asn Ser
    1280                1285                1290

Gly Asp Gln Ala Phe Asn Lys Ser Val Thr Val Asn Gly Lys Thr
    1295                1300                1305

Tyr Tyr Phe Gly Ser Asp Gly Thr Ala Gln Thr Gln Ala Asn Pro
    1310                1315                1320

Lys Gly Gln Thr Phe Lys Asp Gly Ser Gly Val Leu Arg Phe Tyr
    1325                1330                1335

Asn Leu Glu Gly Gln Tyr Val Ser Gly Ser Gly Trp Tyr Lys Asn
    1340                1345                1350

Ala Gln Gly Gln Trp Leu Tyr Val Lys Asp Gly Lys Val Leu Thr
    1355                1360                1365

Gly Leu Gln Thr Val Gly Asn Gln Lys Val Tyr Phe Asp Lys Asn
    1370                1375                1380

Gly Ile Gln Ala Lys Gly Lys Ala Val Arg Thr Ser Asp Gly Lys
    1385                1390                1395

Val Arg Tyr Phe Asp Glu Asn Ser Gly Ser Met Ile Thr Asn Gln
    1400                1405                1410

Trp Lys Phe Val Tyr Gly Gln Tyr Tyr Tyr Phe Gly Ser Asp Gly
    1415                1420                1425

Ala Ala Val Tyr Arg Gly Trp Asn
    1430                1435

<210> SEQ ID NO 7
<211> LENGTH: 851
<212> TYPE: PRT
<213> ORGANISM: Artificial sequence
<220> FEATURE:
<223> OTHER INFORMATION: Gtf 1724-T1

<400> SEQUENCE: 7

Met Thr Phe Ala Ala Asn Asn Arg Ala Tyr Ser Thr Ser Ala Glu Asn
1               5                   10                  15

Phe Glu Ala Ile Asp Asn Tyr Leu Thr Ala Asp Ser Trp Tyr Arg Pro
            20                  25                  30

Lys Ser Ile Leu Lys Asp Gly Lys Thr Trp Thr Glu Ser Ser Lys Asp
        35                  40                  45

Asp Phe Arg Pro Leu Leu Met Ala Trp Trp Pro Asp Thr Glu Thr Lys
    50                  55                  60

Arg Asn Tyr Val Asn Tyr Met Asn Lys Val Val Gly Ile Asp Lys Thr
65                  70                  75                  80

Tyr Thr Ala Glu Thr Ser Gln Ala Asp Leu Thr Ala Ala Glu Leu
                85                  90                  95

Val Gln Ala Arg Ile Glu Gln Lys Ile Thr Thr Glu Gln Asn Thr Lys
            100                 105                 110

Trp Leu Arg Glu Ala Ile Ser Ala Phe Val Lys Thr Gln Pro Gln Trp
        115                 120                 125

Asn Gly Glu Ser Glu Lys Pro Tyr Asp Asp His Leu Gln Asn Gly Ala
    130                 135                 140

-continued

Leu Lys Phe Asp Asn Gln Ser Asp Leu Thr Pro Asp Thr Gln Ser Asn
145                 150                 155                 160

Tyr Arg Leu Leu Asn Arg Thr Pro Thr Asn Gln Thr Gly Ser Leu Asp
                165                 170                 175

Ser Arg Phe Thr Tyr Asn Ala Asn Asp Pro Leu Gly Gly Tyr Glu Leu
            180                 185                 190

Leu Leu Ala Asn Asp Val Asp Asn Ser Asn Pro Ile Val Gln Ala Glu
        195                 200                 205

Gln Leu Asn Trp Leu His Tyr Leu Leu Asn Phe Gly Thr Ile Tyr Ala
    210                 215                 220

Lys Asp Ala Asp Ala Asn Phe Asp Ser Ile Arg Val Asp Ala Val Asp
225                 230                 235                 240

Asn Val Asp Ala Asp Leu Leu Gln Ile Ser Ser Asp Tyr Leu Lys Ala
                245                 250                 255

Ala Tyr Gly Ile Asp Lys Asn Asn Lys Asn Ala Asn Asn His Val Ser
            260                 265                 270

Ile Val Glu Ala Trp Ser Asp Asn Asp Thr Pro Tyr Leu His Asp Asp
        275                 280                 285

Gly Asp Asn Leu Met Asn Met Asp Asn Lys Phe Arg Leu Ser Met Leu
    290                 295                 300

Trp Ser Leu Ala Lys Pro Leu Asp Lys Arg Ser Gly Leu Asn Pro Leu
305                 310                 315                 320

Ile His Asn Ser Leu Val Asp Arg Glu Val Asp Asp Arg Glu Val Glu
                325                 330                 335

Thr Val Pro Ser Tyr Ser Phe Ala Arg Ala His Asp Ser Glu Val Gln
            340                 345                 350

Asp Leu Ile Arg Asp Ile Ile Lys Ala Glu Ile Asn Pro Asn Ala Phe
        355                 360                 365

Gly Tyr Ser Phe Thr Gln Asp Glu Ile Asp Gln Ala Phe Lys Ile Tyr
    370                 375                 380

Asn Glu Asp Leu Lys Lys Thr Asp Lys Lys Tyr Thr His Tyr Asn Val
385                 390                 395                 400

Pro Leu Ser Tyr Thr Leu Leu Thr Asn Lys Gly Ser Ile Pro Arg
                405                 410                 415

Val Tyr Tyr Gly Asp Met Phe Thr Asp Asp Gly Gln Tyr Met Ala Asn
            420                 425                 430

Lys Thr Val Asn Tyr Asp Ala Ile Glu Ser Leu Leu Lys Ala Arg Met
        435                 440                 445

Lys Tyr Val Ala Gly Gln Ala Met Gln Asn Tyr Gln Ile Gly Asn
    450                 455                 460

Gly Glu Ile Leu Thr Ser Val Arg Tyr Gly Lys Gly Ala Leu Lys Gln
465                 470                 475                 480

Ser Asp Lys Gly Asp Ala Thr Thr Arg Thr Ser Gly Val Gly Val Val
                485                 490                 495

Met Gly Asn Gln Pro Asn Phe Ser Leu Asp Gly Lys Val Val Ala Leu
            500                 505                 510

Asn Met Gly Ala Ala His Ala Asn Gln Glu Tyr Arg Ala Leu Met Val
        515                 520                 525

Ser Thr Lys Asp Gly Val Ala Thr Tyr Ala Thr Asp Ala Asp Ala Ser
    530                 535                 540

Lys Ala Gly Leu Val Lys Arg Thr Asp Glu Asn Gly Tyr Leu Tyr Phe
545                 550                 555                 560

Leu Asn Asp Asp Leu Lys Gly Val Ala Asn Pro Gln Val Ser Gly Phe

```
                            565                 570                 575

Leu Gln Val Trp Val Pro Val Gly Ala Ala Asp Asp Gln Asp Ile Arg
            580                 585                 590

Val Ala Ala Ser Asp Thr Ala Ser Thr Asp Gly Lys Ser Leu His Gln
            595                 600                 605

Asp Ala Ala Met Asp Ser Arg Val Met Phe Glu Gly Phe Ser Asn Phe
            610                 615                 620

Gln Ser Phe Ala Thr Lys Glu Glu Tyr Thr Asn Val Val Ile Ala
625                 630                 635                 640

Asn Asn Val Asp Lys Phe Val Ser Trp Gly Ile Thr Asp Phe Glu Met
                645                 650                 655

Ala Pro Gln Tyr Val Ser Ser Thr Asp Gly Gln Phe Leu Asp Ser Val
            660                 665                 670

Ile Gln Asn Gly Tyr Ala Phe Thr Asp Arg Tyr Asp Leu Gly Met Ser
            675                 680                 685

Lys Ala Asn Lys Tyr Gly Thr Ala Asp Gln Leu Val Lys Ala Ile Lys
            690                 695                 700

Ala Leu His Ala Lys Gly Leu Lys Val Met Ala Asp Trp Val Pro Asp
705                 710                 715                 720

Gln Met Tyr Thr Phe Pro Lys Gln Glu Val Val Thr Val Thr Arg Thr
                725                 730                 735

Asp Lys Phe Gly Lys Pro Ile Ala Gly Ser Gln Ile Asn His Ser Leu
            740                 745                 750

Tyr Val Thr Asp Thr Lys Ser Ser Gly Asp Asp Tyr Gln Ala Lys Tyr
            755                 760                 765

Gly Gly Ala Phe Leu Asp Glu Leu Lys Glu Lys Tyr Pro Glu Leu Phe
            770                 775                 780

Thr Lys Lys Gln Ile Ser Thr Gly Gln Ala Ile Asp Pro Ser Val Lys
785                 790                 795                 800

Ile Lys Gln Trp Ser Ala Lys Tyr Phe Asn Gly Ser Asn Ile Leu Gly
                805                 810                 815

Arg Gly Ala Asp Tyr Val Leu Ser Asp Gln Ala Ser Asn Lys Tyr Leu
            820                 825                 830

Asn Val Ser Asp Asp Lys Leu Phe Leu Pro Lys Thr Leu Leu Gly Gln
            835                 840                 845

Val Val Glu
    850

<210> SEQ ID NO 8
<211> LENGTH: 905
<212> TYPE: PRT
<213> ORGANISM: Artificial sequence
<220> FEATURE:
<223> OTHER INFORMATION: GtfJ-T1/Gtf 7527-T1

<400> SEQUENCE: 8

Met Gly Phe Ser Ile Asn Asn Arg Ala Tyr Asp Ser Ser Glu Ala Ser
1               5                   10                  15

Phe Glu Leu Ile Asp Gly Tyr Leu Thr Ala Asp Ser Trp Tyr Arg Pro
            20                  25                  30

Ala Ser Ile Ile Lys Asp Gly Val Thr Trp Gln Ala Ser Thr Ala Glu
        35                  40                  45

Asp Phe Arg Pro Leu Leu Met Ala Trp Trp Pro Asn Val Asp Thr Gln
    50                  55                  60

Val Asn Tyr Leu Asn Tyr Met Ser Lys Val Phe Asn Leu Asp Ala Lys
```

```
            65                  70                  75                  80
Tyr Ser Ser Thr Asp Lys Gln Glu Thr Leu Lys Val Ala Ala Lys Asp
                85                  90                  95
Ile Gln Ile Lys Ile Glu Gln Lys Ile Gln Ala Glu Lys Ser Thr Gln
                100                 105                 110
Trp Leu Arg Glu Thr Ile Ser Ala Phe Val Lys Thr Gln Pro Gln Trp
                115                 120                 125
Asn Lys Glu Thr Glu Asn Tyr Ser Lys Gly Gly Glu Asp His Leu
130                 135                 140
Gln Gly Gly Ala Leu Leu Tyr Val Asn Asp Ser Arg Thr Pro Trp Ala
145                 150                 155                 160
Asn Ser Asp Tyr Arg Arg Leu Asn Arg Thr Ala Thr Asn Gln Thr Gly
                165                 170                 175
Thr Ile Asp Lys Ser Ile Leu Asp Glu Gln Ser Asp Pro Asn His Met
                180                 185                 190
Gly Gly Phe Asp Phe Leu Leu Ala Asn Asp Val Asp Leu Ser Asn Pro
                195                 200                 205
Val Val Gln Ala Glu Gln Leu Asn Gln Ile His Tyr Leu Met Asn Trp
        210                 215                 220
Gly Ser Ile Val Met Gly Asp Lys Asp Ala Asn Phe Asp Gly Ile Arg
225                 230                 235                 240
Val Asp Ala Val Asp Asn Val Asp Ala Asp Met Leu Gln Leu Tyr Thr
                245                 250                 255
Asn Tyr Phe Arg Glu Tyr Tyr Gly Val Asn Lys Ser Glu Ala Asn Ala
                260                 265                 270
Leu Ala His Ile Ser Val Leu Glu Ala Trp Ser Leu Asn Asp Asn His
        275                 280                 285
Tyr Asn Asp Lys Thr Asp Gly Ala Ala Leu Ala Met Glu Asn Lys Gln
        290                 295                 300
Arg Leu Ala Leu Leu Phe Ser Leu Ala Lys Pro Ile Lys Glu Arg Thr
305                 310                 315                 320
Pro Ala Val Ser Pro Leu Tyr Asn Asn Thr Phe Asn Thr Thr Gln Arg
                325                 330                 335
Asp Glu Lys Thr Asp Trp Ile Asn Lys Asp Gly Ser Lys Ala Tyr Asn
                340                 345                 350
Glu Asp Gly Thr Val Lys Gln Ser Thr Ile Gly Lys Tyr Asn Glu Lys
                355                 360                 365
Tyr Gly Asp Ala Ser Gly Asn Tyr Val Phe Ile Arg Ala His Asp Asn
        370                 375                 380
Asn Val Gln Asp Ile Ile Ala Glu Ile Ile Lys Lys Glu Ile Asn Pro
385                 390                 395                 400
Lys Ser Asp Gly Phe Thr Ile Thr Asp Ala Glu Met Lys Gln Ala Phe
                405                 410                 415
Glu Ile Tyr Asn Lys Asp Met Leu Ser Ser Asp Lys Lys Tyr Thr Leu
                420                 425                 430
Asn Asn Ile Pro Ala Ala Tyr Ala Val Met Leu Gln Asn Met Glu Thr
                435                 440                 445
Ile Thr Arg Val Tyr Tyr Gly Asp Leu Tyr Thr Asp Asp Gly His Tyr
        450                 455                 460
Met Glu Thr Lys Ser Pro Tyr Tyr Asp Thr Ile Val Asn Leu Met Lys
465                 470                 475                 480
Ser Arg Ile Lys Tyr Val Ser Gly Gly Gln Ala Gln Arg Ser Tyr Trp
                485                 490                 495
```

```
Leu Pro Thr Asp Gly Lys Met Asp Asn Ser Asp Val Glu Leu Tyr Arg
            500                 505                 510
Thr Asn Glu Val Tyr Thr Ser Val Arg Tyr Gly Lys Asp Ile Met Thr
            515                 520                 525
Ala Asn Asp Thr Glu Gly Ser Lys Tyr Ser Arg Thr Ser Gly Gln Val
            530                 535                 540
Thr Leu Val Ala Asn Asn Pro Lys Leu Asn Leu Asp Gln Ser Ala Lys
545                 550                 555                 560
Leu Asn Val Glu Met Gly Lys Ile His Ala Asn Gln Lys Tyr Arg Ala
                565                 570                 575
Leu Ile Val Gly Thr Ala Asp Gly Ile Lys Asn Phe Thr Ser Asp Ala
            580                 585                 590
Asp Ala Ile Ala Ala Gly Tyr Val Lys Glu Thr Asp Ser Asn Gly Val
            595                 600                 605
Leu Thr Phe Gly Ala Asn Asp Ile Lys Gly Tyr Glu Thr Phe Asp Met
            610                 615                 620
Ser Gly Phe Val Ala Val Trp Val Pro Val Gly Ala Ser Asp Asn Gln
625                 630                 635                 640
Asp Ile Arg Val Ala Pro Ser Thr Glu Ala Lys Lys Glu Gly Glu Leu
                645                 650                 655
Thr Leu Lys Ala Thr Glu Ala Tyr Asp Ser Gln Leu Ile Tyr Glu Gly
                660                 665                 670
Phe Ser Asn Phe Gln Thr Ile Pro Asp Gly Ser Asp Pro Ser Val Tyr
            675                 680                 685
Thr Asn Arg Lys Ile Ala Glu Asn Val Asp Leu Phe Lys Ser Trp Gly
            690                 695                 700
Val Thr Ser Phe Glu Met Ala Pro Gln Phe Val Ser Ala Asp Asp Gly
705                 710                 715                 720
Thr Phe Leu Asp Ser Val Ile Gln Asn Gly Tyr Ala Phe Ala Asp Arg
                725                 730                 735
Tyr Asp Leu Ala Met Ser Lys Asn Asn Lys Tyr Gly Ser Lys Glu Asp
                740                 745                 750
Leu Arg Asp Ala Leu Lys Ala Leu His Lys Ala Gly Ile Gln Ala Ile
            755                 760                 765
Ala Asp Trp Val Pro Asp Gln Ile Tyr Gln Leu Pro Gly Lys Glu Val
            770                 775                 780
Val Thr Ala Thr Arg Thr Asp Gly Ala Gly Arg Lys Ile Ala Asp Ala
785                 790                 795                 800
Ile Ile Asp His Ser Leu Tyr Val Ala Asn Ser Lys Ser Ser Gly Lys
                805                 810                 815
Asp Tyr Gln Ala Lys Tyr Gly Gly Glu Phe Leu Ala Glu Leu Lys Ala
            820                 825                 830
Lys Tyr Pro Glu Met Phe Lys Val Asn Met Ile Ser Thr Gly Lys Pro
            835                 840                 845
Ile Asp Asp Ser Val Lys Leu Lys Gln Trp Lys Ala Glu Tyr Phe Asn
850                 855                 860
Gly Thr Asn Val Leu Glu Arg Gly Val Gly Tyr Val Leu Ser Asp Glu
865                 870                 875                 880
Ala Thr Gly Lys Tyr Phe Thr Val Thr Lys Glu Gly Asn Phe Ile Pro
                885                 890                 895
Leu Gln Leu Thr Gly Lys Glu Lys Val
            900                 905
```

<210> SEQ ID NO 9
<211> LENGTH: 1341
<212> TYPE: PRT
<213> ORGANISM: Artificial sequence
<220> FEATURE:
<223> OTHER INFORMATION: Gtf 6855_N-terminally truncated enzyme with added start-methionine.

<400> SEQUENCE: 9

```
Met Ile Asp Gly Lys Tyr Tyr Tyr Val Asn Glu Asp Gly Ser His Lys
1               5                   10                  15

Glu Asn Phe Ala Ile Thr Val Asn Gly Gln Leu Leu Tyr Phe Gly Lys
                20                  25                  30

Asp Gly Ala Leu Thr Ser Ser Thr Tyr Ser Phe Thr Pro Gly Thr
            35                  40                  45

Thr Asn Ile Val Asp Gly Phe Ser Ile Asn Asn Arg Ala Tyr Asp Ser
    50                  55                  60

Ser Glu Ala Ser Phe Glu Leu Ile Asp Gly Tyr Leu Thr Ala Asp Ser
65                  70                  75                  80

Trp Tyr Arg Pro Ala Ser Ile Ile Lys Asp Gly Val Thr Trp Gln Ala
                85                  90                  95

Ser Thr Ala Glu Asp Phe Arg Pro Leu Leu Met Ala Trp Trp Pro Asn
                100                 105                 110

Val Asp Thr Gln Val Asn Tyr Leu Asn Tyr Met Ser Lys Val Phe Asn
                115                 120                 125

Leu Asp Ala Lys Tyr Ser Ser Thr Asp Lys Gln Glu Thr Leu Lys Val
        130                 135                 140

Ala Ala Lys Asp Ile Gln Ile Lys Ile Glu Gln Lys Ile Gln Ala Glu
145                 150                 155                 160

Lys Ser Thr Gln Trp Leu Arg Glu Thr Ile Ser Ala Phe Val Lys Thr
                165                 170                 175

Gln Pro Gln Trp Asn Lys Glu Thr Glu Asn Tyr Ser Lys Gly Gly Gly
                180                 185                 190

Glu Asp His Leu Gln Gly Gly Ala Leu Leu Tyr Val Asn Asp Ser Arg
        195                 200                 205

Thr Pro Trp Ala Asn Ser Asp Tyr Arg Arg Leu Asn Arg Thr Ala Thr
    210                 215                 220

Asn Gln Thr Gly Thr Ile Asp Lys Ser Ile Leu Asp Glu Gln Ser Asp
225                 230                 235                 240

Pro Asn His Met Gly Gly Phe Asp Phe Leu Leu Ala Asn Asp Val Asp
                245                 250                 255

Leu Ser Asn Pro Val Val Gln Ala Glu Gln Leu Asn Gln Ile His Tyr
                260                 265                 270

Leu Met Asn Trp Gly Ser Ile Val Met Gly Asp Lys Asp Ala Asn Phe
        275                 280                 285

Asp Gly Ile Arg Val Asp Ala Val Asp Asn Val Asp Ala Asp Met Leu
    290                 295                 300

Gln Leu Tyr Thr Asn Tyr Phe Arg Glu Tyr Tyr Gly Val Asn Lys Ser
305                 310                 315                 320

Glu Ala Asn Ala Leu Ala His Ile Ser Val Leu Glu Ala Trp Ser Leu
                325                 330                 335

Asn Asp Asn His Tyr Asn Asp Lys Thr Asp Gly Ala Ala Leu Ala Met
                340                 345                 350

Glu Asn Lys Gln Arg Leu Ala Leu Leu Phe Ser Leu Ala Lys Pro Ile
        355                 360                 365
```

-continued

Lys Glu Arg Thr Pro Ala Val Ser Pro Leu Tyr Asn Asn Thr Phe Asn
370                 375                 380

Thr Thr Gln Arg Asp Glu Lys Thr Asp Trp Ile Asn Lys Asp Gly Ser
385                 390                 395                 400

Lys Ala Tyr Asn Glu Asp Gly Thr Val Lys Gln Ser Thr Ile Gly Lys
        405                 410                 415

Tyr Asn Glu Lys Tyr Gly Asp Ala Ser Gly Asn Tyr Val Phe Ile Arg
        420                 425                 430

Ala His Asp Asn Asn Val Gln Asp Ile Ile Ala Glu Ile Ile Lys Lys
        435                 440                 445

Glu Ile Asn Pro Lys Ser Asp Gly Phe Thr Ile Thr Asp Ala Glu Met
450                 455                 460

Lys Gln Ala Phe Glu Ile Tyr Asn Lys Asp Met Leu Ser Ser Asp Lys
465                 470                 475                 480

Lys Tyr Thr Leu Asn Asn Ile Pro Ala Ala Tyr Ala Val Met Leu Gln
        485                 490                 495

Asn Met Glu Thr Ile Thr Arg Val Tyr Tyr Gly Asp Leu Tyr Thr Asp
            500                 505                 510

Asp Gly His Tyr Met Glu Thr Lys Ser Pro Tyr Tyr Asp Thr Ile Val
        515                 520                 525

Asn Leu Met Lys Ser Arg Ile Lys Tyr Val Ser Gly Gly Gln Ala Gln
530                 535                 540

Arg Ser Tyr Trp Leu Pro Thr Asp Gly Lys Met Asp Asn Ser Asp Val
545                 550                 555                 560

Glu Leu Tyr Arg Thr Asn Glu Val Tyr Thr Ser Val Arg Tyr Gly Lys
                565                 570                 575

Asp Ile Met Thr Ala Asn Asp Thr Glu Gly Ser Lys Tyr Ser Arg Thr
            580                 585                 590

Ser Gly Gln Val Thr Leu Val Ala Asn Asn Pro Lys Leu Thr Leu Asp
        595                 600                 605

Gln Ser Ala Lys Leu Asn Val Glu Met Gly Lys Ile His Ala Asn Gln
610                 615                 620

Lys Tyr Arg Ala Leu Ile Val Gly Thr Ala Asp Gly Ile Lys Asn Phe
625                 630                 635                 640

Thr Ser Asp Ala Asp Ala Ile Ala Ala Gly Tyr Val Lys Glu Thr Asp
                645                 650                 655

Ser Asn Gly Val Leu Thr Phe Gly Ala Asn Asp Ile Lys Gly Tyr Glu
            660                 665                 670

Thr Phe Asp Met Ser Gly Phe Val Ala Val Trp Val Pro Val Gly Ala
        675                 680                 685

Ser Asp Asp Gln Asp Ile Arg Val Ala Pro Ser Thr Glu Ala Lys Lys
690                 695                 700

Glu Gly Glu Leu Thr Leu Lys Ala Thr Glu Ala Tyr Asp Ser Gln Leu
705                 710                 715                 720

Ile Tyr Glu Gly Phe Ser Asn Phe Gln Thr Ile Pro Asp Gly Ser Asp
                725                 730                 735

Pro Ser Val Tyr Thr Asn Arg Lys Ile Ala Glu Asn Val Asp Leu Phe
            740                 745                 750

Lys Ser Trp Gly Val Thr Ser Phe Glu Met Ala Pro Gln Phe Val Ser
        755                 760                 765

Ala Asp Asp Gly Thr Phe Leu Asp Ser Val Ile Gln Asn Gly Tyr Ala
770                 775                 780

```
Phe Ala Asp Arg Tyr Asp Leu Ala Met Ser Lys Asn Asn Lys Tyr Gly
785                 790                 795                 800

Ser Lys Glu Asp Leu Arg Asp Ala Leu Lys Ala Leu His Lys Ala Gly
            805                 810                 815

Ile Gln Ala Ile Ala Asp Trp Val Pro Asp Gln Ile Tyr Gln Leu Pro
        820                 825                 830

Gly Lys Glu Val Val Thr Ala Thr Arg Thr Asp Gly Ala Gly Arg Lys
    835                 840                 845

Ile Ala Asp Ala Ile Ile Asp His Ser Leu Tyr Val Ala Asn Thr Lys
850                 855                 860

Ser Ser Gly Lys Asp Tyr Gln Ala Lys Tyr Gly Gly Glu Phe Leu Ala
865                 870                 875                 880

Glu Leu Lys Ala Lys Tyr Pro Glu Met Phe Lys Val Asn Met Ile Ser
            885                 890                 895

Thr Gly Lys Pro Ile Asp Asp Ser Val Lys Leu Lys Gln Trp Lys Ala
        900                 905                 910

Glu Tyr Phe Asn Gly Thr Asn Val Leu Glu Arg Gly Val Gly Tyr Val
    915                 920                 925

Leu Ser Asp Glu Ala Thr Gly Lys Tyr Phe Thr Val Thr Lys Asp Gly
930                 935                 940

Asn Phe Ile Pro Leu Gln Leu Thr Gly Asn Glu Lys Val Val Thr Gly
945                 950                 955                 960

Phe Ser Asn Asp Gly Lys Gly Ile Thr Tyr Phe Gly Thr Ser Gly Thr
            965                 970                 975

Gln Ala Lys Ser Ala Phe Val Thr Phe Asn Gly Asn Thr Tyr Tyr Phe
        980                 985                 990

Asp Ala Arg Gly His Met Val Thr Asn Gly Glu Tyr Ser Pro Asn Gly
    995                 1000                1005

Lys Asp Val Tyr Arg Phe Leu Pro Asn Gly Ile Met Leu Ser Asn
    1010                1015                1020

Ala Phe Tyr Val Asp Ala Asn Gly Asn Thr Tyr Leu Tyr Asn Ser
    1025                1030                1035

Lys Gly Gln Met Tyr Lys Gly Gly Tyr Thr Lys Phe Asp Val Thr
    1040                1045                1050

Glu Thr Asp Lys Asp Gly Lys Glu Ser Lys Val Val Lys Phe Arg
    1055                1060                1065

Tyr Phe Thr Asn Glu Gly Val Met Ala Lys Gly Val Thr Val Ile
    1070                1075                1080

Asp Gly Phe Thr Gln Tyr Phe Gly Glu Asp Gly Phe Gln Ala Lys
    1085                1090                1095

Asp Lys Leu Val Thr Phe Lys Gly Lys Thr Tyr Tyr Phe Asp Ala
    1100                1105                1110

His Thr Gly Asn Ala Ile Lys Asp Thr Trp Arg Asn Ile Asn Gly
    1115                1120                1125

Lys Trp Tyr His Phe Asp Ala Asn Gly Val Ala Ala Thr Gly Ala
    1130                1135                1140

Gln Val Ile Asn Gly Gln Lys Leu Tyr Phe Asn Glu Asp Gly Ser
    1145                1150                1155

Gln Val Lys Gly Gly Val Val Lys Asn Ala Asp Gly Thr Tyr Ser
    1160                1165                1170

Lys Tyr Lys Glu Gly Ser Gly Glu Leu Val Thr Asn Glu Phe Phe
    1175                1180                1185

Thr Thr Asp Gly Asn Val Trp Tyr Tyr Ala Gly Ala Asn Gly Lys
```

Thr Val Thr Gly Ala Gln Val Ile Asn Gly Gln His Leu Tyr Phe
1205                1210                1215

Asn Ala Asp Gly Ser Gln Val Lys Gly Gly Val Val Lys Asn Ala
1220                1225                1230

Asp Gly Thr Tyr Ser Lys Tyr Asp Ala Ser Thr Gly Glu Arg Leu
1235                1240                1245

Thr Asn Glu Phe Phe Thr Thr Gly Asp Asn Asn Trp Tyr Tyr Ile
1250                1255                1260

Gly Ala Asn Gly Lys Ser Val Thr Gly Glu Val Lys Ile Gly Asp
1265                1270                1275

Asp Thr Tyr Phe Phe Ala Lys Asp Gly Lys Gln Val Lys Gly Gln
1280                1285                1290

Thr Val Ser Ala Gly Asn Gly Arg Ile Ser Tyr Tyr Tyr Gly Asp
1295                1300                1305

Ser Gly Lys Arg Ala Val Ser Thr Trp Ile Glu Ile Gln Pro Gly
1310                1315                1320

Val Tyr Val Tyr Phe Asp Lys Asn Gly Ile Ala Tyr Pro Pro Arg
1325                1330                1335

Val Leu Asn
1340

<210> SEQ ID NO 10
<211> LENGTH: 1323
<212> TYPE: PRT
<213> ORGANISM: Artificial sequence
<220> FEATURE:
<223> OTHER INFORMATION: Gtf 5926_N-terminally truncated enzyme with
      added start-methionine.

<400> SEQUENCE: 10

Met Val Asp Gly Lys Tyr Tyr Tyr Asp Ala Asp Gly Asn Val Lys
1               5                   10                  15

Lys Asn Phe Ala Val Ser Val Gly Asp Ala Ile Phe Tyr Phe Asp Glu
                20                  25                  30

Thr Gly Ala Tyr Lys Asp Thr Ser Lys Val Asp Ala Asp Lys Thr Ser
            35                  40                  45

Ser Ser Val Asn Gln Thr Thr Glu Thr Phe Ala Ala Asn Asn Arg Ala
50                  55                  60

Tyr Ser Thr Ala Ala Glu Asn Phe Glu Ala Ile Asp Asn Tyr Leu Thr
65                  70                  75                  80

Ala Asp Ser Trp Tyr Arg Pro Lys Ser Ile Leu Lys Asp Gly Thr Thr
                85                  90                  95

Trp Thr Glu Ser Thr Lys Asp Asp Phe Arg Pro Leu Leu Met Ala Trp
            100                 105                 110

Trp Pro Asp Thr Glu Thr Lys Arg Asn Tyr Val Asn Tyr Met Asn Lys
        115                 120                 125

Val Val Gly Ile Asp Lys Thr Tyr Thr Ala Glu Thr Ser Gln Ala Asp
    130                 135                 140

Leu Thr Ala Ala Glu Leu Val Gln Ala Arg Ile Glu Gln Lys Ile
145                 150                 155                 160

Thr Ser Glu Lys Asn Thr Lys Trp Leu Arg Glu Ala Ile Ser Ala Phe
                165                 170                 175

Val Lys Thr Gln Pro Gln Trp Asn Gly Glu Ser Glu Lys Pro Tyr Asp
            180                 185                 190

```
Asp His Leu Gln Asn Gly Ala Leu Lys Phe Asp Asn Glu Thr Ser Leu
            195                 200                 205
Thr Pro Asp Thr Gln Ser Gly Tyr Arg Ile Leu Asn Arg Thr Pro Thr
210                 215                 220
Asn Gln Thr Gly Ser Leu Asp Pro Arg Phe Thr Phe Asn Gln Asn Asp
225                 230                 235                 240
Pro Leu Gly Gly Tyr Glu Tyr Leu Leu Ala Asn Asp Val Asp Asn Ser
                245                 250                 255
Asn Pro Val Val Gln Ala Glu Ser Leu Asn Trp Leu His Tyr Leu Leu
            260                 265                 270
Asn Phe Gly Ser Ile Tyr Ala Asn Asp Pro Glu Ala Asn Phe Asp Ser
        275                 280                 285
Ile Arg Val Asp Ala Val Asp Asn Val Asp Ala Asp Leu Leu Gln Ile
    290                 295                 300
Ser Ser Asp Tyr Leu Lys Ser Ala Tyr Lys Ile Asp Lys Asn Asn Lys
305                 310                 315                 320
Asn Ala Asn Asp His Val Ser Ile Val Glu Ala Trp Ser Asp Asn Asp
                325                 330                 335
Thr Pro Tyr Leu Asn Asp Asp Gly Asp Asn Leu Met Asn Met Asp Asn
            340                 345                 350
Lys Phe Arg Leu Ser Met Leu Trp Ser Leu Ala Lys Pro Thr Asn Val
        355                 360                 365
Arg Ser Gly Leu Asn Pro Leu Ile His Asn Ser Val Val Asp Arg Glu
    370                 375                 380
Val Asp Asp Arg Glu Val Glu Ala Thr Pro Asn Tyr Ser Phe Ala Arg
385                 390                 395                 400
Ala His Asp Ser Glu Val Gln Asp Leu Ile Arg Asp Ile Ile Lys Ala
                405                 410                 415
Glu Ile Asn Pro Asn Ser Phe Gly Tyr Ser Phe Thr Gln Glu Glu Ile
            420                 425                 430
Asp Gln Ala Phe Lys Ile Tyr Asn Glu Asp Leu Lys Lys Thr Asn Lys
        435                 440                 445
Lys Tyr Thr His Tyr Asn Val Pro Leu Ser Tyr Thr Leu Leu Leu Thr
    450                 455                 460
Asn Lys Gly Ser Ile Pro Arg Ile Tyr Tyr Gly Asp Met Phe Thr Asp
465                 470                 475                 480
Asp Gly Gln Tyr Met Ala Asn Lys Thr Val Asn Tyr Asp Ala Ile Glu
                485                 490                 495
Ser Leu Leu Lys Ala Arg Met Lys Tyr Val Ser Gly Gly Gln Ala Met
            500                 505                 510
Gln Asn Tyr Asn Ile Gly Asn Gly Glu Ile Leu Thr Ser Val Arg Tyr
        515                 520                 525
Gly Lys Gly Ala Leu Lys Gln Ser Asp Lys Gly Asp Lys Thr Thr Arg
    530                 535                 540
Thr Ser Gly Ile Gly Val Val Met Gly Asn Gln Ser Asn Phe Ser Leu
545                 550                 555                 560
Glu Gly Lys Val Val Ala Leu Asn Met Gly Ala Thr His Thr Lys Gln
                565                 570                 575
Lys Tyr Arg Ala Leu Met Val Ser Thr Glu Thr Gly Val Ala Ile Tyr
            580                 585                 590
Asn Ser Asp Glu Glu Ala Glu Ala Ala Gly Leu Ile Lys Thr Thr Asp
        595                 600                 605
Glu Asn Gly Tyr Leu Tyr Phe Leu Asn Asp Asp Leu Lys Gly Val Ala
```

```
              610                 615                 620
Asn Pro Gln Val Ser Gly Phe Leu Gln Val Trp Val Pro Val Gly Ala
625                 630                 635                 640

Pro Ala Asp Gln Asp Ile Arg Val Ala Ala Thr Asp Ala Ala Ser Thr
                645                 650                 655

Asp Gly Lys Ser Leu His Gln Asp Ala Ala Leu Asp Ser Arg Val Met
                660                 665                 670

Phe Glu Gly Phe Ser Asn Phe Gln Ser Phe Ala Thr Lys Glu Glu Glu
                675                 680                 685

Tyr Thr Asn Val Val Ile Ala Lys Asn Val Asp Lys Phe Val Ser Trp
                690                 695                 700

Gly Ile Thr Asp Phe Glu Met Ala Pro Gln Tyr Val Ser Ser Thr Asp
705                 710                 715                 720

Gly Thr Phe Leu Asp Ser Val Ile Gln Asn Gly Tyr Ala Phe Thr Asp
                725                 730                 735

Arg Tyr Asp Leu Gly Met Ser Lys Ala Asn Lys Tyr Gly Thr Ala Asp
                740                 745                 750

Gln Leu Val Ala Ala Ile Lys Ala Leu His Ala Lys Gly Leu Arg Val
                755                 760                 765

Met Ala Asp Trp Val Pro Asp Gln Met Tyr Thr Phe Pro Lys Lys Glu
770                 775                 780

Val Val Thr Val Thr Arg Thr Asp Lys Phe Gly Asn Pro Val Ala Gly
785                 790                 795                 800

Ser Gln Ile Asn His Thr Leu Tyr Val Thr Asp Thr Lys Gly Ser Gly
                805                 810                 815

Asp Asp Tyr Gln Ala Lys Tyr Gly Gly Ala Phe Leu Asp Glu Leu Lys
                820                 825                 830

Glu Lys Tyr Pro Glu Leu Phe Thr Lys Lys Gln Ile Ser Thr Gly Gln
                835                 840                 845

Ala Ile Asp Pro Ser Val Lys Ile Lys Gln Trp Ser Ala Lys Tyr Phe
                850                 855                 860

Asn Gly Ser Asn Ile Leu Gly Arg Gly Ala Asn Tyr Val Leu Ser Asp
865                 870                 875                 880

Gln Ala Ser Asn Lys Tyr Phe Asn Val Ala Glu Gly Lys Val Phe Leu
                885                 890                 895

Pro Ala Ala Met Leu Gly Lys Val Val Glu Ser Gly Ile Arg Phe Asp
                900                 905                 910

Gly Lys Gly Tyr Ile Tyr Asn Ser Ser Thr Thr Gly Glu Gln Val Lys
                915                 920                 925

Asp Ser Phe Ile Thr Glu Ala Gly Asn Leu Tyr Tyr Phe Gly Lys Asp
930                 935                 940

Gly Tyr Met Val Met Gly Ala Gln Asn Ile Gln Gly Ala Asn Tyr Tyr
945                 950                 955                 960

Phe Leu Ala Asn Gly Ala Ala Leu Arg Asn Ser Ile Leu Thr Asp Gln
                965                 970                 975

Asp Gly Lys Ser His Tyr Tyr Ala Asn Asp Gly Lys Arg Tyr Glu Asn
                980                 985                 990

Gly Tyr Tyr Gln Phe Gly Asn Asp Ser Trp Arg Tyr Phe Glu Asn Gly
                995                1000                1005

Val Met Ala Val Gly Leu Thr Arg Val Ala Gly His Asp Gln Tyr
                1010                1015                1020

Phe Asp Lys Asp Gly Ile Gln Ala Lys Asn Lys Ile Ile Val Thr
                1025                1030                1035
```

```
Arg Asp Gly Lys Val Arg Tyr Phe Asp Glu His Asn Gly Asn Ala
    1040            1045                1050

Ala Thr Asn Thr Phe Ile Ser Asp Gln Ala Gly His Trp Tyr Tyr
    1055            1060                1065

Leu Gly Lys Asp Gly Val Ala Val Thr Gly Ala Gln Thr Val Gly
    1070            1075                1080

Lys Gln His Leu Tyr Phe Glu Ala Asn Gly Gln Gln Val Lys Gly
    1085            1090                1095

Asp Phe Val Thr Ala Lys Asp Gly Lys Leu Tyr Phe Leu Asp Gly
    1100            1105                1110

Asp Ser Gly Asp Met Trp Thr Asp Thr Phe Val Gln Asp Lys Ala
    1115            1120                1125

Gly His Trp Phe Tyr Leu Gly Lys Asp Gly Ala Ala Val Thr Gly
    1130            1135                1140

Ala Gln Thr Val Arg Gly Gln Lys Leu Tyr Phe Lys Ala Asn Gly
    1145            1150                1155

Gln Gln Val Lys Gly Asp Ile Val Lys Gly Ala Asp Gly Lys Ile
    1160            1165                1170

Arg Tyr Tyr Asp Ala Asn Ser Gly Asp Gln Val Tyr Asn Arg Thr
    1175            1180                1185

Val Lys Gly Ser Asp Gly Lys Thr Tyr Ile Ile Gly Asn Asp Gly
    1190            1195                1200

Val Ala Ile Thr Gln Thr Ile Ala Lys Gly Gln Thr Ile Lys Asp
    1205            1210                1215

Gly Ser Val Leu Arg Phe Tyr Ser Met Glu Gly Gln Leu Val Thr
    1220            1225                1230

Gly Ser Gly Trp Tyr Ser Asn Ala Lys Gly Gln Trp Leu Tyr Val
    1235            1240                1245

Lys Asn Gly Gln Val Leu Thr Gly Leu Gln Thr Val Gly Ser Gln
    1250            1255                1260

Arg Val Tyr Phe Asp Ala Asn Gly Ile Gln Ala Lys Gly Lys Ala
    1265            1270                1275

Val Arg Thr Ser Asp Gly Lys Leu Arg Tyr Phe Asp Ala Asn Ser
    1280            1285                1290

Gly Ser Met Ile Thr Asn Gln Trp Lys Glu Val Asn Gly Gln Tyr
    1295            1300                1305

Tyr Tyr Phe Asp Asn Asn Gly Val Ala Ile Tyr Arg Gly Trp Asn
    1310            1315                1320

<210> SEQ ID NO 11
<211> LENGTH: 1340
<212> TYPE: PRT
<213> ORGANISM: Artificial sequence
<220> FEATURE:
<223> OTHER INFORMATION: Gtf 2765_N-terminally truncated enzyme with
      added start-methionine.

<400> SEQUENCE: 11

Met Ile Asp Gly Lys Tyr Tyr Tyr Val Asn Glu Asp Gly Ser His Lys
1               5                   10                  15

Glu Asn Phe Ala Ile Thr Val Asn Gly Gln Leu Leu Tyr Phe Gly Lys
                20                  25                  30

Asp Gly Ala Leu Thr Ser Ser Ser Thr Tyr Ser Phe Thr Gln Gly Thr
            35                  40                  45

Thr Asn Ile Val Asp Gly Phe Ser Ile Asn Asn Arg Ala Tyr Asp Ser
```

```
                50                  55                  60
Ser Glu Ala Ser Phe Glu Leu Ile Asp Gly Tyr Leu Thr Ala Asp Ser
65                  70                  75                  80

Trp Tyr Arg Pro Ala Ser Ile Ile Lys Asp Gly Val Thr Trp Gln Ala
                85                  90                  95

Ser Thr Ala Glu Asp Phe Arg Pro Leu Leu Met Ala Trp Trp Pro Asn
                100                 105                 110

Val Asp Thr Gln Val Asn Tyr Leu Asn Tyr Met Ser Lys Val Phe Asn
                115                 120                 125

Leu Asp Ala Lys Tyr Ser Ser Thr Asp Lys Gln Glu Thr Leu Lys Val
                130                 135                 140

Ala Ala Lys Asp Ile Gln Ile Lys Ile Glu Gln Lys Ile Gln Ala Glu
145                 150                 155                 160

Lys Ser Thr Gln Trp Leu Arg Glu Thr Ile Ser Ala Phe Val Lys Thr
                165                 170                 175

Gln Pro Gln Trp Asn Lys Glu Thr Glu Asn Tyr Ser Lys Gly Gly Gly
                180                 185                 190

Glu Asp His Leu Gln Gly Gly Ala Leu Leu Tyr Val Asn Asp Ser Arg
                195                 200                 205

Thr Pro Trp Ala Asn Ser Asn Tyr Arg Leu Leu Asn Arg Thr Ala Thr
                210                 215                 220

Asn Gln Thr Gly Thr Ile Asp Lys Ser Ile Leu Asp Glu Gln Ser Asp
225                 230                 235                 240

Pro Asn His Met Gly Gly Phe Asp Phe Leu Leu Ala Asn Asp Val Asp
                245                 250                 255

Leu Ser Asn Pro Val Val Gln Ala Glu Gln Leu Asn Gln Ile His Tyr
                260                 265                 270

Leu Met Asn Trp Gly Ser Ile Val Met Gly Asp Lys Asp Ala Asn Phe
                275                 280                 285

Asp Gly Ile Arg Val Asp Ala Val Asp Asn Val Asp Ala Asp Met Leu
                290                 295                 300

Gln Leu Tyr Thr Asn Tyr Phe Arg Glu Tyr Tyr Gly Val Asn Lys Ser
305                 310                 315                 320

Glu Ala Asn Ala Leu Ala His Ile Ser Val Leu Glu Ala Trp Ser Leu
                325                 330                 335

Asn Asp Asn His Tyr Asn Asp Lys Thr Asp Val Ala Ala Leu Ala Met
                340                 345                 350

Glu Asn Lys Gln Arg Leu Ala Leu Leu Phe Ser Leu Ala Lys Pro Ile
                355                 360                 365

Lys Glu Arg Thr Pro Ala Val Ser Pro Leu Tyr Asn Asn Thr Phe Asn
                370                 375                 380

Thr Thr Gln Arg Asp Glu Lys Thr Asp Trp Ile Asn Lys Asp Gly Ser
385                 390                 395                 400

Lys Ala Tyr Asn Glu Asp Gly Thr Val Lys Lys Ser Thr Ile Gly Lys
                405                 410                 415

Tyr Asn Glu Lys Tyr Gly Asp Ala Ser Gly Asn Tyr Val Phe Ile Arg
                420                 425                 430

Ala His Asp Asn Val Gln Asp Ile Ile Ala Glu Ile Ile Lys Lys
                435                 440                 445

Glu Ile Asn Glu Lys Ser Asp Gly Phe Thr Ile Thr Asp Ser Glu Met
450                 455                 460

Lys Arg Ala Phe Glu Ile Tyr Asn Lys Asp Met Leu Ser Asn Asp Lys
465                 470                 475                 480
```

```
Lys Tyr Thr Leu Asn Asn Ile Pro Ala Ala Tyr Ala Val Met Leu Gln
            485                 490                 495
Asn Met Glu Thr Ile Thr Arg Val Tyr Tyr Gly Asp Leu Tyr Thr Asp
        500                 505                 510
Asp Gly Asn Tyr Met Glu Ala Lys Ser Pro Tyr Asp Thr Ile Val
        515                 520                 525
Asn Leu Met Lys Ser Arg Ile Lys Tyr Val Ser Gly Gln Ala Gln
    530                 535                 540
Arg Ser Tyr Trp Leu Pro Thr Asp Gly Lys Met Asp Lys Ser Asp Val
545                 550                 555                 560
Glu Leu Tyr Arg Thr Asn Glu Val Tyr Thr Ser Val Arg Tyr Gly Lys
                565                 570                 575
Asp Ile Met Thr Ala Asp Asp Thr Gln Gly Ser Lys Tyr Ser Arg Thr
            580                 585                 590
Ser Gly Gln Val Thr Leu Val Val Asn Asn Pro Lys Leu Thr Leu Asp
        595                 600                 605
Gln Ser Ala Lys Leu Asn Val Val Met Gly Lys Ile His Ala Asn Gln
    610                 615                 620
Lys Tyr Arg Ala Leu Ile Val Gly Thr Pro Asn Gly Ile Lys Asn Phe
625                 630                 635                 640
Thr Ser Asp Ala Glu Ala Ile Ala Ala Gly Tyr Val Lys Glu Thr Asp
                645                 650                 655
Gly Asn Gly Val Leu Thr Phe Gly Ala Asn Asp Ile Lys Gly Tyr Glu
            660                 665                 670
Thr Phe Asp Met Ser Gly Phe Val Ala Val Trp Val Pro Val Gly Ala
        675                 680                 685
Ser Asp Asp Gln Asp Ile Arg Val Ala Ala Ser Thr Ala Ala Lys Lys
    690                 695                 700
Glu Gly Glu Leu Thr Leu Lys Ala Thr Glu Ala Tyr Asp Ser Gln Leu
705                 710                 715                 720
Ile Tyr Glu Gly Phe Ser Asn Phe Gln Thr Ile Pro Asp Gly Ser Asp
                725                 730                 735
Pro Ser Val Tyr Thr Asn Arg Lys Ile Ala Glu Asn Val Asp Leu Phe
            740                 745                 750
Lys Ser Trp Gly Val Thr Ser Phe Glu Met Ala Pro Gln Phe Val Ser
        755                 760                 765
Ala Asp Asp Gly Thr Phe Leu Asp Ser Val Ile Gln Asn Gly Tyr Ala
    770                 775                 780
Phe Ala Asp Arg Tyr Asp Leu Ala Met Ser Lys Asn Asn Lys Tyr Gly
785                 790                 795                 800
Ser Lys Glu Asp Leu Arg Asn Ala Leu Lys Ala Leu His Lys Ala Gly
                805                 810                 815
Ile Gln Ala Ile Ala Asp Trp Val Pro Asp Gln Ile Tyr Gln Leu Pro
            820                 825                 830
Gly Lys Glu Val Val Thr Ala Thr Arg Thr Asp Gly Ala Gly Arg Lys
        835                 840                 845
Ile Ser Asp Ala Ile Asp His Ser Leu Tyr Val Ala Asn Ser Lys
    850                 855                 860
Ser Ser Gly Lys Asp Tyr Gln Ala Lys Tyr Gly Gly Glu Phe Leu Ala
865                 870                 875                 880
Glu Leu Lys Ala Lys Tyr Pro Glu Met Phe Lys Val Asn Met Ile Ser
                885                 890                 895
```

```
Thr Gly Lys Pro Ile Asp Asp Ser Val Lys Leu Lys Gln Trp Lys Ala
            900                 905                 910

Glu Tyr Phe Asn Gly Thr Asn Val Leu Asp Arg Gly Val Gly Tyr Val
        915                 920                 925

Leu Ser Asp Glu Ala Thr Gly Lys Tyr Phe Thr Val Thr Lys Glu Gly
    930                 935                 940

Asn Phe Ile Pro Leu Gln Leu Lys Gly Asn Lys Lys Val Ile Thr Gly
945                 950                 955                 960

Phe Ser Ser Asp Gly Lys Gly Ile Thr Tyr Phe Gly Thr Ser Gly Asn
                965                 970                 975

Gln Ala Lys Ser Ala Phe Val Thr Phe Asn Gly Asn Thr Tyr Tyr Phe
            980                 985                 990

Asp Ala Arg Gly His Met Val Thr Asn Gly Glu Tyr Ser Pro Asn Gly
        995                 1000                1005

Lys Asp Val Tyr Arg Phe Leu Pro Asn Gly Ile Met Leu Ser Asn
    1010                1015                1020

Ala Phe Tyr Val Asp Gly Asn Gly Asn Thr Tyr Leu Tyr Asn Ser
    1025                1030                1035

Lys Gly Gln Met Tyr Lys Gly Gly Tyr Ser Lys Phe Asp Val Thr
    1040                1045                1050

Glu Thr Lys Asp Gly Lys Glu Ser Lys Val Val Lys Phe Arg Tyr
    1055                1060                1065

Phe Thr Asn Glu Gly Val Met Ala Lys Gly Val Thr Val Val Asp
    1070                1075                1080

Gly Phe Thr Gln Tyr Phe Asn Glu Asp Gly Ile Gln Ser Lys Asp
    1085                1090                1095

Glu Leu Val Thr Tyr Asn Gly Lys Thr Tyr Tyr Phe Glu Ala His
    1100                1105                1110

Thr Gly Asn Ala Ile Lys Asn Thr Trp Arg Asn Ile Lys Gly Lys
    1115                1120                1125

Trp Tyr His Phe Asp Ala Asn Gly Val Ala Ala Thr Gly Ala Gln
    1130                1135                1140

Val Ile Asn Gly Gln His Leu Tyr Phe Asn Glu Asp Gly Ser Gln
    1145                1150                1155

Val Lys Gly Ser Ile Val Lys Asn Ala Asp Gly Thr Phe Ser Lys
    1160                1165                1170

Tyr Lys Asp Ser Ser Gly Asp Leu Val Val Asn Glu Phe Phe Thr
    1175                1180                1185

Thr Gly Asp Asn Val Trp Tyr Tyr Ala Gly Ala Asn Gly Lys Thr
    1190                1195                1200

Val Thr Gly Ala Gln Val Ile Asn Gly Gln His Leu Phe Phe Lys
    1205                1210                1215

Glu Asp Gly Ser Gln Val Lys Gly Asp Phe Val Lys Asn Ser Asp
    1220                1225                1230

Gly Thr Tyr Ser Lys Tyr Asp Ala Ala Ser Gly Glu Arg Leu Thr
    1235                1240                1245

Asn Glu Phe Phe Thr Thr Gly Asp Asn His Trp Tyr Tyr Ile Gly
    1250                1255                1260

Ala Asn Gly Lys Thr Val Thr Gly Glu Val Lys Ile Gly Asp Asp
    1265                1270                1275

Thr Tyr Phe Phe Ala Lys Asp Gly Lys Gln Leu Lys Gly Gln Ile
    1280                1285                1290

Val Thr Thr Arg Ser Gly Arg Ile Ser Tyr Tyr Phe Gly Asp Ser
```

```
            1295                1300                1305
Gly Lys Lys Ala Ile Ser Thr Trp Val Glu Ile Gln Pro Gly Val
    1310                1315                1320

Phe Val Phe Phe Asp Lys Asn Gly Leu Ala Tyr Pro Pro Glu Asn
    1325                1330                1335

Met Asn
    1340

<210> SEQ ID NO 12
<211> LENGTH: 1435
<212> TYPE: PRT
<213> ORGANISM: Artificial sequence
<220> FEATURE:
<223> OTHER INFORMATION: Gtf 0427_N-terminally truncated enzyme with
      added start-methionine.

<400> SEQUENCE: 12

Met Val Asp Gly Lys Tyr Tyr Tyr Asp Gln Asp Gly Asn Val Lys
1               5                   10                  15

Lys Asn Phe Ala Val Ser Val Gly Asp Lys Ile Tyr Tyr Phe Asp Glu
                20                  25                  30

Thr Gly Ala Tyr Lys Asp Thr Ser Lys Val Asp Ala Asp Lys Ser Ser
            35                  40                  45

Ser Ala Val Ser Gln Asn Ala Thr Ile Phe Ala Ala Asn Asn Arg Ala
50                  55                  60

Tyr Ser Thr Ser Ala Glu Asn Phe Glu Ala Val Asp Asn Tyr Leu Thr
65                  70                  75                  80

Ala Asp Ser Trp Tyr Arg Pro Lys Ser Ile Leu Lys Asp Gly Lys Thr
                85                  90                  95

Trp Thr Glu Ser Gly Lys Asp Asp Phe Arg Pro Leu Leu Met Ala Trp
            100                 105                 110

Trp Pro Asp Thr Glu Thr Lys Arg Asn Tyr Val Asn Tyr Met Asn Leu
        115                 120                 125

Val Val Gly Ile Asp Lys Thr Tyr Thr Ala Glu Thr Ser Gln Ala Asp
    130                 135                 140

Leu Thr Ala Ala Ala Glu Leu Val Gln Ala Arg Ile Glu Gln Lys Ile
145                 150                 155                 160

Thr Thr Glu Gln Asn Thr Lys Trp Leu Arg Glu Ala Ile Ser Ala Phe
                165                 170                 175

Val Lys Thr Gln Pro Gln Trp Asn Gly Glu Ser Glu Lys Pro Tyr Asp
            180                 185                 190

Asp His Leu Gln Asn Gly Ala Leu Lys Phe Asp Asn Gln Ser Asp Leu
        195                 200                 205

Thr Pro Asp Thr Gln Ser Asn Tyr Arg Leu Leu Asn Arg Thr Pro Thr
    210                 215                 220

Asn Gln Thr Gly Ser Leu Asp Ser Arg Phe Thr Tyr Asn Ala Asn Asp
225                 230                 235                 240

Pro Leu Gly Gly Tyr Glu Phe Leu Leu Ala Asn Asp Val Asp Asn Ser
                245                 250                 255

Asn Pro Val Val Gln Ala Glu Gln Leu Asn Trp Leu His Tyr Leu Leu
            260                 265                 270

Asn Phe Gly Ser Ile Tyr Ala Lys Asp Ala Asp Ala Asn Phe Asp Ser
        275                 280                 285

Ile Arg Val Asp Ala Val Asp Asn Val Asp Ala Asp Leu Leu Gln Ile
    290                 295                 300
```

-continued

```
Ser Ser Asp Tyr Leu Lys Ala Ala Tyr Gly Ile Asp Lys Asn Asn Lys
305                 310                 315                 320

Asn Ala Asn Asn His Val Ser Ile Val Glu Ala Trp Ser Asp Asn Asp
                325                 330                 335

Thr Pro Tyr Leu His Asp Asp Gly Asp Asn Leu Met Asn Met Asp Asn
                340                 345                 350

Lys Phe Arg Leu Ser Met Leu Trp Ser Leu Ala Lys Pro Leu Asp Lys
            355                 360                 365

Arg Ser Gly Leu Asn Pro Leu Ile His Asn Ser Leu Val Asp Arg Glu
        370                 375                 380

Val Asp Asp Arg Glu Val Glu Thr Val Pro Ser Tyr Ser Phe Ala Arg
385                 390                 395                 400

Ala His Asp Ser Glu Val Gln Asp Ile Ile Arg Asp Ile Ile Lys Ala
                405                 410                 415

Glu Ile Asn Pro Asn Ser Phe Gly Tyr Ser Phe Thr Gln Glu Glu Ile
                420                 425                 430

Asp Gln Ala Phe Lys Ile Tyr Asn Glu Asp Leu Lys Lys Thr Asp Lys
            435                 440                 445

Lys Tyr Thr His Tyr Asn Val Pro Leu Ser Tyr Thr Leu Leu Leu Thr
        450                 455                 460

Asn Lys Gly Ser Ile Pro Arg Val Tyr Tyr Gly Asp Met Phe Thr Asp
465                 470                 475                 480

Asp Gly Gln Tyr Met Ala Asn Lys Thr Val Asn Tyr Asp Ala Ile Glu
                485                 490                 495

Ser Leu Leu Lys Ala Arg Met Lys Tyr Val Ser Gly Gly Gln Ala Met
            500                 505                 510

Gln Asn Tyr Gln Ile Gly Asn Gly Glu Ile Leu Thr Ser Val Arg Tyr
        515                 520                 525

Gly Lys Gly Ala Leu Lys Gln Ser Asp Lys Gly Asp Ala Thr Thr Arg
    530                 535                 540

Thr Ser Gly Val Gly Val Val Met Gly Asn Gln Pro Asn Phe Ser Leu
545                 550                 555                 560

Asp Gly Lys Val Val Ala Leu Asn Met Gly Ala Ala His Ala Asn Gln
                565                 570                 575

Glu Tyr Arg Ala Leu Met Val Ser Thr Lys Asp Gly Val Ala Thr Tyr
            580                 585                 590

Ala Thr Asp Ala Asp Ala Ser Lys Ala Gly Leu Val Lys Arg Thr Asp
        595                 600                 605

Glu Asn Gly Tyr Leu Tyr Phe Leu Asn Asp Asp Leu Lys Gly Val Ala
    610                 615                 620

Asn Pro Gln Val Ser Gly Phe Leu Gln Val Trp Val Pro Val Gly Ala
625                 630                 635                 640

Ala Asp Asp Gln Asp Ile Arg Val Ala Ala Ser Asp Thr Ala Ser Thr
                645                 650                 655

Asp Gly Lys Ser Leu His Gln Asp Ala Ala Met Asp Ser Arg Val Met
            660                 665                 670

Phe Glu Gly Phe Ser Asn Phe Gln Ser Phe Ala Thr Lys Glu Glu Glu
        675                 680                 685

Tyr Thr Asn Val Val Ile Ala Asn Asn Val Asp Lys Phe Val Ser Trp
    690                 695                 700

Gly Ile Thr Asp Phe Glu Met Ala Pro Gln Tyr Val Ser Ser Thr Asp
705                 710                 715                 720

Gly Gln Phe Leu Asp Ser Val Ile Gln Asn Gly Tyr Ala Phe Thr Asp
```

```
                725                 730                 735
Arg Tyr Asp Leu Gly Met Ser Lys Ala Asn Lys Tyr Gly Thr Ala Asp
            740                 745                 750
Gln Leu Val Lys Ala Ile Lys Ala Leu His Ala Lys Gly Leu Lys Val
            755                 760                 765
Met Ala Asp Trp Val Pro Asp Gln Met Tyr Thr Phe Pro Lys Gln Glu
770                 775                 780
Val Val Thr Val Thr Arg Thr Asp Lys Phe Gly Lys Pro Ile Ala Gly
785                 790                 795                 800
Ser Gln Ile Asn His Ser Leu Tyr Val Thr Asp Thr Lys Ser Ser Gly
                805                 810                 815
Asp Asp Tyr Gln Ala Lys Tyr Gly Gly Ala Phe Leu Asp Glu Leu Lys
            820                 825                 830
Glu Lys Tyr Pro Glu Leu Phe Thr Lys Lys Gln Ile Ser Thr Gly Gln
            835                 840                 845
Ala Ile Asp Pro Ser Val Lys Ile Lys Gln Trp Ser Ala Lys Tyr Phe
850                 855                 860
Asn Gly Ser Asn Ile Leu Gly Arg Gly Ala Asp Tyr Val Leu Ser Asp
865                 870                 875                 880
Gln Val Ser Asn Lys Tyr Phe Asn Val Ala Ser Asp Thr Leu Phe Leu
                885                 890                 895
Pro Ser Ser Leu Leu Gly Lys Val Val Glu Ser Gly Ile Arg Tyr Asp
            900                 905                 910
Gly Lys Gly Tyr Ile Tyr Asn Ser Ser Ala Thr Gly Asp Gln Val Lys
            915                 920                 925
Ala Ser Phe Ile Thr Glu Ala Gly Asn Leu Tyr Tyr Phe Gly Lys Asp
930                 935                 940
Gly Tyr Met Val Thr Gly Ala Gln Thr Ile Asn Gly Ala Asn Tyr Phe
945                 950                 955                 960
Phe Leu Glu Asn Gly Thr Ala Leu Arg Asn Thr Ile Tyr Thr Asp Ala
                965                 970                 975
Gln Gly Asn Ser His Tyr Tyr Ala Asn Asp Gly Lys Arg Tyr Glu Asn
            980                 985                 990
Gly Tyr Gln Gln Phe Gly Asn Asp Trp Arg Tyr Phe Lys Asp Gly Asn
            995                 1000                1005
Met Ala Val Gly Leu Thr Thr Val Asp Gly Asn Val Gln Tyr Phe
1010                1015                1020
Asp Lys Asp Gly Val Gln Lys Asp Lys Ile Ile Val Thr Arg
1025                1030                1035
Asp Gly Lys Val Arg Tyr Phe Asp Gln His Asn Gly Asn Ala Val
1040                1045                1050
Thr Asn Thr Phe Ile Ala Asp Lys Thr Gly His Trp Tyr Tyr Leu
1055                1060                1065
Gly Lys Asp Gly Val Ala Val Thr Gly Ala Gln Thr Val Gly Lys
1070                1075                1080
Gln Lys Leu Tyr Phe Glu Ala Asn Gly Glu Gln Val Lys Gly Asp
1085                1090                1095
Phe Val Thr Ser His Glu Gly Lys Leu Tyr Phe Tyr Asp Val Asp
1100                1105                1110
Ser Gly Asp Met Trp Thr Asp Thr Phe Ile Glu Asp Lys Ala Gly
1115                1120                1125
Asn Trp Phe Tyr Leu Gly Lys Asp Gly Ala Ala Val Ser Gly Ala
1130                1135                1140
```

-continued

```
Gln Thr Ile Arg Gly Gln Lys Leu Tyr Phe Lys Ala Tyr Gly Gln
    1145                1150                1155

Gln Val Lys Gly Asp Ile Val Lys Gly Thr Asp Gly Lys Ile Arg
    1160                1165                1170

Tyr Tyr Asp Ala Lys Ser Gly Glu Gln Val Phe Asn Lys Thr Val
    1175                1180                1185

Lys Ala Ala Asp Gly Lys Thr Tyr Val Ile Gly Asn Asn Gly Val
    1190                1195                1200

Ala Val Asp Pro Ser Val Val Lys Gly Gln Thr Phe Lys Asp Ala
    1205                1210                1215

Ser Gly Ala Leu Arg Phe Tyr Asn Leu Lys Gly Gln Leu Val Thr
    1220                1225                1230

Gly Ser Gly Trp Tyr Glu Thr Ala Asn His Asp Trp Val Tyr Ile
    1235                1240                1245

Gln Ser Gly Lys Ala Leu Thr Gly Glu Gln Thr Ile Asn Gly Gln
    1250                1255                1260

His Leu Tyr Phe Lys Glu Asp Gly His Gln Val Lys Gly Gln Leu
    1265                1270                1275

Val Thr Arg Thr Asp Gly Lys Val Arg Tyr Tyr Asp Ala Asn Ser
    1280                1285                1290

Gly Asp Gln Ala Phe Asn Lys Ser Val Thr Val Asn Gly Lys Thr
    1295                1300                1305

Tyr Tyr Phe Gly Asn Asp Gly Thr Ala Gln Thr Ala Gly Asn Pro
    1310                1315                1320

Lys Gly Gln Ile Phe Lys Asp Gly Ser Val Leu Arg Phe Tyr Ser
    1325                1330                1335

Met Glu Gly Gln Leu Val Ile Gly Ser Gly Trp Tyr Ser Asn Ala
    1340                1345                1350

Gln Gly Gln Trp Leu Tyr Val Lys Asn Gly Lys Val Leu Thr Gly
    1355                1360                1365

Leu Gln Thr Val Gly Ser Gln Arg Val Tyr Phe Asp Glu Asn Gly
    1370                1375                1380

Ile Gln Ala Lys Gly Lys Ala Val Arg Thr Ser Asp Gly Lys Ile
    1385                1390                1395

Arg Tyr Phe Asp Glu Asn Ser Gly Ser Met Ile Thr Asn Gln Trp
    1400                1405                1410

Lys Phe Val Tyr Gly Gln Tyr Tyr Phe Gly Asn Asp Gly Ala
    1415                1420                1425

Ala Ile Tyr Arg Gly Trp Asn
    1430                1435
```

<210> SEQ ID NO 13
<211> LENGTH: 1340
<212> TYPE: PRT
<213> ORGANISM: Artificial sequence
<220> FEATURE:
<223> OTHER INFORMATION: Gtf 2919_N-terminally truncated enzyme with added start-methionine.

<400> SEQUENCE: 13

```
Met Ile Asp Gly Lys Tyr Tyr Val Asn Lys Asp Gly Ser His Lys
1               5                   10                  15

Glu Asn Phe Ala Ile Thr Val Asn Gly Gln Leu Leu Tyr Phe Gly Lys
                20                  25                  30

Asp Gly Ala Leu Thr Ser Ser Ser Thr Tyr Ser Phe Thr Gln Gly Thr
```

```
            35                  40                  45
Thr Asn Ile Val Asp Gly Phe Ser Lys Asn Asn Arg Ala Tyr Asp Ser
    50                  55                  60
Ser Glu Ala Ser Phe Glu Leu Ile Asp Gly Tyr Leu Thr Ala Asp Ser
 65                  70                  75                  80
Trp Tyr Arg Pro Val Ser Ile Ile Lys Asp Gly Val Thr Trp Gln Ala
                 85                  90                  95
Ser Thr Lys Glu Asp Phe Arg Pro Leu Leu Met Ala Trp Trp Pro Asn
                100                 105                 110
Val Asp Thr Gln Val Asn Tyr Leu Asn Tyr Met Ser Lys Val Phe Asn
            115                 120                 125
Leu Asp Ala Lys Tyr Thr Ser Thr Asp Lys Gln Val Asp Leu Asn Arg
    130                 135                 140
Ala Ala Lys Asp Ile Gln Val Lys Ile Glu Gln Lys Ile Gln Ala Glu
145                 150                 155                 160
Lys Ser Thr Gln Trp Leu Arg Glu Ala Ile Ser Ala Phe Val Lys Thr
                165                 170                 175
Gln Pro Gln Trp Asn Lys Glu Thr Glu Asn Phe Ser Lys Gly Gly Gly
                180                 185                 190
Glu Asp His Leu Gln Gly Gly Ala Leu Leu Tyr Val Asn Asp Pro Arg
            195                 200                 205
Thr Pro Trp Ala Asn Ser Asn Tyr Arg Leu Leu Asn Arg Thr Ala Thr
    210                 215                 220
Asn Gln Thr Gly Thr Ile Asp Lys Ser Val Leu Asp Glu Gln Ser Asp
225                 230                 235                 240
Pro Asn His Met Gly Gly Phe Asp Phe Leu Leu Ala Asn Asp Val Asp
                245                 250                 255
Thr Ser Asn Pro Val Val Gln Ala Glu Gln Leu Asn Gln Ile His Tyr
                260                 265                 270
Leu Met Asn Trp Gly Ser Ile Val Met Gly Asp Lys Asp Ala Asn Phe
            275                 280                 285
Asp Gly Ile Arg Val Asp Ala Val Asp Asn Val Asp Ala Asp Met Leu
    290                 295                 300
Gln Leu Tyr Thr Asn Tyr Phe Arg Glu Tyr Tyr Gly Val Asn Lys Ser
305                 310                 315                 320
Glu Ala Asn Ala Leu Ala His Ile Ser Val Leu Glu Ala Trp Ser Leu
                325                 330                 335
Asn Asp Asn His Tyr Asn Asp Lys Thr Asp Gly Ala Ala Leu Ala Met
            340                 345                 350
Glu Asn Lys Gln Arg Leu Ala Leu Leu Phe Ser Leu Ala Lys Pro Ile
        355                 360                 365
Lys Glu Arg Thr Pro Ala Val Ser Pro Leu Tyr Asn Asn Thr Phe Asn
    370                 375                 380
Thr Thr Gln Arg Asp Glu Lys Thr Asp Trp Ile Asn Lys Asp Gly Ser
385                 390                 395                 400
Lys Ala Tyr Asn Glu Asp Gly Thr Val Lys Gln Ser Thr Ile Gly Lys
                405                 410                 415
Tyr Asn Glu Lys Tyr Gly Asp Ala Ser Gly Asn Tyr Val Phe Ile Arg
            420                 425                 430
Ala His Asp Asn Asn Val Gln Asp Ile Ile Ala Glu Ile Ile Lys Lys
    435                 440                 445
Glu Ile Asn Pro Lys Ser Asp Gly Phe Thr Ile Thr Asp Ala Glu Met
450                 455                 460
```

-continued

```
Lys Lys Ala Phe Glu Ile Tyr Asn Lys Asp Met Leu Ser Ser Asp Lys
465                 470                 475                 480

Lys Tyr Thr Leu Asn Asn Ile Pro Ala Ala Tyr Ala Val Met Leu Gln
                    485                 490                 495

Asn Met Glu Thr Ile Thr Arg Val Tyr Tyr Gly Asp Leu Tyr Thr Asp
                500                 505                 510

Asp Gly His Tyr Met Glu Thr Lys Ser Pro Tyr Tyr Asp Thr Ile Val
            515                 520                 525

Asn Leu Met Lys Asn Arg Ile Lys Tyr Val Ser Gly Gln Ala Gln
530                 535                 540

Arg Ser Tyr Trp Leu Pro Thr Asp Gly Lys Met Asp Lys Ser Asp Val
545                 550                 555                 560

Glu Leu Tyr Arg Thr Asn Glu Val Tyr Thr Ser Val Arg Tyr Gly Lys
                565                 570                 575

Asp Ile Met Thr Ala Asp Asp Thr Gln Gly Ser Lys Tyr Ser Arg Thr
            580                 585                 590

Ser Gly Gln Val Thr Leu Val Val Asn Asn Pro Lys Leu Ser Leu Asp
        595                 600                 605

Lys Ser Ala Lys Leu Asp Val Glu Met Gly Lys Ile His Ala Asn Gln
610                 615                 620

Lys Tyr Arg Ala Leu Ile Val Gly Thr Pro Asn Gly Ile Lys Asn Phe
625                 630                 635                 640

Thr Ser Asp Ala Glu Ala Ile Ala Ala Gly Tyr Val Lys Glu Thr Asp
                645                 650                 655

Gly Asn Gly Val Leu Thr Phe Gly Ala Asn Asp Ile Lys Gly Tyr Glu
            660                 665                 670

Thr Phe Asp Met Ser Gly Phe Val Ala Val Trp Val Pro Val Gly Ala
        675                 680                 685

Ser Asp Asp Gln Asp Ile Arg Val Ala Ala Ser Thr Ala Ala Lys Lys
690                 695                 700

Glu Gly Glu Leu Thr Leu Lys Ala Thr Glu Ala Tyr Asp Ser Gln Leu
705                 710                 715                 720

Ile Tyr Glu Gly Phe Ser Asn Phe Gln Thr Ile Pro Asp Gly Ser Asp
                725                 730                 735

Pro Ser Val Tyr Thr Asn Arg Lys Ile Ala Glu Asn Val Asp Leu Phe
            740                 745                 750

Lys Ser Trp Gly Val Thr Ser Phe Glu Met Ala Pro Gln Phe Val Ser
        755                 760                 765

Ala Asp Asp Gly Thr Phe Leu Asp Ser Val Ile Gln Asn Gly Tyr Ala
770                 775                 780

Phe Ala Asp Arg Tyr Asp Leu Ala Met Ser Lys Asn Asn Lys Tyr Gly
785                 790                 795                 800

Ser Lys Glu Asp Leu Arg Asn Ala Leu Lys Ala Leu His Lys Ala Gly
                805                 810                 815

Ile Gln Ala Ile Ala Asp Trp Val Pro Asp Gln Ile Tyr Gln Leu Pro
            820                 825                 830

Gly Lys Glu Val Val Thr Ala Thr Arg Thr Asp Gly Ala Gly Arg Lys
        835                 840                 845

Ile Ser Asp Ala Ile Ile Asp His Ser Leu Tyr Val Ala Asn Ser Lys
850                 855                 860

Ser Ser Gly Lys Asp Tyr Gln Ala Lys Tyr Gly Gly Glu Phe Leu Ala
865                 870                 875                 880
```

-continued

Glu Leu Lys Ala Lys Tyr Pro Glu Met Phe Lys Val Asn Met Ile Ser
            885                 890                 895

Thr Gly Lys Pro Ile Asp Asp Ser Val Lys Leu Lys Gln Trp Lys Ala
        900                 905                 910

Glu Tyr Phe Asn Gly Thr Asn Val Leu Asp Arg Gly Val Gly Tyr Val
        915                 920                 925

Leu Ser Asp Glu Ala Thr Gly Lys Tyr Phe Thr Val Thr Lys Glu Gly
        930                 935                 940

Asn Phe Ile Pro Leu Gln Leu Lys Gly Asn Glu Lys Val Ile Thr Gly
945                 950                 955                 960

Phe Ser Ser Asp Gly Lys Gly Ile Thr Tyr Phe Gly Thr Ser Gly Asn
            965                 970                 975

Gln Ala Lys Ser Ala Phe Val Thr Phe Asn Gly Asn Thr Tyr Tyr Phe
            980                 985                 990

Asp Ala Arg Gly His Met Val Thr Asn Gly Glu Tyr Ser Pro Asn Gly
            995                 1000                1005

Lys Asp Val Tyr Arg Phe Leu Pro Asn Gly Ile Met Leu Ser Asn
    1010                1015                1020

Ala Phe Tyr Val Asp Gly Asn Gly Asn Thr Tyr Leu Tyr Asn Ser
    1025                1030                1035

Lys Gly Gln Met Tyr Lys Gly Gly Tyr Ser Lys Phe Asp Val Thr
    1040                1045                1050

Glu Thr Lys Asp Gly Lys Glu Ser Lys Val Val Lys Phe Arg Tyr
    1055                1060                1065

Phe Thr Asn Glu Gly Val Met Ala Lys Gly Val Thr Val Val Asp
    1070                1075                1080

Gly Phe Thr Gln Tyr Phe Asn Glu Asp Gly Ile Gln Ser Lys Asp
    1085                1090                1095

Glu Leu Val Thr Tyr Asn Gly Lys Thr Tyr Tyr Phe Glu Ala His
    1100                1105                1110

Thr Gly Asn Ala Ile Lys Asn Thr Trp Arg Asn Ile Lys Gly Lys
    1115                1120                1125

Trp Tyr His Phe Asp Ala Asn Gly Val Ala Ala Thr Gly Ala Gln
    1130                1135                1140

Val Ile Asn Gly Gln His Leu Tyr Phe Asn Glu Asp Gly Ser Gln
    1145                1150                1155

Val Lys Gly Gly Val Val Lys Asn Ala Asp Gly Thr Phe Ser Lys
    1160                1165                1170

Tyr Lys Asp Gly Ser Gly Asp Leu Val Val Asn Glu Phe Phe Thr
    1175                1180                1185

Thr Gly Asp Asn Val Trp Tyr Tyr Ala Gly Ala Asn Gly Lys Thr
    1190                1195                1200

Val Thr Gly Ala Gln Val Ile Asn Gly Gln His Leu Phe Phe Lys
    1205                1210                1215

Glu Asp Gly Ser Gln Val Lys Gly Asp Phe Val Lys Asn Ser Asp
    1220                1225                1230

Gly Thr Tyr Ser Lys Tyr Asp Ala Ala Ser Gly Glu Arg Leu Thr
    1235                1240                1245

Asn Glu Phe Phe Thr Thr Gly Asp Asn His Trp Tyr Tyr Ile Gly
    1250                1255                1260

Ala Asn Gly Lys Thr Val Thr Gly Glu Val Lys Ile Gly Asp Asp
    1265                1270                1275

Thr Tyr Phe Phe Ala Lys Asp Gly Lys Gln Leu Lys Gly Gln Ile

```
                1280                1285                1290
Val Thr Thr Arg Ser Gly Arg Ile Ser Tyr Tyr Phe Gly Asp Ser
            1295                1300                1305

Gly Lys Lys Ala Ile Ser Thr Trp Val Glu Ile Gln Pro Gly Val
            1310                1315                1320

Phe Val Phe Phe Asp Lys Asn Gly Leu Ala Tyr Pro Pro Glu Asn
            1325                1330                1335

Met Asn
    1340

<210> SEQ ID NO 14
<211> LENGTH: 1341
<212> TYPE: PRT
<213> ORGANISM: Artificial sequence
<220> FEATURE:
<223> OTHER INFORMATION: Gtf 2678_N-terminally truncated enzyme with
      added start-methionine.

<400> SEQUENCE: 14

Met Thr Asp Gly Lys Tyr Tyr Tyr Val Asn Glu Asp Gly Ser His Lys
1               5                   10                  15

Glu Asn Phe Ala Ile Thr Val Asn Gly Gln Leu Leu Tyr Phe Gly Lys
            20                  25                  30

Asp Gly Ala Leu Thr Ser Ser Thr His Ser Phe Thr Pro Gly Thr
        35                  40                  45

Thr Asn Ile Val Asp Gly Phe Ser Ile Asn Asn Arg Ala Tyr Asp Ser
    50                  55                  60

Ser Glu Ala Ser Phe Glu Leu Ile Asn Gly Tyr Leu Thr Ala Asp Ser
65                  70                  75                  80

Trp Tyr Arg Pro Val Ser Ile Ile Lys Asp Gly Val Thr Trp Gln Ala
                85                  90                  95

Ser Thr Ala Glu Asp Phe Arg Pro Leu Leu Met Ala Trp Trp Pro Asn
            100                 105                 110

Val Asp Thr Gln Val Asn Tyr Leu Asn Tyr Met Ser Lys Val Phe Asn
        115                 120                 125

Leu Glu Ala Lys Tyr Thr Ser Thr Asp Lys Gln Ala Asp Leu Asn Arg
    130                 135                 140

Ala Ala Lys Asp Ile Gln Val Lys Ile Glu Gln Lys Ile Gln Ala Glu
145                 150                 155                 160

Lys Ser Thr Gln Trp Leu Arg Glu Thr Ile Ser Ala Phe Val Lys Thr
                165                 170                 175

Gln Pro Gln Trp Asn Lys Glu Thr Glu Asn Tyr Ser Lys Gly Gly Gly
            180                 185                 190

Glu Asp His Leu Gln Gly Gly Ala Leu Leu Tyr Val Asn Asp Ser Arg
        195                 200                 205

Thr Pro Trp Ala Asn Ser Asn Tyr Arg Leu Leu Asn Arg Thr Ala Thr
    210                 215                 220

Asn Gln Thr Gly Thr Ile Asn Lys Ser Val Leu Asp Glu Gln Ser Asp
225                 230                 235                 240

Pro Asn His Met Gly Gly Phe Asp Phe Leu Leu Ala Asn Asp Val Asp
                245                 250                 255

Leu Ser Asn Pro Val Val Gln Ala Glu Gln Leu Asn Gln Ile His Tyr
            260                 265                 270

Leu Met Asn Trp Gly Ser Ile Val Met Gly Asp Lys Asp Ala Asn Phe
        275                 280                 285
```

```
Asp Gly Ile Arg Val Asp Ala Val Asp Asn Val Asn Ala Asp Met Leu
    290                 295                 300

Gln Leu Tyr Thr Asn Tyr Phe Arg Glu Tyr Tyr Gly Val Asn Lys Ser
305                 310                 315                 320

Glu Ala Gln Ala Leu Ala His Ile Ser Val Leu Glu Ala Trp Ser Leu
                325                 330                 335

Asn Asp Asn His Tyr Asn Asp Lys Thr Asp Gly Ala Ala Leu Ala Met
                340                 345                 350

Glu Asn Lys Gln Arg Leu Ala Leu Leu Phe Ser Leu Ala Lys Pro Ile
        355                 360                 365

Lys Asp Arg Thr Pro Ala Val Ser Pro Leu Tyr Asn Asn Thr Phe Asn
370                 375                 380

Thr Thr Gln Arg Asp Phe Lys Thr Asp Trp Ile Asn Lys Asp Gly Ser
385                 390                 395                 400

Thr Ala Tyr Asn Glu Asp Gly Thr Ala Lys Gln Ser Thr Ile Gly Lys
                405                 410                 415

Tyr Asn Glu Lys Tyr Gly Asp Ala Ser Gly Asn Tyr Val Phe Ile Arg
            420                 425                 430

Ala His Asp Asn Asn Val Gln Asp Ile Ile Ala Glu Ile Ile Lys Lys
        435                 440                 445

Glu Ile Asn Lys Lys Ser Asp Gly Phe Thr Ile Ser Asp Ser Glu Met
    450                 455                 460

Lys Gln Ala Phe Glu Ile Tyr Asn Lys Asp Met Leu Ser Ser Asn Lys
465                 470                 475                 480

Lys Tyr Thr Leu Asn Asn Ile Pro Ala Ala Tyr Ala Val Met Leu Gln
                485                 490                 495

Asn Met Glu Thr Ile Thr Arg Val Tyr Tyr Gly Asp Leu Tyr Thr Asp
                500                 505                 510

Asp Gly His Tyr Met Glu Thr Lys Ser Pro Tyr His Asp Thr Ile Val
        515                 520                 525

Asn Leu Met Lys Asn Arg Ile Lys Tyr Val Ser Gly Gly Gln Ala Gln
    530                 535                 540

Arg Ser Tyr Trp Leu Pro Thr Asp Gly Lys Met Asp Asn Ser Asp Val
545                 550                 555                 560

Glu Leu Tyr Arg Thr Ser Glu Val Tyr Thr Ser Val Arg Tyr Gly Lys
                565                 570                 575

Asp Ile Met Thr Ala Asp Asp Thr Glu Gly Ser Lys Tyr Ser Arg Thr
            580                 585                 590

Ser Gly Gln Val Thr Leu Val Val Asn Asn Pro Lys Leu Thr Leu His
        595                 600                 605

Glu Ser Ala Lys Leu Asn Val Glu Met Gly Lys Ile His Ala Asn Gln
    610                 615                 620

Lys Tyr Arg Ala Leu Ile Val Gly Thr Ala Asp Gly Ile Lys Asn Phe
625                 630                 635                 640

Thr Ser Asp Ala Glu Ala Ile Ala Ala Gly Tyr Val Lys Glu Thr Asp
                645                 650                 655

Ser Asn Gly Val Leu Thr Phe Gly Ala Asn Asp Ile Lys Gly Tyr Glu
            660                 665                 670

Thr Phe Asp Met Ser Gly Phe Val Ala Val Trp Val Pro Val Gly Ala
        675                 680                 685

Ser Asp Asp Gln Asp Ile Arg Val Ala Pro Ser Thr Glu Ala Lys Lys
    690                 695                 700

Glu Gly Glu Leu Thr Leu Lys Ala Thr Glu Ala Tyr Asp Ser Gln Leu
```

-continued

```
            705                 710                 715                 720
        Ile Tyr Glu Gly Phe Ser Asn Phe Gln Thr Ile Pro Asp Gly Ser Asp
                        725                 730                 735
        Pro Ser Val Tyr Thr Asn Arg Lys Ile Ala Glu Asn Val Asp Leu Phe
                        740                 745                 750
        Lys Ser Trp Gly Val Thr Ser Phe Glu Met Ala Pro Gln Phe Val Ser
                        755                 760                 765
        Ala Asp Asp Gly Thr Phe Leu Asp Ser Val Ile Gln Asn Gly Tyr Ala
                        770                 775                 780
        Phe Ala Asp Arg Tyr Asp Leu Ala Met Ser Lys Asn Asn Lys Tyr Gly
        785                 790                 795                 800
        Ser Lys Glu Asp Leu Arg Asp Ala Leu Lys Ala Leu His Lys Ala Gly
                        805                 810                 815
        Ile Gln Ala Ile Ala Asp Trp Val Pro Asp Gln Ile Tyr Gln Leu Pro
                        820                 825                 830
        Gly Lys Glu Val Val Thr Ala Thr Arg Thr Asp Gly Ala Gly Arg Lys
                        835                 840                 845
        Ile Ala Asp Ala Ile Ile Asp His Ser Leu Tyr Val Ala Asn Ser Lys
                        850                 855                 860
        Ser Ser Gly Arg Asp Tyr Gln Ala Gln Tyr Gly Gly Glu Phe Leu Ala
        865                 870                 875                 880
        Glu Leu Lys Ala Lys Tyr Pro Lys Met Phe Thr Glu Asn Met Ile Ser
                        885                 890                 895
        Thr Gly Lys Pro Ile Asp Asp Ser Val Lys Leu Lys Gln Trp Lys Ala
                        900                 905                 910
        Lys Tyr Phe Asn Gly Thr Asn Val Leu Asp Arg Gly Val Gly Tyr Val
                        915                 920                 925
        Leu Ser Asp Glu Ala Thr Gly Lys Tyr Phe Thr Val Thr Lys Glu Gly
                        930                 935                 940
        Asn Phe Ile Pro Leu Gln Leu Thr Gly Asn Glu Lys Ala Val Thr Gly
        945                 950                 955                 960
        Phe Ser Asn Asp Gly Lys Gly Ile Thr Tyr Phe Gly Thr Ser Gly Asn
                        965                 970                 975
        Gln Ala Lys Ser Ala Phe Val Thr Phe Asn Gly Asn Thr Tyr Tyr Phe
                        980                 985                 990
        Asp Ala Arg Gly His Met Val Thr Asn Gly Glu Tyr Ser Pro Asn Gly
                        995                 1000                1005
        Lys Asp Val Tyr Arg Phe Leu Pro Asn Gly Ile Met Leu Ser Asn
                    1010                1015                1020
        Ala Phe Tyr Val Asp Ala Asn Gly Asn Thr Tyr Leu Tyr Asn Tyr
                    1025                1030                1035
        Lys Gly Gln Met Tyr Lys Gly Gly Tyr Thr Lys Phe Asp Val Thr
                    1040                1045                1050
        Glu Thr Asp Lys Asp Gly Asn Glu Ser Lys Val Val Lys Phe Arg
                    1055                1060                1065
        Tyr Phe Thr Asn Glu Gly Val Met Ala Lys Gly Leu Thr Val Ile
                    1070                1075                1080
        Asp Gly Ser Thr Gln Tyr Phe Gly Glu Asp Gly Phe Gln Thr Lys
                    1085                1090                1095
        Asp Lys Leu Ala Thr Tyr Lys Gly Lys Thr Tyr Tyr Phe Glu Ala
                    1100                1105                1110
        His Thr Gly Asn Ala Ile Lys Asn Thr Trp Arg Asn Ile Asp Gly
                    1115                1120                1125
```

-continued

Lys Trp Tyr His Phe Asp Glu Asn Gly Val Ala Ala Thr Gly Ala
1130                1135                1140

Gln Val Ile Asn Gly Gln Lys Leu Tyr Phe Asn Glu Asp Gly Ser
    1145                1150                1155

Gln Val Lys Gly Gly Val Val Lys Asn Ala Asp Gly Thr Tyr Ser
    1160                1165                1170

Lys Tyr Lys Glu Gly Ser Gly Glu Leu Val Thr Asn Glu Phe Phe
    1175                1180                1185

Thr Thr Asp Gly Asn Val Trp Tyr Ala Gly Ala Asp Gly Lys
    1190                1195                1200

Thr Val Thr Gly Ala Gln Val Ile Asn Gly Gln His Leu Tyr Phe
    1205                1210                1215

Lys Glu Asp Gly Ser Gln Val Lys Gly Gly Val Val Lys Asn Ala
    1220                1225                1230

Asp Gly Thr Tyr Ser Lys Tyr Asp Ala Ala Thr Gly Glu Arg Leu
    1235                1240                1245

Thr Asn Glu Phe Phe Thr Thr Gly Asp Asn Asn Trp Tyr Tyr Ile
    1250                1255                1260

Gly Ser Asn Gly Lys Thr Val Thr Gly Glu Val Lys Ile Gly Ala
    1265                1270                1275

Asp Thr Tyr Tyr Phe Ala Lys Asp Gly Lys Gln Val Lys Gly Gln
    1280                1285                1290

Thr Val Thr Ala Gly Asn Gly Arg Ile Ser Tyr Tyr Tyr Gly Asp
    1295                1300                1305

Ser Gly Lys Lys Ala Ile Ser Thr Trp Ile Glu Ile Gln Pro Gly
    1310                1315                1320

Ile Tyr Val Tyr Phe Asp Lys Thr Gly Ile Ala Tyr Pro Pro Arg
    1325                1330                1335

Val Leu Asn
    1340

<210> SEQ ID NO 15
<211> LENGTH: 1341
<212> TYPE: PRT
<213> ORGANISM: Artificial sequence
<220> FEATURE:
<223> OTHER INFORMATION: Gtf 3929_N-terminally truncated enzyme with
      added start-methionine.

<400> SEQUENCE: 15

Met Ile Asp Gly Lys Tyr Tyr Tyr Val Asn Glu Asp Gly Ser His Lys
1               5                   10                  15

Glu Asn Phe Ala Ile Thr Val Asn Gly Gln Leu Leu Tyr Phe Gly Lys
            20                  25                  30

Asp Gly Ala Leu Thr Ser Ser Thr Tyr Ser Phe Thr Pro Gly Thr
        35                  40                  45

Thr Asn Ile Val Asp Gly Phe Ser Ile Asn Asn Arg Ala Tyr Asp Ser
    50                  55                  60

Ser Glu Ala Ser Phe Glu Leu Ile Asp Gly Tyr Leu Thr Ala Asp Ser
65                  70                  75                  80

Trp Tyr Arg Pro Ala Ser Ile Ile Lys Asp Gly Val Thr Trp Gln Ala
                85                  90                  95

Ser Thr Ala Glu Asp Phe Arg Pro Leu Leu Met Ala Trp Trp Pro Asn
            100                 105                 110

Val Asp Thr Gln Val Asn Tyr Leu Asn Tyr Met Ser Lys Val Phe Asn

-continued

```
            115                 120                 125
Leu Asp Ala Lys Tyr Thr Ser Thr Asp Lys Gln Glu Thr Leu Asn Val
        130                 135                 140
Ala Ala Lys Asp Ile Gln Val Lys Ile Glu Gln Lys Ile Gln Ala Glu
145                 150                 155                 160
Lys Ser Thr Gln Trp Leu Arg Glu Thr Ile Ser Ala Phe Val Lys Thr
                165                 170                 175
Gln Pro Gln Trp Asn Lys Glu Thr Glu Asn Tyr Ser Lys Gly Gly Gly
            180                 185                 190
Glu Asp His Leu Gln Gly Gly Ala Leu Leu Tyr Val Asn Asp Ser Arg
        195                 200                 205
Thr Pro Trp Ala Asn Ser Asn Tyr Arg Leu Leu Asn His Thr Ala Thr
210                 215                 220
Asn Gln Lys Gly Thr Ile Asp Lys Ser Val Leu Asp Glu Gln Ser Asp
225                 230                 235                 240
Pro Asn His Met Gly Gly Phe Asp Phe Leu Leu Ala Asn Asp Val Asp
                245                 250                 255
Leu Ser Asn Pro Val Val Gln Ala Glu Gln Leu Asn Gln Ile His Tyr
            260                 265                 270
Leu Met Asn Trp Gly Ser Ile Val Met Gly Asp Lys Asp Ala Asn Phe
        275                 280                 285
Asp Gly Ile Arg Val Asp Ala Val Asp Asn Val Asp Ala Asp Met Leu
290                 295                 300
Gln Leu Tyr Thr Asn Tyr Phe Arg Glu Tyr Tyr Gly Val Asn Lys Ser
305                 310                 315                 320
Glu Ala Asn Ala Leu Ala His Ile Ser Val Leu Glu Ala Trp Ser Leu
                325                 330                 335
Asn Asp Asn His Tyr Asn Asp Lys Thr Asp Gly Ala Ala Leu Ala Met
            340                 345                 350
Glu Asn Lys Gln Arg Leu Ala Leu Leu Phe Ser Leu Ala Lys Pro Ile
        355                 360                 365
Lys Glu Arg Thr Pro Ala Val Ser Pro Leu Tyr Asn Asn Thr Phe Asn
370                 375                 380
Thr Thr Gln Arg Asp Glu Lys Thr Asp Trp Ile Asn Lys Asp Gly Ser
385                 390                 395                 400
Lys Ala Tyr Asn Glu Asp Gly Thr Val Lys Gln Ser Thr Ile Gly Lys
                405                 410                 415
Tyr Asn Glu Lys Tyr Gly Asp Ala Ser Gly Asn Tyr Val Phe Ile Arg
            420                 425                 430
Ala His Asp Asn Asn Val Gln Asp Ile Ile Ala Glu Ile Ile Lys Lys
        435                 440                 445
Glu Ile Asn Pro Lys Ser Asp Gly Phe Thr Ile Thr Asp Ala Glu Met
450                 455                 460
Lys Lys Ala Phe Glu Ile Tyr Asn Lys Asp Met Leu Ser Ser Asp Lys
465                 470                 475                 480
Lys Tyr Thr Leu Asn Asn Ile Pro Ala Ala Tyr Ala Val Met Leu Gln
                485                 490                 495
Asn Met Glu Thr Ile Thr Arg Val Tyr Tyr Gly Asp Leu Tyr Thr Asp
            500                 505                 510
Asn Gly Asn Tyr Met Glu Thr Lys Ser Pro Tyr Tyr Asp Thr Ile Val
        515                 520                 525
Asn Leu Met Lys Asn Arg Ile Lys Tyr Val Ser Gly Gly Gln Ala Gln
530                 535                 540
```

```
Arg Ser Tyr Trp Leu Pro Thr Asp Gly Lys Met Asp Asn Ser Asp Val
545                 550                 555                 560

Glu Leu Tyr Arg Thr Asn Glu Val Tyr Ala Ser Val Arg Tyr Gly Lys
                565                 570                 575

Asp Ile Met Thr Ala Asp Asp Thr Glu Gly Ser Lys Tyr Ser Arg Thr
                580                 585                 590

Ser Gly Gln Val Thr Leu Val Ala Asn Asn Pro Lys Leu Thr Leu Asp
            595                 600                 605

Gln Ser Ala Lys Leu Lys Val Glu Met Gly Lys Ile His Ala Asn Gln
            610                 615                 620

Lys Tyr Arg Ala Leu Ile Val Gly Thr Ala Asp Gly Ile Lys Asn Phe
625                 630                 635                 640

Thr Ser Asp Ala Asp Ala Ile Ala Ala Gly Tyr Val Lys Glu Thr Asp
                645                 650                 655

Ser Asn Gly Val Leu Thr Phe Gly Ala Asn Asp Ile Lys Gly Tyr Glu
            660                 665                 670

Thr Phe Asp Met Ser Gly Phe Val Ala Val Trp Val Pro Val Gly Ala
            675                 680                 685

Ser Asp Asp Gln Asp Ile Arg Val Ala Pro Ser Thr Glu Ala Lys Lys
            690                 695                 700

Glu Gly Glu Leu Thr Leu Lys Ala Thr Glu Ala Tyr Asp Ser Gln Leu
705                 710                 715                 720

Ile Tyr Glu Gly Phe Ser Asn Phe Gln Thr Ile Pro Asp Gly Ser Asp
                725                 730                 735

Pro Ser Val Tyr Thr Asn Arg Lys Ile Ala Glu Asn Val Asp Leu Phe
                740                 745                 750

Lys Ser Trp Gly Val Thr Ser Phe Glu Met Ala Pro Gln Phe Val Ser
            755                 760                 765

Ala Asp Asp Gly Thr Phe Leu Asp Ser Val Ile Gln Asn Gly Tyr Ala
770                 775                 780

Phe Ala Asp Arg Tyr Asp Leu Ala Met Ser Lys Asn Asn Lys Tyr Gly
785                 790                 795                 800

Ser Lys Glu Asp Leu Arg Asp Ala Leu Lys Ala Leu His Lys Ala Gly
                805                 810                 815

Ile Gln Ala Ile Ala Asp Trp Val Pro Asp Gln Ile Tyr Gln Leu Pro
                820                 825                 830

Gly Lys Glu Val Val Thr Ala Thr Arg Thr Asp Gly Ala Gly Arg Lys
            835                 840                 845

Ile Ala Asp Ala Ile Ile Asp His Ser Leu Tyr Val Ala Asn Thr Lys
            850                 855                 860

Ser Ser Gly Lys Asp Tyr Gln Ala Lys Tyr Gly Gly Glu Phe Leu Ala
865                 870                 875                 880

Glu Leu Lys Ala Lys Tyr Pro Glu Met Phe Lys Val Asn Met Ile Ser
                885                 890                 895

Thr Gly Lys Pro Ile Asp Asp Ser Val Lys Leu Lys Gln Trp Lys Ala
                900                 905                 910

Glu Tyr Phe Asn Gly Thr Asn Val Leu Glu Arg Gly Val Gly Tyr Val
            915                 920                 925

Leu Ser Asp Glu Ala Thr Gly Lys Tyr Phe Thr Val Thr Lys Asp Gly
            930                 935                 940

Asn Phe Ile Pro Leu Gln Leu Thr Gly Asn Glu Lys Val Val Thr Gly
945                 950                 955                 960
```

```
Phe Ser Asn Asp Gly Lys Gly Ile Thr Tyr Phe Gly Thr Ser Gly Thr
                965                 970                 975

Gln Ala Lys Ser Ala Phe Val Thr Phe Asn Gly Asn Thr Tyr Tyr Phe
            980                 985                 990

Asp Ala Arg Gly His Met Val Thr Asn Gly Glu Tyr Ser Pro Asn Gly
        995                 1000                1005

Lys Asp Val Tyr Arg Phe Leu Pro Asn Gly Ile Met Leu Ser Asn
    1010                1015                1020

Ala Phe Tyr Val Asp Ala Asn Gly Asn Thr Tyr Leu Tyr Asn Ser
    1025                1030                1035

Lys Gly Gln Met Tyr Lys Gly Gly Tyr Thr Lys Phe Asp Val Thr
    1040                1045                1050

Glu Thr Asp Lys Asp Gly Lys Glu Ser Lys Val Val Lys Phe Arg
    1055                1060                1065

Tyr Phe Thr Asn Glu Gly Val Met Ala Lys Gly Val Thr Val Ile
    1070                1075                1080

Asp Gly Phe Thr Gln Tyr Phe Gly Glu Asp Gly Phe Gln Ala Lys
    1085                1090                1095

Asp Lys Leu Val Thr Phe Lys Gly Lys Thr Tyr Tyr Phe Asp Ala
    1100                1105                1110

His Thr Gly Asn Ala Ile Lys Asn Thr Trp Arg Asn Ile Asp Gly
    1115                1120                1125

Lys Trp Tyr His Phe Asp Ala Asn Gly Val Ala Ala Thr Gly Ala
    1130                1135                1140

Gln Val Ile Asn Gly Gln Lys Leu Tyr Phe Asn Glu Asp Gly Ser
    1145                1150                1155

Gln Val Lys Gly Gly Val Val Lys Asn Ala Asp Gly Thr Tyr Ser
    1160                1165                1170

Lys Tyr Lys Glu Gly Ser Gly Glu Leu Val Thr Asn Glu Phe Phe
    1175                1180                1185

Thr Thr Asp Gly Asn Val Trp Tyr Tyr Ala Gly Ala Asn Gly Lys
    1190                1195                1200

Thr Val Thr Gly Ala Gln Val Ile Asn Gly Gln His Leu Tyr Phe
    1205                1210                1215

Asn Ala Asp Gly Ser Gln Val Lys Gly Gly Val Val Lys Asn Ala
    1220                1225                1230

Asp Gly Thr Tyr Ser Lys Tyr Asp Ala Ala Thr Gly Glu Arg Leu
    1235                1240                1245

Thr Asn Glu Phe Phe Thr Thr Gly Asp Asn Asn Trp Tyr Tyr Ile
    1250                1255                1260

Gly Ala Asn Gly Lys Thr Val Thr Gly Glu Val Lys Ile Gly Asp
    1265                1270                1275

Asp Thr Tyr Tyr Phe Ala Lys Asp Gly Lys Gln Val Lys Gly Gln
    1280                1285                1290

Thr Val Ser Ala Gly Asn Gly Arg Ile Ser Tyr Tyr Tyr Gly Asp
    1295                1300                1305

Ser Gly Lys Arg Ala Val Ser Thr Trp Val Glu Ile Gln Pro Gly
    1310                1315                1320

Val Tyr Val Tyr Phe Asp Lys Asn Gly Leu Ala Tyr Pro Pro Arg
    1325                1330                1335

Val Leu Asn
    1340
```

```
<210> SEQ ID NO 16
<211> LENGTH: 1341
<212> TYPE: PRT
<213> ORGANISM: Artificial sequence
<220> FEATURE:
<223> OTHER INFORMATION: Gtf 7527-short

<400> SEQUENCE: 16

Met Ile Asp Gly Lys Tyr Tyr Val Asn Glu Asp Gly Ser His Lys
1               5                   10                  15

Glu Asn Phe Ala Ile Thr Val Asn Gly Gln Leu Leu Tyr Phe Gly Lys
            20                  25                  30

Asp Gly Ala Leu Thr Ser Ser Thr Tyr Ser Phe Thr Pro Gly Thr
        35                  40                  45

Thr Asn Ile Val Asp Gly Phe Ser Ile Asn Asn Arg Ala Tyr Asp Ser
    50                  55                  60

Ser Glu Ala Ser Phe Glu Leu Ile Asp Gly Tyr Leu Thr Ala Asp Ser
65                  70                  75                  80

Trp Tyr Arg Pro Ala Ser Ile Ile Lys Asp Gly Val Thr Trp Gln Ala
                85                  90                  95

Ser Thr Ala Glu Asp Phe Arg Pro Leu Leu Met Ala Trp Trp Pro Asn
            100                 105                 110

Val Asp Thr Gln Val Asn Tyr Leu Asn Tyr Met Ser Lys Val Phe Asn
        115                 120                 125

Leu Asp Ala Lys Tyr Ser Ser Thr Asp Lys Gln Glu Thr Leu Lys Val
    130                 135                 140

Ala Ala Lys Asp Ile Gln Ile Lys Ile Glu Gln Lys Ile Gln Ala Glu
145                 150                 155                 160

Lys Ser Thr Gln Trp Leu Arg Glu Thr Ile Ser Ala Phe Val Lys Thr
                165                 170                 175

Gln Pro Gln Trp Asn Lys Glu Thr Glu Asn Tyr Ser Lys Gly Gly Gly
            180                 185                 190

Glu Asp His Leu Gln Gly Gly Ala Leu Leu Tyr Val Asn Asp Ser Arg
        195                 200                 205

Thr Pro Trp Ala Asn Ser Asp Tyr Arg Arg Leu Asn Arg Thr Ala Thr
    210                 215                 220

Asn Gln Thr Gly Thr Ile Asp Lys Ser Ile Leu Asp Glu Gln Ser Asp
225                 230                 235                 240

Pro Asn His Met Gly Gly Phe Asp Phe Leu Leu Ala Asn Asp Val Asp
                245                 250                 255

Leu Ser Asn Pro Val Val Gln Ala Glu Gln Leu Asn Gln Ile His Tyr
            260                 265                 270

Leu Met Asn Trp Gly Ser Ile Val Met Gly Asp Lys Asp Ala Asn Phe
        275                 280                 285

Asp Gly Ile Arg Val Asp Ala Val Asp Asn Val Asp Ala Asp Met Leu
    290                 295                 300

Gln Leu Tyr Thr Asn Tyr Phe Arg Glu Tyr Tyr Gly Val Asn Lys Ser
305                 310                 315                 320

Glu Ala Asn Ala Leu Ala His Ile Ser Val Leu Glu Ala Trp Ser Leu
                325                 330                 335

Asn Asp Asn His Tyr Asn Asp Lys Thr Asp Gly Ala Ala Leu Ala Met
            340                 345                 350

Glu Asn Lys Gln Arg Leu Ala Leu Leu Phe Ser Leu Ala Lys Pro Ile
        355                 360                 365

Lys Glu Arg Thr Pro Ala Val Ser Pro Leu Tyr Asn Asn Thr Phe Asn
```

```
              370                 375                 380
Thr Thr Gln Arg Asp Glu Lys Thr Asp Trp Ile Asn Lys Asp Gly Ser
385                 390                 395                 400

Lys Ala Tyr Asn Glu Asp Gly Thr Val Lys Gln Ser Thr Ile Gly Lys
                405                 410                 415

Tyr Asn Glu Lys Tyr Gly Asp Ala Ser Gly Asn Tyr Val Phe Ile Arg
                420                 425                 430

Ala His Asp Asn Asn Val Gln Asp Ile Ile Ala Glu Ile Ile Lys Lys
                435                 440                 445

Glu Ile Asn Pro Lys Ser Asp Gly Phe Thr Ile Thr Asp Ala Glu Met
            450                 455                 460

Lys Gln Ala Phe Glu Ile Tyr Asn Lys Asp Met Leu Ser Ser Asp Lys
465                 470                 475                 480

Lys Tyr Thr Leu Asn Asn Ile Pro Ala Ala Tyr Ala Val Met Leu Gln
                485                 490                 495

Asn Met Glu Thr Ile Thr Arg Val Tyr Tyr Gly Asp Leu Tyr Thr Asp
            500                 505                 510

Asp Gly His Tyr Met Glu Thr Lys Ser Pro Tyr Tyr Asp Thr Ile Val
            515                 520                 525

Asn Leu Met Lys Ser Arg Ile Lys Tyr Val Ser Gly Gly Gln Ala Gln
            530                 535                 540

Arg Ser Tyr Trp Leu Pro Thr Asp Gly Lys Met Asp Asn Ser Asp Val
545                 550                 555                 560

Glu Leu Tyr Arg Thr Asn Glu Val Tyr Thr Ser Val Arg Tyr Gly Lys
                565                 570                 575

Asp Ile Met Thr Ala Asn Asp Thr Glu Gly Ser Lys Tyr Ser Arg Thr
            580                 585                 590

Ser Gly Gln Val Thr Leu Val Ala Asn Asn Pro Lys Leu Asn Leu Asp
            595                 600                 605

Gln Ser Ala Lys Leu Asn Val Glu Met Gly Lys Ile His Ala Asn Gln
            610                 615                 620

Lys Tyr Arg Ala Leu Ile Val Gly Thr Ala Asp Gly Ile Lys Asn Phe
625                 630                 635                 640

Thr Ser Asp Ala Asp Ala Ile Ala Ala Gly Tyr Val Lys Glu Thr Asp
                645                 650                 655

Ser Asn Gly Val Leu Thr Phe Gly Ala Asn Asp Ile Lys Gly Tyr Glu
                660                 665                 670

Thr Phe Asp Met Ser Gly Phe Val Ala Val Trp Val Pro Val Gly Ala
            675                 680                 685

Ser Asp Asn Gln Asp Ile Arg Val Ala Pro Ser Thr Glu Ala Lys Lys
            690                 695                 700

Glu Gly Glu Leu Thr Leu Lys Ala Thr Glu Ala Tyr Asp Ser Gln Leu
705                 710                 715                 720

Ile Tyr Glu Gly Phe Ser Asn Phe Gln Thr Ile Pro Asp Gly Ser Asp
                725                 730                 735

Pro Ser Val Tyr Thr Asn Arg Lys Ile Ala Glu Asn Val Asp Leu Phe
                740                 745                 750

Lys Ser Trp Gly Val Thr Ser Phe Glu Met Ala Pro Gln Phe Val Ser
            755                 760                 765

Ala Asp Asp Gly Thr Phe Leu Asp Ser Val Ile Gln Asn Gly Tyr Ala
            770                 775                 780

Phe Ala Asp Arg Tyr Asp Leu Ala Met Ser Lys Asn Asn Lys Tyr Gly
785                 790                 795                 800
```

-continued

```
Ser Lys Glu Asp Leu Arg Asp Ala Leu Lys Ala Leu His Lys Ala Gly
            805                 810                 815
Ile Gln Ala Ile Ala Asp Trp Val Pro Asp Gln Ile Tyr Gln Leu Pro
            820                 825                 830
Gly Lys Glu Val Val Thr Ala Thr Arg Thr Asp Gly Ala Gly Arg Lys
            835                 840                 845
Ile Ala Asp Ala Ile Ile Asp His Ser Leu Tyr Val Ala Asn Ser Lys
            850                 855                 860
Ser Ser Gly Lys Asp Tyr Gln Ala Lys Tyr Gly Gly Glu Phe Leu Ala
865                 870                 875                 880
Glu Leu Lys Ala Lys Tyr Pro Glu Met Phe Lys Val Asn Met Ile Ser
            885                 890                 895
Thr Gly Lys Pro Ile Asp Asp Ser Val Lys Leu Lys Gln Trp Lys Ala
            900                 905                 910
Glu Tyr Phe Asn Gly Thr Asn Val Leu Glu Arg Gly Val Gly Tyr Val
            915                 920                 925
Leu Ser Asp Glu Ala Thr Gly Lys Tyr Phe Thr Val Thr Lys Glu Gly
            930                 935                 940
Asn Phe Ile Pro Leu Gln Leu Thr Gly Lys Glu Lys Val Ile Thr Gly
945                 950                 955                 960
Phe Ser Ser Asp Gly Lys Gly Ile Thr Tyr Phe Gly Thr Ser Gly Thr
            965                 970                 975
Gln Ala Lys Ser Ala Phe Val Thr Phe Asn Gly Asn Thr Tyr Tyr Phe
            980                 985                 990
Asp Ala Arg Gly His Met Val Thr Asn Ser Glu Tyr Ser Pro Asn Gly
            995                 1000                1005
Lys Asp Val Tyr Arg Phe Leu Pro Asn Gly Ile Met Leu Ser Asn
    1010                1015                1020
Ala Phe Tyr Ile Asp Ala Asn Gly Asn Thr Tyr Leu Tyr Asn Ser
    1025                1030                1035
Lys Gly Gln Met Tyr Lys Gly Gly Tyr Thr Lys Phe Asp Val Ser
    1040                1045                1050
Glu Thr Asp Lys Asp Gly Lys Glu Ser Lys Val Val Lys Phe Arg
    1055                1060                1065
Tyr Phe Thr Asn Glu Gly Val Met Ala Lys Gly Val Thr Val Ile
    1070                1075                1080
Asp Gly Phe Thr Gln Tyr Phe Gly Glu Asp Gly Phe Gln Ala Lys
    1085                1090                1095
Asp Lys Leu Val Thr Phe Lys Gly Lys Thr Tyr Tyr Phe Asp Ala
    1100                1105                1110
His Thr Gly Asn Gly Ile Lys Asp Thr Trp Arg Asn Ile Asn Gly
    1115                1120                1125
Lys Trp Tyr Tyr Phe Asp Ala Asn Gly Val Ala Ala Thr Gly Ala
    1130                1135                1140
Gln Val Ile Asn Gly Gln Lys Leu Tyr Phe Asn Glu Asp Gly Ser
    1145                1150                1155
Gln Val Lys Gly Gly Val Val Lys Asn Ala Asp Gly Thr Tyr Ser
    1160                1165                1170
Lys Tyr Lys Glu Gly Phe Gly Glu Leu Val Thr Asn Glu Phe Phe
    1175                1180                1185
Thr Thr Asp Gly Asn Val Trp Tyr Tyr Ala Gly Ala Asn Gly Lys
    1190                1195                1200
```

-continued

| | | | | | | | | | | | | | |
|---|---|---|---|---|---|---|---|---|---|---|---|---|---|
| Thr | Val 1205 | Thr | Gly | Ala | Gln | Val 1210 | Ile | Asn | Gly | Gln | His 1215 | Leu | Tyr | Phe |
| Asn | Ala 1220 | Asp | Gly | Ser | Gln | Val 1225 | Lys | Gly | Val | Val 1230 | Lys | Asn | Ala |
| Asp | Gly 1235 | Thr | Tyr | Ser | Lys | Tyr 1240 | Asn | Ala | Ser | Thr | Gly 1245 | Glu | Arg | Leu |
| Thr | Asn 1250 | Glu | Phe | Phe | Thr | Thr 1255 | Gly | Asp | Asn | Asn | Trp 1260 | Tyr | Tyr | Ile |
| Gly | Ala 1265 | Asn | Gly | Lys | Ser | Val 1270 | Thr | Gly | Glu | Val | Lys 1275 | Ile | Gly | Asp |
| Asp | Thr 1280 | Tyr | Phe | Phe | Ala | Lys 1285 | Asp | Gly | Lys | Gln | Val 1290 | Lys | Gly | Gln |
| Thr | Val 1295 | Ser | Ala | Gly | Asn | Gly 1300 | Arg | Ile | Ser | Tyr | Tyr 1305 | Tyr | Gly | Asp |
| Ser | Gly 1310 | Lys | Arg | Ala | Val | Ser 1315 | Thr | Trp | Ile | Glu | Ile 1320 | Gln | Pro | Gly |
| Val | Tyr 1325 | Val | Tyr | Phe | Asp | Lys 1330 | Asn | Gly | Leu | Ala | Tyr 1335 | Pro | Pro | Arg |
| Val | Leu 1340 | Asn | | | | | | | | | | | | |

ENZYMATIC PRODUCTION OF ALPHA-1,3-GLUCAN

This application claims the benefit of U.S. Provisional Application Nos. 62/509,915 (filed May 23, 2017) and 62/519,217 (filed Jun. 14, 2017), which are both incorporated herein by reference in their entirety.

FIELD

This present disclosure is in the field of enzymatic processes. For example, the disclosure pertains to glucosyltransferase reactions comprising added oligosaccharides.

REFERENCE TO SEQUENCE LISTING SUBMITTED ELECTRONICALLY

The official copy of the sequence listing is submitted electronically via EFS-Web as an ASCII formatted sequence listing with a file named 20180522_CL6007USNP_SequenceListing created on May 18, 2018, and having a size of about 157 kilobytes and is filed concurrently with the specification. The sequence listing contained in this ASCII-formatted document is part of the specification and is herein incorporated by reference in its entirety.

BACKGROUND

Driven by a desire to use polysaccharides in various applications, researchers have explored for polysaccharides that are biodegradable and that can be made economically from renewably sourced feedstocks. One such polysaccharide is alpha-1,3-glucan, an insoluble glucan polymer characterized by having alpha-1,3-glycosidic linkages. This polymer has been prepared, for example, using a glucosyltransferase enzyme isolated from *Streptococcus salivarius* (Simpson et al., Microbiology 141:1451-1460, 1995). Also for example, U.S. Pat. No. 7,000,000 disclosed the preparation of a spun fiber from enzymatically produced poly alpha-1,3-glucan.

Enzymatic synthesis of various glucan polymers has been performed in reactions in which polysaccharides (e.g., dextran) or oligosaccharides (e.g., from hydrolyzed polysaccharide) have been added to affect glucosyltransferase function (e.g., Koga et al., 1983, *J. Gen. Microbiol.* 129:751-754; Komatsu et al., 2011, *FEBS J.* 278:531-540; Simpson et al.; O'Brien et al., U.S. Pat. No. 8,642,757). Despite these disclosures, there is little understanding with regard to modulating glucosyltransferase reactions for insoluble alpha-1,3-glucan synthesis.

SUMMARY

In one embodiment, the present disclosure concerns a method for producing insoluble alpha-1,3-glucan comprising:
(a) providing oligosaccharides that:
  (i) comprise alpha-1,3 and alpha-1,6 glycosidic linkages, and/or
  (ii) are produced from a glucosyltransferase reaction;
(b) contacting at least water, sucrose, the oligosaccharides, and a glucosyltransferase enzyme that synthesizes insoluble alpha-1,3-glucan, wherein insoluble alpha-1,3-glucan is produced; and
(c) optionally, isolating the insoluble alpha-1,3-glucan produced in step (b).

In another embodiment, the present disclosure concerns a reaction composition for producing insoluble alpha-1,3-glucan, the reaction composition comprising at least water, sucrose, a glucosyltransferase enzyme that synthesizes insoluble alpha-1,3-glucan, and oligosaccharides, wherein the oligosaccharides are added during preparation of the reaction composition and (i) comprise alpha-1,3 and alpha-1,6 glycosidic linkages, and/or (ii) are produced from a glucosyltransferase reaction, wherein insoluble alpha-1,3-glucan is produced in the reaction composition.

In another embodiment, the present disclosure concerns a composition comprising insoluble alpha-1,3-glucan produced according to any method herein of producing insoluble alpha-1,3-glucan.

BRIEF DESCRIPTION OF THE DRAWINGS AND SEQUENCES

FIG. 1: $^1$H-NMR spectra of a concentrated oligosaccharide preparation (see Example 2).

Figure 2:
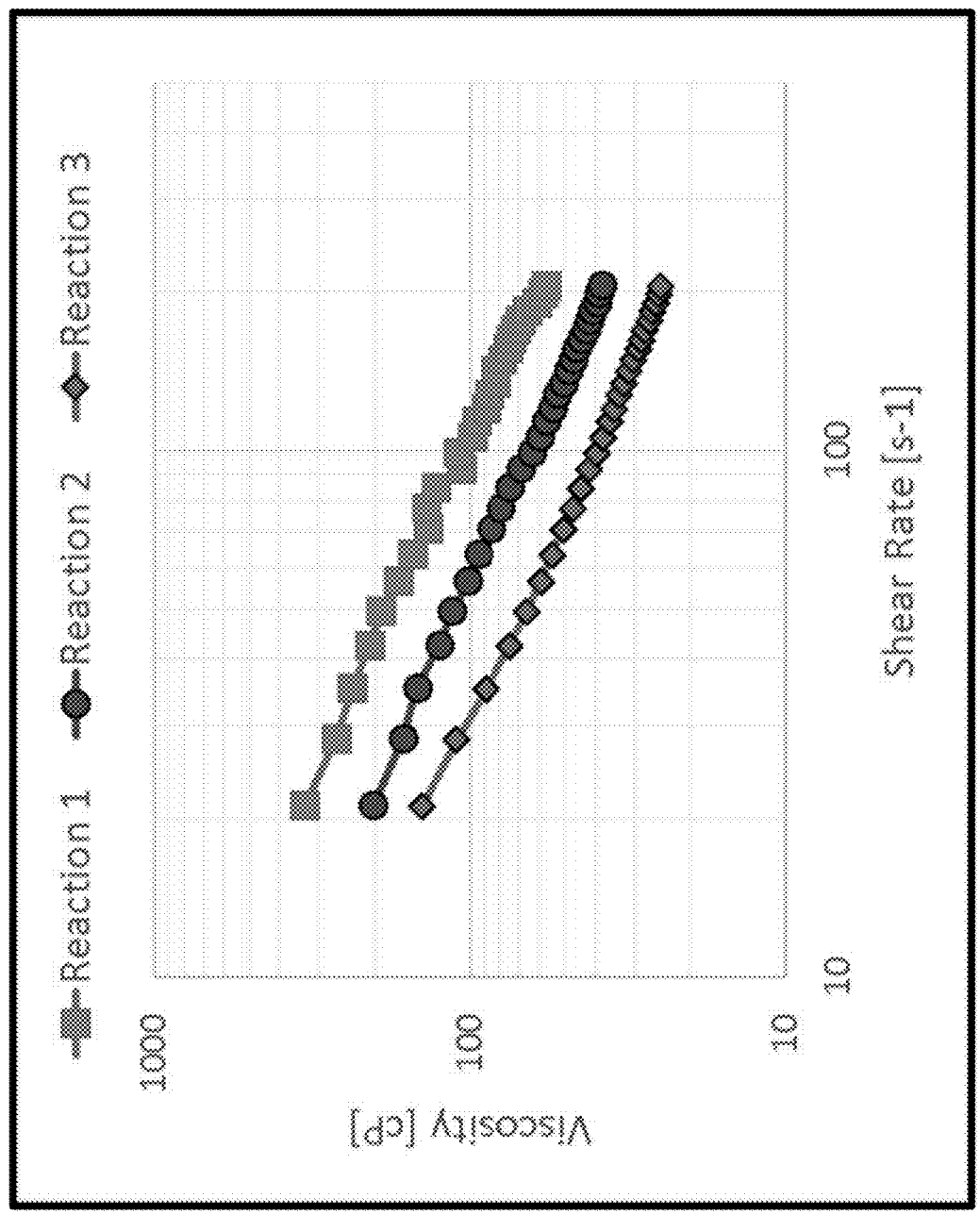

FIG. 2: The graph shows the aqueous slurry viscosity of each alpha-1,3-glucan product made in three successive reactions, where the second and third reactions incorporated filtrate derived from the first and second reactions, respectively (see Example 10). Squares, circles and diamonds indicate, respectively, viscosity measurements taken with aqueous slurries of alpha-1,3-glucan produced in first, second and third reactions. Shear rate units are in 1/s (shown as "s−1").

TABLE 1

Summary of Nucleic Acid and Protein Sequence Identification Numbers

| Description | Nucleic acid SEQ ID NO. | Protein SEQ ID NO. |
|---|---|---|
| GTFJ or GTF 7527, *Streptococcus salivarius*. The first 42 amino acids of the protein are deleted compared to GENBANK Identification No. 47527; a start methionine is included. | $1^a$ | 2 (1477 aa) |
| GTF 0874, *Streptococcus sobrinus*. The first 156 amino acids of the protein are deleted compared to GENBANK Identification No. 450874; a start methionine is included. | $3^a$ | 4 (1435 aa) |
| GTF 1724, *Streptococcus downei*. The first 162 amino acids of the protein are deleted compared to GENBANK Identification No. 121724; a start methionine is included. | $5^a$ | 6 (1436 aa) |
| GTF 1724-T1, *Streptococcus downei*. The first 217 amino acids and the last 530 amino acids of the protein are deleted compared to GENBANK Identification No. 121724; a start methionine is included. | | 7 (851 aa) |
| GTFJ-T1 or GTF 7527-T1, *Streptococcus salivarius*. The first 230 amino acids and the last 384 amino acids of the protein are deleted compared to GENBANK Identification No. 47527; a start methionine is included. | | 8 (905 aa) |
| GTF 6855, *Streptococcus salivarius* SK126. The first 178 amino acids of the protein are deleted compared to GENBANK Identification No. 228476855; a start methionine is included. | | 9 (1341 aa) |
| GTF 5926, *Streptococcus dentirousetti*. The first 144 amino acids of the protein are deleted compared to GENBANK Identification No. 167735926; a start methionine is included. | | 10 (1323 aa) |
| GTF 2765, unknown *Streptococcus* sp. C150. The first 193 amino acids of the protein are deleted compared to GENBANK Identification No. 322372765; a start methionine is included. | | 11 (1340 aa) |

TABLE 1-continued

Summary of Nucleic Acid and Protein
Sequence Identification Numbers

| Description | Nucleic acid SEQ ID NO. | Protein SEQ ID NO. |
|---|---|---|
| GTF 0427, *Streptococcus sobrinus*. The first 156 amino acids of the protein are deleted compared to GENBANK Identification No. 940427; a start methionine is included. | 5 | 12 (1435 aa) |
| GTF 2919, *Streptococcus salivarius* PS4. The first 92 amino acids of the protein are deleted compared to GENBANK Identification No. 383282919; a start methionine is included. | | 13 (1340 aa) |
| GTF 2678, *Streptococcus salivarius* K12. The first 188 amino acids of the protein are deleted compared to GENBANK Identification No. 400182678; a start methionine is included. | | 14 (1341 aa) |
| GTF 3929, *Streptococcus salivarius* JIM8777. The first 178 amino acids of the protein are deleted compared to GENBANK Identification No. 387783929; a start methionine is included. | | 15 (1341 aa) |
| "GTF 7527-short" (shorter version of GTFJ), *Streptococcus salivarius*. The first 178 amino acids of the protein are deleted compared to GENBANK Identification No. 47527; a start methionine is included. | | 16 (1341 aa) |

*a* This DNA coding sequence is codon-optimized for expression in *E. coli* and is merely disclosed as an example of a suitable coding sequence.

DETAILED DESCRIPTION

The disclosures of all cited patent and non-patent literature are incorporated herein by reference in their entirety.

Unless otherwise disclosed, the terms "a" and "an" as used herein are intended to encompass one or more (i.e., at least one) of a referenced feature.

Where present, all ranges are inclusive and combinable, except as otherwise noted. For example, when a range of "1 to 5" is recited, the recited range should be construed as including ranges "1 to 4", "1 to 3", "1-2", "1-2 & 4-5", "1-3 & 5", and the like.

The term "saccharide" as used herein refers to monosaccharides and/or disaccharides/oligosaccharides, unless otherwise noted. A "disaccharide" herein refers to a carbohydrate having two monosaccharides joined by a glycosidic linkage. An "oligosaccharide" herein can refer to a carbohydrate having 2 to 15 monosaccharides, for example, joined by glycosidic linkages. An oligosaccharide can also be referred to as an "oligomer". Monosaccharides (e.g., glucose and/or fructose) comprised within disaccharides/oligosaccharides can be referred to as "monomer units", "monosaccharide units", or other like terms.

The terms "alpha-glucan", "alpha-glucan polymer" and the like are used interchangeably herein. An alpha-glucan is a polymer comprising glucose monomeric units linked together by alpha-glycosidic linkages. In typical embodiments, an alpha-glucan herein comprises at least about 80%, 81%, 82%, 83%, 84%, 85%, 86%, 87%, 88%, 89%, 90%, 91%, 92%, 93%, 94%, 95%, 96%, 97%, 98%, 99%, or 100% alpha-glycosidic linkages. Alpha-1,3-glucan is an example of an alpha-glucan.

The terms "alpha-1,3-glucan", "poly alpha-1,3-glucan", "alpha-1,3-glucan polymer" and the like are used interchangeably herein. Alpha-1,3-glucan is a polymer comprising glucose monomeric units linked together by glycosidic linkages (i.e., glucosidic linkages), typically wherein at least about 50% of the glycosidic linkages are alpha-1,3-glycosidic linkages. Alpha-1,3-glucan in certain embodiments comprises at least about 90% or 95% alpha-1,3 glycosidic linkages. Most or all of the other linkages in alpha-1,3-glucan herein typically are alpha-1,6, though some linkages may also be alpha-1,2 and/or alpha-1,4.

The terms "glycosidic linkage", "linkage", "glycosidic bond" and the like are used interchangeably herein and refer to the type of covalent bond that joins a carbohydrate (sugar) molecule to another carbohydrate molecule. All glycosidic linkages disclosed herein are alpha-glucosidic linkages, except as otherwise noted. A "glucosidic linkage" refers to a glycosidic linkage between an alpha-D-glucose and another carbohydrate molecule. "Alpha-D-glucose" herein is also be referred to as "glucose". The terms "alpha-1,3 glucosyl-glucose linkage", "alpha-1,3 glucose-glucose linkage" and "glucose-alpha 1,3-glucose" herein refer to an alpha-1,3 glycosidic linkage. The terms "alpha-1,6 glucosyl-glucose linkage", "alpha-1,6 glucose-glucose linkage" and "glucose-alpha 1,6-glucose" herein refer to an alpha-1,6 glycosidic linkage.

The glycosidic linkage profile of any polysaccharide herein (e.g., alpha-1,3-glucan, oligosaccharides) can be determined using any method known in the art. For example, a linkage profile can be determined using methods using nuclear magnetic resonance (NMR) spectroscopy (e.g., $^{13}C$ NMR or $^{1}H$ NMR). These and other methods that can be used are disclosed in, for example, *Food Carbohydrates: Chemistry, Physical Properties, and Applications* (S. W. Cui, Ed., Chapter 3, S. W. Cui, Structural Analysis of Polysaccharides, Taylor & Francis Group LLC, Boca Raton, Fla., 2005), which is incorporated herein by reference.

The "molecular weight" of large alpha-glucan polymers herein can be represented as weight-average molecular weight (Mw) or number-average molecular weight (Mn), the units of which are in Daltons or grams/mole. Alternatively, the molecular weight of large alpha-glucan polymers can be represented as DPw (weight average degree of polymerization) or DPn (number average degree of polymerization). The molecular weight of smaller alpha-glucan polymers such as oligosaccharides typically can be provided as "DP" (degree of polymerization), if desired, which simply refers to the number of glucoses comprised within the alpha-glucan. Various means are known in the art for calculating these various molecular weight measurements such as with high-pressure liquid chromatography (HPLC), size exclusion chromatography (SEC), or gel permeation chromatography (GPC).

The terms "glucosyltransferase", "glucosyltransferase enzyme", "GTF", "glucansucrase" and the like are used interchangeably herein. The activity of a glucosyltransferase herein catalyzes the reaction of the substrate sucrose to make the products alpha-glucan and fructose. Other products (by-products) of a glucosyltransferase reaction can include glucose, various soluble gluco-oligosaccharides, and leucrose. Wild type forms of glucosyltransferase enzymes generally contain (in the N-terminal to C-terminal direction) a signal peptide (which is typically removed by cleavage processes), a variable domain, a catalytic domain, and a glucan-binding domain. A glucosyltransferase herein is classified under the glycoside hydrolase family 70 (GH70) according to the CAZy (Carbohydrate-Active EnZymes) database (Cantarel et al., *Nucleic Acids Res.* 37:D233-238, 2009).

The term "glucosyltransferase catalytic domain" herein refers to the domain of a glucosyltransferase enzyme that provides alpha-glucan-synthesizing activity to a glucosyltransferase enzyme. A glucosyltransferase catalytic domain typically does not require the presence of any other domains to have this activity.

The terms "enzymatic reaction", "glucosyltransferase reaction", "glucan synthesis reaction", "reaction composition", "reaction formulation" and the like are used interchangeably herein and generally refer to a reaction that initially comprises water, sucrose, at least one active glucosyltransferase enzyme, and optionally other components. Components that can be further present in a glucosyltransferase reaction typically after it has commenced include fructose, glucose, leucrose, soluble gluco-oligosaccharides (e.g., DP2-DP7) (such may be considered as products or by-products, depending on the glucosyltransferase used), and/or insoluble alpha-glucan product(s) of DP8 or higher (e.g., DP100 and higher). It would be understood that certain glucan products, such as alpha-1,3-glucan with a degree of polymerization (DP) of at least 8 or 9, are water-insoluble ("insoluble alpha-1,3-glucan) and thus not dissolved in a glucan synthesis reaction, but rather may be present out of solution (e.g., by virtue of having precipitated from the reaction). It is in a glucan synthesis reaction where the step of contacting water, sucrose and a glucosyltransferase enzyme is performed. The term "under suitable reaction conditions" as used herein refers to reaction conditions that support conversion of sucrose to alpha-glucan product(s) via glucosyltransferase enzyme activity.

A "control" reaction as used herein can refer to a glucosyltransferase reaction to which no oligosaccharides comprising (collectively comprising) alpha-1,3 and alpha-1,6 glycosidic linkages have been directly added to the reaction. All the other features (e.g., sucrose concentration, temperature, pH, type of GTF) of a control reaction solution can be the same as the reaction composition to which it is being compared.

The "percent dry solids" (percent DS) of a solution herein (e.g., soluble fraction, aqueous composition) refers to the wt % of all the materials (i.e., the solids) dissolved in the solution. For example, a 100 g solution with 10 wt % DS comprises 10 g of dissolved material.

The "yield" of alpha-1,3-glucan by a glucosyltransferase reaction in certain embodiments represents the weight of alpha-1,3-glucan product expressed as a percentage of the weight of sucrose substrate that is converted in the reaction. For example, if 100 g of sucrose in a reaction solution is converted to products, and 10 g of the products is alpha-1,3-glucan, the yield of the alpha-1,3-glucan would be 10%. The "yield" of alpha-1,3-glucan by a glucosyltransferase reaction in some aspects represents the molar yield based on the converted sucrose. The molar yield of an alpha-glucan product can be calculated based on the moles of the alpha-glucan product divided by the moles of the sucrose converted. Moles of converted sucrose can be calculated as follows: (mass of initial sucrose−mass of final sucrose)/ molecular weight of sucrose [342 g/mol]. These yield calculations (yield based on weight or moles) can be considered as measures of selectivity of the reaction toward alpha-1,3-glucan. In some aspects, the "yield" of an alpha-glucan product in a glucosyltransferase reaction can be based on the glucosyl component of the reaction. Such a yield (yield based on glucosyl) can be measured using the following formula:

$$\text{Alpha-Glucan Yield} = ((IS/2-(FS/2+LE/2+GL+SO))/(IS/2-FS/2)) \times 100\%.$$

The fructose balance of a glucosyltransferase reaction can be measured to ensure that HPLC data, if applicable, are not out of range (90-110% is considered acceptable). Fructose balance can be measured using the following formula:

$$\text{Fructose Balance} = ((180/342 \times (FS+LE) + FR)/(180/342 \times IS)) \times 100\%.$$

In the above two formulae, IS is [Initial Sucrose], FS is [Final Sucrose], LE is [Leucrose], GL is [Glucose], SO is [Soluble Oligomers] (gluco-oligosaccharides), and FR is [Fructose] (all concentrations in units of grams/L and as measured by HPLC, for example).

The term "relative reaction rate" as used herein refers to the rate of a particular glucan synthesis reaction as compared to another glucan synthesis reaction. For example, if reaction A has a rate of x, and reaction B has a rate of y, then the relative reaction rate of reaction A with respect to the reaction rate of reaction B can be expressed as x/y (x divided by y). The terms "reaction rate" and "rate of reaction" are used interchangeably herein to refer to the change in concentration/amount of reactant(s) or the change in concentration/amount of product(s) per unit time per unit of enzyme. As GTF enzymes are known to follow Michaelis-Menten kinetics, these rates are typically measured at the beginning of polymerization when the amount of sucrose is well above the Km for the enzyme. In this case, the rate is typically measured when the amount of sucrose in the reaction is above at least about 50 g/L sucrose. Preferred reactant and product herein of a glucan synthesis reaction are, respectively, sucrose and alpha-1,3-glucan.

A "soluble fraction" or "soluble portion" of a glucosyltransferase reaction herein refers to a liquid solution portion of the glucosyltransferase reaction. A soluble fraction can be a portion of, or all of, the liquid solution from a glucosyltransferase reaction, and typically has been separated from an insoluble glucan product synthesized in the reaction. A soluble fraction can alternatively be referred to as a "mother liquor". An example of a soluble fraction is a filtrate of a glucosyltransferase reaction. Since a soluble fraction can contain dissolved sugars such as sucrose, fructose, glucose, leucrose, soluble gluco-oligosaccharides, a fraction can also be referred to as a "mixed sugar solution" derived from a glucosyltransferase reaction. A soluble fraction herein can remain unprocessed following its acquisition, or alternatively, it can be subjected to one or more processing steps as disclosed herein.

The terms "filtrate", "glucan reaction filtrate", and the like are used interchangeably herein and refer to a soluble fraction that has been filtered away from an insoluble glucan product synthesized in a glucosyltransferase reaction.

The terms "percent by volume", "volume percent", "vol %", "v/v %" and the like are used interchangeably herein. The percent by volume of a solute in a solution can be determined using the formula: [(volume of solute)/(volume of solution)]×100%.

The terms "percent by weight", "weight percentage (wt %)", "weight-weight percentage (% w/w)" and the like are used interchangeably herein. Percent by weight refers to the percentage of a material on a mass basis as it is comprised in a composition, mixture, or solution.

The term "aqueous conditions" and like terms herein refer to a solution or mixture in which the solvent is at least about 60 wt % water, for example. A glucosyltransferase reaction herein is performed under aqueous conditions.

A glucan that is "insoluble", "aqueous-insoluble", "water-insoluble" (and like terms) (e.g., insoluble alpha-1,3-glucan) does not dissolve (or does not appreciably dissolve) in water or other aqueous conditions, optionally where the aqueous conditions are further characterized to have a pH of 4-9 (e.g., 6-8) and/or temperature of about 1 to 85° C. (e.g., 20-25° C.). In contrast, glucans such as certain oligosaccharides herein that are "soluble", "aqueous-soluble", "water-soluble" and the like appreciably dissolve under these conditions.

An "aqueous composition" herein has a liquid component that comprises at least about 10 wt % water, for example (e.g., liquid component can be at least about 70%, 80%, 90%, 95% water, or 100% water). Examples of aqueous compositions include mixtures, solutions, dispersions (e.g., colloidal dispersions), suspensions and emulsions, for example. Aqueous compositions in certain embodiments comprise alpha-1,3-glucan as produced herein that is mixed (e.g., by homogenization) or dissolved (e.g., via dissolution under caustic aqueous conditions such as at a pH of at least 11.0 [as provided using an alkaline solute such NaOH or KOH, for example]) in the aqueous composition. A "non-aqueous composition" herein can be "dry" (e.g., comprises no more than 2.0, 1.5, 1.0, 0.5, 0.25, 0.10, 0.05, or 0.01 wt % water) and/or comprise a non-aqueous liquid component (e.g., an organic liquid that can dissolve alpha-1,3-glucan such as N,N-dimethylacetamide (DMAc)/0.5%-5% LiCl).

The term "purified" herein can characterize an oligosaccharide preparation comprising no more than 25% (dry weight basis) of saccharides and/or other non-salt/non-buffer material not embraced by the above definition of oligosaccharides. As the definition implies, a purified oligosaccharide preparation can optionally comprise salts and/or buffers, the level of neither of which are determinative of oligosaccharide purity. The term "unpurified" herein can characterize an oligosaccharide preparation comprising more than 25% (dry weight basis) saccharides, and/or other non-salt/non-buffer material, not embraced by the above definition of oligosaccharides.

The term "viscosity" as used herein refers to the measure of the extent to which a fluid (aqueous or non-aqueous) resists a force tending to cause it to flow. Various units of viscosity that can be used herein include centipoise (cP, cps) and Pascal-second (Pa-s), for example. A centipoise is one one-hundredth of a poise; one poise is equal to 0.100 kg·m$^{-1}$s$^{-1}$. Viscosity can be reported as "intrinsic viscosity" (IV, η, units of mL/g) in some aspects; this term refers to a measure of the contribution of a glucan polymer to the viscosity of a liquid (e.g., solution) comprising the glucan polymer.

The term "increased" as used herein can refer to a quantity or activity that is at least about 1%, 2%, 3%, 4%, 5%, 6%, 7%, 8%, 9%, 10%, 11%, 12%, 13%, 14%, 15%, 16%, 17%, 18%, 19%, 20%, 50%, 100%, or 200% more than the quantity or activity for which the increased quantity or activity is being compared. The terms "increased", "elevated", "enhanced", "greater than", "improved" and the like are used interchangeably herein. These terms can be used to characterize the "over-expression" or "up-regulation" of a polynucleotide encoding a protein, for example.

The terms "sequence identity", "identity" and the like as used herein with respect to polynucleotide or polypeptide sequences herein refer to the nucleic acid residues or amino acid residues in two sequences that are the same when aligned for maximum correspondence over a specified comparison window. Thus, "percentage of sequence identity", "percent identity" and the like refer to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. It would be understood that, when calculating sequence identity between a DNA sequence and an RNA sequence, T residues of the DNA sequence align with, and can be considered "identical" with, U residues of the RNA sequence. For purposes of determining "percent complementarity" of first and second polynucleotides, one can obtain this by determining (i) the percent identity between the first polynucleotide and the complement sequence of the second polynucleotide (or vice versa), for example, and/or (ii) the percentage of bases between the first and second polynucleotides that would create canonical Watson and Crick base pairs.

Percent identity can be readily determined by any known method, including but not limited to those described in: 1) *Computational Molecular Biology* (Lesk, A. M., Ed.) Oxford University: NY (1988); 2) *Biocomputing: Informatics and Genome Projects* (Smith, D. W., Ed.) Academic: NY (1993); 3) *Computer Analysis of Sequence Data, Part I* (Griffin, A. M., and Griffin, H. G., Eds.) Humana: NJ (1994); 4) *Sequence Analysis in Molecular Biology* (von Heinje, G., Ed.) Academic (1987); and 5) *Sequence Analysis Primer* (Gribskov, M. and Devereux, J., Eds.) Stockton: NY (1991), all of which are incorporated herein by reference.

Preferred methods for determining percent identity are designed to give the best match between the sequences tested. Methods of determining identity and similarity are codified in publicly available computer programs, for example. Sequence alignments and percent identity calculations can be performed using the MEGALIGN program of the LASERGENE bioinformatics computing suite (DNASTAR Inc., Madison, Wis.), for example. Multiple alignment of sequences can be performed, for example, using the Clustal method of alignment which encompasses several varieties of the algorithm including the Clustal V method of alignment (described by Higgins and Sharp, *CABIOS.* 5:151-153 (1989); Higgins, D. G. et al., *Comput. Appl. Biosci.*, 8:189-191 (1992)) and found in the MEGALIGN v8.0 program of the LASERGENE bioinformatics computing suite (DNASTAR Inc.). For multiple alignments, the default values can correspond to GAP PENALTY=10 and GAP LENGTH PENALTY=10. Default parameters for pairwise alignments and calculation of percent identity of protein sequences using the Clustal method can be KTUPLE=1, GAP PENALTY=3, WINDOW=5 and DIAGONALS SAVED=5. For nucleic acids, these parameters can be KTUPLE=2, GAP PENALTY=5, WINDOW=4 and DIAGONALS SAVED=4. Additionally, the Clustal W method of alignment can be used (described by Higgins and Sharp, *CABIOS.* 5:151-153 (1989); Higgins, D. G. et al., *Comput. Appl. Biosci.* 8:189-191 (1992); Thompson, J. D. et al, *Nucleic Acids Research,* 22 (22): 4673-4680, 1994) and found in the MEGALIGN v8.0 program of the LASERGENE bioinformatics computing suite (DNASTAR Inc.). Default parameters for multiple alignment (protein/nucleic acid) can be: GAP PENALTY=10/15, GAP LENGTH PENALTY=0.2/6.66, Delay Divergen Seqs (%)=30/30, DNA Transition Weight=0.5, Protein Weight Matrix=Gonnet Series, DNA Weight Matrix=IUB.

Various polypeptide amino acid sequences and polynucleotide sequences are disclosed herein as features of certain embodiments. Variants of these sequences that are at least about 70-85%, 85-90%, or 90%-95% identical to the sequences disclosed herein can be used or referenced. Alternatively, a variant amino acid sequence or polynucleotide sequence can have at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identity with a sequence disclosed herein. The variant amino acid sequence or polynucleotide sequence has the same function/activity of the disclosed sequence, or at least about 80%, 81%, 82%, 83%, 84%, 85%, 86%, 87%, 88%, 89%, 90%, 91%, 92%, 93%, 94%, 95%, 96%, 97%, 98%, or 99% of the function/activity of the disclosed sequence. Any polypeptide amino acid sequence disclosed herein not beginning with a methionine can typically further comprise at least a start-methionine at the N-terminus of the amino acid sequence. In contrast, any polypeptide amino acid sequence disclosed herein beginning with a methionine can optionally lack such a methionine residue.

It is believed that the compositions (e.g., insoluble alpha-1,3-glucan in certain embodiments) and glucosyltransferase reactions/methods disclosed herein are synthetic and non-naturally occurring. Thus, such aspects herein can optionally be characterized as being "isolated", which means for example that they can be carried out in a manner that does not occur in nature. It is further believed that the properties/effects of the aforementioned subject matter are not naturally occurring.

It is now disclosed that yield and other product benefits can be realized when applying certain oligosaccharides to glucosyltransferase reactions for insoluble alpha-1,3-glucan production.

Embodiments of the present disclosure concern a method for producing insoluble alpha-1,3-glucan. The method comprises:
(a) providing oligosaccharides that:
    (i) comprise alpha-1,3 and alpha-1,6 glycosidic linkages, and/or
    (ii) are produced from a glucosyltransferase reaction; and
(b) contacting at least water, sucrose, a glucosyltransferase enzyme, and the oligosaccharides provided in step (a). Insoluble alpha-1,3-glucan is produced in this method. In certain embodiments, the yield of insoluble alpha-1,3-glucan product is increased compared to the yield of insoluble alpha-1,3-glucan that would have been produced if step (b) was performed without the oligosaccharides provided in step (a). Insoluble alpha-1,3-glucan produced in step (b) of the method can optionally be isolated.

Significantly, oligosaccharides comprising alpha-1,3 and alpha-1,6 glycosidic linkages are disclosed herein to modulate the activity of glucosyltransferase enzymes that produce insoluble alpha-1,3-glucan. Such oligosaccharides can optionally be derived as a by-product of a glucosyltransferase reaction as disclosed herein. Thus, the disclosed method in certain embodiments represents an advantageous way to recycle oligosaccharide by-products of a glucosyltransferase reaction. Also of significance herein is that oligosaccharide by-products are useful for modulating glucosyltransferase activity even when provided in an unpurified state such as in a filtrate obtained from a glucosyltransferase reaction.

Oligosaccharides in certain embodiments of the present disclosure comprise alpha-1,3 glycosidic linkages and alpha-1,6 glycosidic linkages. For example, oligosaccharides herein can comprise about 60-99%, 60-95%, 70-90%, or 80-90% alpha-1,3 glycosidic linkages, and about 1-40%, 5-40%, 10-30%, or 1-10% alpha-1,6 glycosidic linkages. Still, in some aspects, oligosaccharides can comprise about 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% (or range between any two of these values) alpha-1,3 glycosidic linkages, and about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, or 40% (or range between any two of these values) alpha-1,6 glycosidic linkages. Such a linkage profile can characterize oligosaccharides of any molecular weight herein (e.g., DP2-7, DP2-8, DP2-9, or DP2-10). The aforementioned linkage profiles can optionally characterize gluco-oligosaccharides.

Oligosaccharides herein can, for instance, "collectively comprise" any of the foregoing linkage profiles. By "collectively comprise", it is meant that the linkage profile of a mixture of various oligosaccharides is based on the combination of all the linkages present in the mixture. Oligosaccharides useful herein can therefore comprise particular oligosaccharide species containing only alpha-1,3 glycosidic linkages, only alpha-1,6 glycosidic linkages, and/or both alpha-1,3 and alpha-1,6 glycosidic linkages, just so long that the total linkage profile of all the oligosaccharide species present falls under any of the foregoing linkage profiles (e.g., ~78% alpha-1,3 linkages and ~22% alpha-1,6 linkages, or ~87-88% alpha-1,3 linkages and ~7% alpha-1,6 linkages). Oligosaccharides in certain aspects do not comprise/collectively comprise 100% alpha-1,3 glycosidic linkages or 100% alpha-1,6 glycosidic linkages.

Gluco-oligosaccharides herein preferably contain mostly alpha-1,3 and alpha-1,6 glycosidic linkages. For example, at least about 95%, 96%, 97%, 98%, 99%, or 100% of the total linkages of the oligosaccharides are alpha-1,3 and alpha-1,6 glycosidic linkages. Other linkages, if present in the oligosaccharides, may be alpha-1,4 (e.g., ≤1.5% or 1%) or alpha-1,2 (e.g., ≤1% or 0.7%) glycosidic linkages, for example.

Oligosaccharides herein can have a degree of polymerization (DP) of 2 to 15 in some aspects. As examples, the oligosaccharides can have a DP of 2-6, 2-7, 2-8, 2-9, 2-10, 2-11, 2-12, 2-13, 2-14, or 2-15. As would be understood in the art, a group of oligosaccharides herein can be referenced with respect to a DP number or range, which specifies the number or range of monomeric units in individual oligosaccharide species in the group. For example, DP2-7 oligosaccharides typically comprise a mixture of DP2, DP3, DP4, DP5, DP6 and DP7 oligosaccharides. The aforementioned oligosaccharides can optionally be referred to as gluco-oligosaccharides.

The distribution of oligosaccharides in a composition used to provide oligosaccharides herein can vary. For example, a composition comprising oligosaccharides of DP 2-7 can comprise oligosaccharides having a distribution profile that is the same or similar to that disclosed below in Table 5. Thus, a composition comprising DP2-7 oligosaccharides can comprise, for example, about 5-15 wt % (e.g., ~9-11 wt %) DP2, about 19-29 wt % (e.g., ~23-25 wt %) DP3, about 27-37 wt % (e.g., ~31-33 wt %) DP4, about 15-25 wt % (e.g., ~19-21 wt %) DP5, about 3-13 wt % (e.g., ~7-9 wt %) DP6, and about 1 to 10 wt % (e.g., ~4-6 wt %) DP7 oligosaccharides on the basis of the saccharide components in the composition or on a dry weight basis. In some aspects, a composition comprising oligosaccharides of DP 2-7 can comprise oligosaccharides having a distribution profile that is the same or similar to that disclosed below in Table 16. Thus, a composition comprising DP2-7 oligosaccharides can comprise, for example, about 6-16 wt % (e.g., ~10-12 wt %) DP2, about 18-28 wt % (e.g., ~22-24 wt %) DP3, about 23-33 wt % (e.g., ~27-29 wt %) DP4, about 16-26 wt % (e.g., ~20-22 wt %) DP5, about 7-17 wt % (e.g., ~11-13 wt %) DP6, and about 1 to 10 wt % (e.g., ~4-6 wt %) DP7 oligosaccharides on the basis of the saccharide components in the composition or on a dry weight basis. The exact DP distribution is not believed to be critical to the present disclosure; other distributions should provide the same behavior described herein.

In certain embodiments of the present disclosure, the oligosaccharides can be purified or unpurified. Purified oligosaccharides can be provided using any suitable means known in the art, such as via chromatography as disclosed in the below Examples, or by following the disclosure of European Patent Publ. No. EP2292803B1, which is incorporated herein by reference. Purified oligosaccharides can be provided, for example, in a dry form or an aqueous form (aqueous solution), either of which may optionally also contain one or more salts (e.g., NaCl) and/or buffers. A purified oligosaccharide preparation in certain embodiments can comprise less than about 25, 20, 15, 10, 5, 2.5, 2, 1.5, 1.0, 0.5, or 0.1 wt % of (i) saccharides that are not embraced by the definition of oligosaccharides as disclosed herein (e.g., oligosaccharides herein are not monosaccharides or DP11+ saccharides) and/or (ii) other non-salt/non-buffer material.

Unpurified oligosaccharides can be used in certain embodiments of the present disclosure. An unpurified oligosaccharide preparation can comprise, for example, more than about 2, 5, 10, 20, 30, 40, 50, 60, 70, 80, 90, or 95% wt % saccharides, and/or other non-salt/non-buffer material, not embraced by the definition of oligosaccharides as disclosed herein. An example of an unpurified oligosaccharide preparation herein is a soluble fraction (e.g., filtrate) from a glucosyltransferase reaction. Other "non-salt/non-buffer material" that can be present in a soluble fraction herein include sucrose, fructose, glucose, leucrose, and glucosyltransferase protein, for example.

Oligosaccharides provided in step (a) of the disclosed method can be produced from ("derived from", derivable or obtainable from) a glucosyltransferase reaction. The oligosaccharides can be a by-product of a glucosyltransferase reaction, for example. Such a by-product can be from a glucosyltransferase reaction that synthesizes insoluble alpha-1,3-glucan in certain embodiments.

A glucosyltransferase reaction from which oligosaccharides herein can be produced generally refers to an aqueous composition comprising at least sucrose, water and one active glucosyltransferase enzyme, and optionally other components. Other components that can be in a glucosyltransferase reaction include at least fructose, glucose, leucrose, and gluco-oligosaccharides. It would be understood that certain glucan products, such as alpha-1,3-glucan with a DP of at least 8 or 9, can be water-insoluble and thus are not dissolved in a glucosyltransferase reaction, but rather present out of solution. Thus, oligosaccharides herein can be derived from a glucosyltransferase reaction that produces an insoluble glucan product (e.g., alpha-1,3-glucan).

A glucosyltransferase reaction from which oligosaccharides may be derived can comprise one or more of the following types of glucosyltransferase enzymes: a GTF that produces alpha-1,3-glucan with at least 50% alpha-1,3 glycosidic linkages (e.g., GTF's disclosed herein that can also be used as a GTF in the disclosed method itself), mutansucrase, dextransucrase, reuteransucrase, alternansucrase. In certain embodiments, oligosaccharides are from a reaction comprising only one or two glucosyltransferases that produce insoluble alpha-1,3-glucan.

Oligosaccharides herein are typically derived from a glucosyltransferase reaction at a stage in which by-product oligosaccharides have formed in the reaction. Oligosaccharides form throughout a polymerization reaction. For example, oligosaccharides can be from a glucosyltransferase reaction that is only partially complete to nearly complete (e.g., 80 to 90% complete) or at completion (e.g. >95% complete), where completion is defined as the amount of sucrose consumed divided by the total amount of sucrose fed to the polymerization.

Oligosaccharides in certain embodiments of the present disclosure can be provided as a soluble fraction of a glucosyltransferase reaction. A soluble fraction herein can be processed or unprocessed. A soluble fraction can be a portion of, or all of, the liquid solution from a glucosyltransferase reaction. Typically, a soluble fraction has been separated from solid glucan product(s) synthesized in the reaction; this applies to glucan products that are insoluble in water such as alpha-1,3-glucan which fall out of solution during their synthesis. A soluble fraction in certain embodiments of the present disclosure is from a glucosyltransferase reaction that produces alpha-1,3-glucan. However, a soluble fraction can optionally be from a glucosyltransferase reaction that does not produce an insoluble glucan product (e.g., dextran).

The volume of a collected soluble fraction (before optionally processing the soluble fraction, see below) in certain embodiments can be at least about 5%, 10%, 20%, 30%, 40%, 50%, 60%, 70%, 80%, or 90% of the volume of the glucosyltransferase reaction from which it is obtained. Typically, in glucosyltransferase reactions producing an insoluble glucan (e.g., alpha-1,3-glucan), the soluble fraction will be a portion of (not all of) the liquid solution component of the reaction. A soluble fraction can be obtained at a stage of a glucosyltransferase reaction in which by-product oligosaccharides have formed in the reaction. For example, a soluble fraction can be from a glucosyltransferase reaction that is only partially complete to nearly complete (e.g., 80 to 90% complete) or at completion (e.g. >95% complete).

Examples of a soluble fraction of a glucosyltransferase reaction in certain embodiments include filtrates and supernatants. Thus, a soluble fraction herein can be obtained (separated) from a glucosyltransferase reaction using a funnel, filter (e.g., a surface filter such as a rotary vacuum-drum filter, cross-flow filter, screen filter, belt filter, screw press, or filter press with or with membrane squeeze capability; or a depth filter such as a sand filter), centrifuge, and/or any other method or equipment known in the art that allows removal of some or all liquids from solids. Filtration can be by gravity, vacuum, or press filtration, for example. Filtration preferably removes all or most insoluble glucan; any filter material (e.g., cloth, metal screen, or filter paper) with an average pore size (e.g., ~10-50 micron) sufficient to remove solids from liquids can be used. A soluble fraction typically retains all or most of its dissolved components, such as certain by-products of the glucosyltransferase reaction. A filtrate or supernatant herein may be from a glucosyltransferase reaction that synthesizes insoluble alpha-1,3-glucan in certain embodiments.

A soluble fraction herein can be processed, if desired. Examples of processing herein include dilution, concentration, hydrolytic treatment, pH modification, salt modification, and/or buffer modification. Processing can also include deactivating (e.g., heat-deactivation) the glucosyltransferase enzyme(s) used in the glucosyltransferase reaction from which the soluble fraction is obtained. Concentration of a soluble fraction can be performed using any method or equipment known in the art suitable for concentrating a solution. For example, a soluble fraction can be concentrated by evaporation, such as with a rotary evaporator (e.g., temperature of about 40-50° C.). Other suitable types of evaporation equipment include forced circulation or falling film evaporators. A soluble fraction herein can be concentrated down to a volume that is about, or less than about, 75%, 80%, 85%, 90%, or 95%, for example, of the original soluble fraction volume. A concentrated soluble fraction (e.g., concentrated filtrate) can optionally be referred to as a syrup.

A soluble fraction herein can optionally be processed using a hydrolytic treatment. A hydrolytic treatment can be an enzymatic treatment in which the soluble fraction is treated with one or more hydrolytic enzymes, for example. A hydrolytic enzyme can be one that hydrolyzes one or more by-products (e.g., leucrose) of a glucosyltransferase reaction, for example. Examples of useful hydrolytic enzymes herein include alpha-glucosidases such as transglucosidases (EC 2.4.1.24) ("EC" refers to Enzyme Commission number) and glucoamylases (EC 3.2.1.3). Methods of treating a soluble fraction of a glucosyltransferase reaction with any of these enzymes are disclosed in U.S. Patent Appl. Publ. Nos. 2015/0240278 and 2015/0240279, which are incorporated herein by reference.

A soluble fraction herein can be unprocessed, if desired. An unprocessed soluble fraction is one in which the fraction (or portion of a fraction) is isolated from a glucosyltransferase reaction and used in the disclosed method without any sort of modification/processing after isolating the soluble fraction. Examples of an unprocessed soluble fraction include neat filtrate and neat supernatant.

A soluble fraction in certain preferred embodiments of the present disclosure is from an alpha-1,3-glucan synthesis reaction; such a soluble fraction is optionally a filtrate. A soluble fraction of an alpha-1,3-glucan synthesis reaction herein comprises at least water, fructose and one or more types of saccharide (leucrose and/or gluco-oligosaccharides such as DP2-DP7). Other components that may be in this type of soluble fraction include sucrose (i.e., residual sucrose not consumed in the glucosyltransferase reaction), one or more glucosyltransferase enzymes, glucose, buffer, salts, FermaSure®, borates, sodium hydroxide, hydrochloric acid, cell lysate components, proteins and/or nucleic acids, for example. Minimally, the components of a soluble fraction from an alpha-1,3-glucan synthesis reaction herein include water, fructose, glucose, and one or more types of oligosaccharides (leucrose and/or gluco-oligosaccharides such as DP2-DP7, optionally sucrose), for example.

It should be understood that the exact composition of sugars and other material in a soluble fraction of a glucosyltransferase reaction is not believed to be critical for use as a source of oligosaccharides in a method herein. It should also be understood that the ratio of sugars to water (i.e., wt % dry solids), which can be calculated by dividing the mass of starting sugar to total initial reaction solution weight, can be adjusted either by evaporating water, preferably at temperatures below 50° C. under vacuum, or addition of water, without significant impact to the relative distribution of sugars in a soluble fraction of a glucosyltransferase reaction. It is also possible to increase the percentage of sucrose in a soluble fraction by stopping the glucosyltransferase reaction before complete conversion (to glucan) is achieved, either by reducing the pH below the active range of the glucosyltransferase or by thermal deactivation of the glucosyltransferase.

Step (b) of a method herein embodies a glucosyltransferase reaction. Step (a) of providing oligosaccharides is performed before step (b). Thus, the oligosaccharides of step (a) are not provided by virtue of their possible in situ synthesis during step (b). In other words, performing a glucosyltransferase reaction alone in which oligosaccharides are produced as a by-product does not in-and-of-itself constitute performing steps (a) and (b); oligosaccharides must be physically (manually and/or mechanically) added to the glucosyltransferase reaction of step (b) in order to perform step (a). That being said, oligosaccharides produced by a glucosyltransferase reaction embodied by step (b) can be removed from that reaction (purified or unpurified, processed or unprocessed, as above; e.g., as a filtrate) and provided as oligosaccharides for step (a). In such embodiments, steps (a) and (b) can be repeated one or more times, such that the oligosaccharides in each repeat of step (a) are provided from the products resulting from each immediately performed step (b). Steps (a) and (b) can be repeated 1, 2, 3, 4, 5, 6, or more times, for example. Because of this repetition, methods following these embodiments can optionally be referred to as continuous reaction processes and/or oligosaccharide recycling processes. In view of the foregoing, it should be apparent that the glucosyltransferase reaction of step (a)(ii) in some methods herein can be the glucosyltransferase reaction embodied in step (b).

Alternatively, the glucosyltransferase reaction of step (a)(ii) in a method herein can be different (distinct) from the glucosyltransferase reaction embodied in step (b). For example, oligosaccharides can be obtained from a first alpha-1,3-glucan synthesis reaction (e.g., filtrate collected), after which the oligosaccharides are added to a second alpha-1,3-glucan synthesis reaction that is distinct from the first reaction.

A glucosyltransferase enzyme is contacted with at least water, sucrose and added oligosaccharides in step (b) of a method herein. Examples of suitable glucosyltransferase enzymes are provided in the below Examples, and/or are disclosed in U.S. Pat. No. 7,000,000 and U.S. Pat. Appl. Publ. Nos. 2013/0244288, 2013/0244287, 2014/0087431, 2017/0002335 and 2018/0072998 (all of which are incorporated herein by reference).

A glucosyltransferase enzyme in certain embodiments of the present disclosure comprises, or consists of, an amino acid that is at least 90%, 91%, 92%, 93%, 94%, 95%, 96%, 97%, 98%, 99% or 99.5% identical to, or is 100% identical to, SEQ ID NO:2, 4, 6, 7, 8, 9, 10, 11, 12, 13, 14, 15, or 16 (or optionally any of these sequences without the start methionine), for example, wherein the glucosyltransferase enzyme has activity.

All these glucosyltransferases produce alpha-1,3-glucan with a high percentage of alpha-1,3 glycosidic linkages (≥95%) (refer to U.S. Appl. Publ. No. 2014/0087431, for example, which is incorporated herein by reference).

SEQ ID NOs:16 (GTF 7527-short), 14 (GTF 2678), 9 (GTF 6855), 13 (GTF 2919), and 11 (GTF 2765) each represent a glucosyltransferase that, compared to its respective wild type counterpart, lacks the signal peptide domain and all or a substantial portion of the variable domain. Thus, each of these glucosyltransferase enzymes has a catalytic domain followed by a glucan-binding domain. The approximate location of catalytic domain sequences in these enzymes is as follows: 7527-short (residues 54-957 of SEQ ID NO:16), 2678 (residues 55-960 of SEQ ID NO:14), 6855 (residues 55-960 of SEQ ID NO:9), 2919 (residues 55-960 of SEQ ID NO:13), 2765 (residues 55-960 of SEQ ID NO:11). The amino acid sequences of the approximate catalytic domains of GTFs 2678, 6855, 2919 and 2765 have about 94.9%, 99.0%, 95.5% and 96.4% identity, respectively, with the approximate catalytic domain sequence of GTF 7527-short (i.e., amino acids 54-957 of SEQ ID NO:16). All these five glucosyltransferase enzymes can produce alpha-1,3-glucan with about 100% alpha-1,3 linkages and a DPw of at least 400 (data not shown, refer to Table 4 of U.S. Pat. Appl. Publ. No. 2017/0002335, which is incorporated herein by reference). Thus, a glucosyltransferase enzyme in certain embodiments can comprise, or consist of, a glucosyltransferase catalytic domain that is at least 90%, 91%, 92%, 93%, 94%, 95%, 96%, 97%, 98%, 98.5%, 99%, or 99.5% identical to, or is 100% identical to, the amino acid sequence of a catalytic domain of GTF 7527-short, 2678, 6855, 2919, or 2765 (e.g., as listed above).

Although it is believed that a glucosyltransferase enzyme herein need only have a catalytic domain sequence, such as one described above, the glucosyltransferase enzyme can be comprised within a larger amino acid sequence. For example, the catalytic domain may be linked at its C-terminus to a glucan-binding domain, and/or linked at its N-terminus to a variable domain and/or signal peptide.

Still further examples of glucosyltransferase enzymes can be any as disclosed herein and that include 1-300 (or any integer there between [e.g., 10, 15, 20, 25, 30, 35, 40, 45, or 50]) residues on the N-terminus and/or C-terminus. Such additional residues may be from a corresponding wild type sequence from which the glucosyltransferase enzyme is derived, or may be a heterologous sequence such as an epitope tag (at either N- or C-terminus) or a heterologous signal peptide (at N-terminus), for example. A glucosyltransferase enzyme herein typically lacks an N-terminal signal peptide.

A glucosyltransferase enzyme in certain embodiments does not occur in nature (i.e., non-native). For example, an enzyme herein is not believed to be one that is naturally secreted (i.e., mature form) from a microbe (from which the glucosyltransferase enzyme herein could possibly have been derived). A non-native enzyme in certain aspects comprises at least one, two, or three amino acid(s) modified/substituted as compared to its native counterpart. The amino acid sequence of a glucosyltransferase enzyme in certain aspects has been modified such that the enzyme produces more products (alpha-1,3-glucan and fructose), and less by-products (e.g., glucose, oligosaccharides such as leucrose), from a given amount of sucrose substrate. For example, one, two, three, or more amino acid residues of the catalytic domain of a glucosyltransferase herein can be modified/substituted to obtain an enzyme that produces more products (alpha-1, 3-glucan and fructose). Suitable examples of such a modified glucosyltransferase enzyme are disclosed in U.S. Pat. Appl. Publ. No. 2018/0072998, which is incorporated herein by reference.

A glucosyltransferase enzyme herein can be derived from any microbial source, such as a bacteria. Examples of bacterial glucosyltransferase enzymes are those derived from a *Streptococcus* species, *Leuconostoc* species or *Lactobacillus* species. Examples of *Streptococcus* species include *S. salivarius, S. sobrinus, S. dentirousetti, S. downei, S. mutans, S. oralis, S. gallolyticus* and *S. sanguinis*. Examples of *Leuconostoc* species include *L. mesenteroides, L. amelibiosum, L. argentinum, L. carnosum, L. citreum, L. cremoris, L. dextranicum* and *L. fructosum*. Examples of *Lactobacillus* species include *L. acidophilus, L. delbrueckii, L. helveticus, L. salivarius, L. casei, L. curvatus, L. plantarum, L. sakei, L. brevis, L. buchneri, L. fermentum* and *L. reuteri*.

A glucosyltransferase enzyme can produce alpha-1,3-glucan as disclosed herein. For example, a glucosyltransferase enzyme can produce alpha-1,3-glucan having at least 50% alpha-1,3 glycosidic linkages and a DPw of at least 100. The glucosyltransferase enzyme in certain embodiments does not have, or has very little (e.g., less than 1%), dextransucrase, reuteransucrase, or alternansucrase activity.

A glucosyltransferase enzyme herein can be prepared by fermentation of an appropriately engineered microbial strain, for example. Recombinant enzyme production by fermentation is well known in the art using microbial strains such as *E. coli, Bacillus* strains (e.g., *B. subtilis*), *Ralstonia eutropha, Pseudomonas fluorescens, Saccharomyces cerevisiae, Pichia pastoris, Hansenula polymorpha*, and species of *Aspergillus* (e.g., *A. awamori*) and *Trichoderma* (e.g., *T. reesei*) (e.g., see Adrio and Demain, Biomolecules 4:117-139, which is incorporated herein by reference). A nucleotide sequence encoding a glucosyltransferase enzyme amino acid sequence is typically linked to a heterologous promoter sequence to create an expression cassette for the enzyme. Such an expression cassette may be incorporated on a suitable plasmid or integrated into the microbial host chromosome, using methods well known in the art. The expression cassette may include a transcriptional terminator nucleotide sequence following the amino acid coding sequence. The expression cassette may also include, between the promoter sequence and amino acid coding sequence, a nucleotide sequence encoding a signal peptide that is designed to direct secretion of the glucosyltransferase enzyme. At the end of fermentation, cells may be ruptured accordingly and the glucosyltransferase enzyme can be isolated using methods such as precipitation, filtration, and/or concentration. Alternatively, a lysate comprising a glucosyltransferase can be used without further isolation. The activity of a glucosyltransferase enzyme can be confirmed by biochemical assay, such as measuring its conversion of sucrose to glucan polymer.

A glucosyltransferase enzyme herein can be primer-independent or primer-dependent. Primer-independent glucosyltransferase enzymes do not require the presence of a primer to perform glucan synthesis. A primer-dependent glucosyltransferase enzyme requires the presence of an initiating molecule in the reaction solution to act as a primer for the enzyme during glucan polymer synthesis. The term "primer" as used herein refers to any molecule that can act as the initiator for a glucosyltransferase enzyme. Primers that can be used in certain embodiments (in addition to added oligosaccharides as described herein, which are believed to serve as primers) include dextran. Dextran for use as a primer can be dextran T10 (i.e., dextran having a molecular weight of 10 kD), for example.

The activity of a glucosyltransferase enzyme herein can be determined using any method known in the art. For example, glucosyltransferase enzyme activity can be determined by measuring the production of reducing sugars (fructose and glucose) in a reaction solution containing sucrose (50 g/L), dextran T10 (1 mg/mL) and potassium phosphate buffer (pH 6.5, 50 mM), where the solution is held at 22-25° C. for 24-30 hours. The reducing sugars can be measured by adding 0.01 mL of the reaction solution to a mixture containing 1 N NaOH and 0.1% triphenyltetrazolium chloride and then monitoring the increase in absorbance at $OD_{480\ nm}$ for five minutes.

Insoluble alpha-1,3-glucan is produced in the methods/reactions of the present disclosure. Alpha-1,3-glucan in certain aspects has at least 50% alpha-1,3 glycosidic linkages and a DPw of at least 100.

Alpha-1,3-glucan herein typically comprises at least 50% alpha-1,3-glycosidic linkages. In certain embodiments, at least about 50%, 60%, 70%, 80%, 90%, 91%, 92%, 93%, 94%, 95%, 96%, 97%, 98%, 99%, 99.5%, or 100% (or any integer between 50% and 100%) of the constituent glycosidic linkages of an alpha-1,3-glucan are alpha-1,3 linkages. In some embodiments, accordingly, alpha-1,3-glucan has less than about 50%, 40%, 30%, 20%, 10%, 9%, 8%, 7%, 6%, 5%, 4%, 3%, 2%, 1%, 0.5%, or 0% (or any integer value between 0% and 50%) glycosidic linkages that are not alpha-1,3. Typically, the linkages that are not alpha-1,3 are mostly or entirely alpha-1,6. It should be understood that the higher the percentage of alpha-1,3 linkages present in alpha-1,3-glucan, the greater the probability that the alpha-1,3-glucan is linear, since there are lower occurrences of certain linkages forming branch points in the polymer. Thus, alpha-1,3-glucan with 100% alpha-1,3 linkages is believed to be completely linear. In certain embodiments, alpha-1,3-glucan has no branch points or less than about 5%, 4%, 3%, 2%, or 1% branch points as a percent of the glycosidic linkages in the polymer. Examples of branch points include alpha-1,6, ~1,2 and ~1,4 branch points.

Alpha-1,3-glucan herein can have a molecular weight in DPw or DPn of at least about 100 in some aspects. DPw or DPn in some embodiments can be at least about 100, 150, 200, 250, 300, 350, 400, 450, 500, 550, 600, 650, 700, 750, 800, 850, 900, 950, 1000, 1100, or 1200 (or any integer between 100 and 1200).

Alpha-1,3-glucan herein is insoluble in non-caustic aqueous systems, such as those conditions of a glucosyltransferase reaction herein (e.g., pH 4-8, see below). In general, the solubility of a glucan polymer in aqueous settings herein is related to its linkage profile, molecular weight, and/or degree of branching. For example, alpha-1,3-glucan with ≥95% 1,3 linkages is generally insoluble at a DPw of 8 and above in aqueous conditions at 20° C. In general, as molecular weight increases, the percentage of alpha-1,3 linkages required for alpha-1,3-glucan insolubility decreases.

In some other embodiments, an insoluble alpha-1,3-glucan can comprise at least about 30% alpha-1,3 linkages and a percentage of alpha-1,6 linkages that brings the total of both the alpha-1,3 and ~1,6 linkages in the alpha-1,3-glucan to 100%. For example, the percentage of alpha-1,3 and ~1,6 linkages can be about 30-40% and 60-70%, respectively. Glucosyltransferases for producing such alpha-1,3-glucan are disclosed in U.S. Pat. Appl. Publ. No. 2015/0232819, which is incorporated herein by reference. Alpha-1,3-glucan in these embodiments does not comprise alternan (alternating 1,3 and 1,6 linkages).

The disclosed method comprises, in step (b), contacting at least water, sucrose, a glucosyltransferase enzyme, and oligosaccharides (as provided in step [a]). This contacting step can optionally be characterized as providing a glucosyltransferase reaction composition comprising water, sucrose, a glucosyltransferase enzyme, and oligosaccharides. The contacting step of the disclosed method can be performed in any number of ways. For example, a desired amount of sucrose can first be dissolved or mixed in water, as well as the added oligosaccharides (optionally, other components can also be added at this stage of preparation, such as buffer components), followed by addition of a glucosyltransferase enzyme. The solution can be kept still, or agitated via stirring or orbital shaking, for example.

The temperature of a reaction composition herein can be controlled, if desired, and can be about 5-50° C., 20-40° C., 20-30° C., 20-25° C., for example. In some aspects, the temperature can be about 5-15° C. (e.g., ~8-12° C., ~9-11° C., ~10° C.), 15-25° C. (e.g., ~20° C.), or 25-35° C. (e.g., ~30° C.).

Oligosaccharides herein can be provided such that their initial concentration in a glucosyltransferase reaction set up in step (b) is at least about 1, 2, 3, 4, 5, 6, 7, 8, 9, 10, 15, 20, 25, 30, 5-10, or 5-15 g/L, for example. The foregoing concentrations can be provided using purified or unpurified (e.g., filtrate) oligosaccharide compositions. An "initial concentration" of oligosaccharides herein can, for example, refer to the oligosaccharide concentration in a glucosyltransferase reaction just after a minimum set of reaction components have been added/combined (at least water, sucrose, glucosyltransferase enzyme, optionally oligosaccharides). Oligosaccharides can be added to a glucosyltransferase reaction in batch or fed-batch mode. In batch mode, oligosaccharides are all added (are all present) at the beginning of, or within about 10-15 minutes of starting, a reaction, whereas oligosaccharides are added throughout a reaction in fed-batch mode. For example, a fed-batch can comprise adding oligosaccharides continuously or incrementally (e.g., dosing every 30 or 60 minutes) throughout, and/or during a period of (e.g., first 6 hours), a reaction. The total amount of oligosaccharides provided in a fed-batch mode reaction can be the same as the amount provided via any of the initial concentrations listed above. Oligosaccharides in some embodiments are added to a glucosyltransferase reaction either at its beginning or within 1-2 hours of its beginning.

The initial concentration of sucrose in a reaction composition herein can be about 20-400 g/L, 75-175 g/L, or 50-150 g/L, for example. In some aspects, the initial sucrose concentration is at least about 50, 75, 100, 150 or 200 g/L, or is about 50-600 g/L, 100-500 g/L, 50-100 g/L, 100-200 g/L, 150-450 g/L, 200-450 g/L, or 250-600 g/L. "Initial concentration of sucrose" refers to the sucrose concentration in a glucosyltransferase reaction composition just after all the reaction solution components have been added/combined (at least water, sucrose, glucosyltransferase enzyme, optionally added oligosaccharides).

Sucrose used in a glucosyltransferase reaction solution can be highly pure (≥99.5%) or be of any other purity or grade. For example, sucrose can have a purity of at least 99.0%, or can be reagent grade sucrose. As another example, incompletely refined sucrose can be used. Incompletely refined sucrose herein refers to sucrose that has not been processed to white refined sucrose. Thus, incompletely refined sucrose can be completely unrefined or partially refined. Examples of unrefined sucrose are "raw sucrose" ("raw sugar") and solutions thereof. Examples of partially refined sucrose have not gone through one, two, three, or more crystallization steps. Sucrose herein may be derived from any renewable sugar source such as sugar cane, sugar beets, cassava, sweet sorghum, or corn. Suitable forms of sucrose useful herein are crystalline form or non-crystalline form (e.g., syrup, cane juice, beet juice), for example. Additional suitable forms of incompletely refined sucrose are disclosed in U.S. Pat. Appl. Publ. No. 2015/0275256, which is incorporated herein by reference. The ICUMSA (International Commission for Uniform Methods of Sugar Analysis) of incompletely refined sucrose herein can be greater than 150, for example. Methods of determining ICUMSA values for sucrose are disclosed, for example, by the International Commission for Uniform Methods of Sugar Analysis in *ICUMSA Methods of Sugar Analysis: Official and Tentative Methods Recommended by the International Commission for Uniform Methods of Sugar Analysis (ICUMSA)* (Ed. H. C. S. de Whalley, Elsevier Pub. Co., 1964), which is incorporated herein by reference. ICUMSA can be measured in some aspects by ICUMSA Method GS1/3-7 as described by R. J. McCowage, R. M. Urquhart and M. L. Burge (*Determination of the Solution Colour of Raw Sugars, Brown Sugars and Coloured Syrups at pH 7.0—Official*, Verlag Dr Albert Bartens, 2011 revision), which is incorporated herein by reference.

The pH of a reaction composition in certain embodiments can be about 4.0-9.0, 4.0-8.5, 4.0-8.0, 5.0-8.0, 5.5-7.5, or 5.5-6.5. In some aspects, the pH can be about 4.0, 4.5, 5.0, 5.5, 6.0, 6.5, 7.0, 7.5, or 8.0. The pH can be adjusted or controlled by the addition or incorporation of a suitable buffer, including but not limited to: phosphate, tris, acetate, citrate, or any combination thereof. The buffer concentration in a reaction composition herein can be about 0.1-300 mM, 0.1-100 mM, 10-100 mM, 10 mM, 20 mM, or 50 mM, for example. A suitable amount of DTT (dithiothreitol, e.g., about 1.0 mM) can optionally be added to a reaction solution.

A glucosyltransferase reaction can be contained within any vessel (e.g., an inert vessel/container) suitable for applying one or more of the reaction conditions disclosed herein. An inert vessel in some aspects can be of stainless steel, plastic, or glass (or comprise two or more of these components) and be of a size suitable to contain a particular reaction. For example, the volume/capacity of an inert vessel (and/or the volume of a reaction composition herein), can be about, or at least about, 1, 10, 50, 100, 500, 1000, 2500, 5000, 10000, 12500, 15000, or 20000 liters An inert vessel can optionally be equipped with a stirring device.

A reaction composition herein can contain one, two, or more glucosyltransferase enzymes, for example. In some embodiments, only one or two glucosyltransferase enzymes is/are comprised in a reaction composition. A glucosyltransferase reaction herein can be, and typically is, cell-free (e.g., no whole cells present).

Completion of a reaction in certain embodiments can be determined visually (e.g., no more accumulation of insoluble glucan), and/or by measuring the amount of sucrose left in the solution (residual sucrose), where a percent sucrose consumption of at least about 90%, 95%, or 99% can indicate reaction completion. In some aspects, a reaction can be considered complete when its sucrose content is at or below about 5 g/L. A reaction of the disclosed process can be conducted for about 1 hour to about 2, 4, 6, 8, 10, 12, 14, 16, 18, 20, 22, 24, 36, 48, 60, 72, 96, 120, 144, or 168 hours, for example. A reaction can optionally be terminated and/or otherwise treated to stop glucosyltransferase activity by heating it to at least about 65° C. for at least about 30-60 minutes.

The yield of alpha-1,3-glucan produced in a glucosyltransferase reaction herein can be about, at least about, or up to about, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 55%, 60%, 65%, 70%, 75%, 80%, or 85%, for example, based on the weight or moles of sucrose converted in the reaction, or based on the glucosyl component of the reaction. Such a yield in some aspects is achieved in a reaction conducted for about 16-24 hours (e.g., ~20 hours), and/or is as measured using HPLC or NIR spectroscopy.

Alpha-1,3-glucan produced in a method in certain embodiments may optionally be isolated. In certain embodiments, isolating insoluble alpha-1,3-glucan can include at least conducting a step of centrifugation and/or filtration. Isolation can optionally further comprise washing alpha-1,3-glucan one, two, or more times with water or other aqueous liquid, and/or drying the alpha-glucan product.

An isolated alpha-1,3-glucan product herein, as provided in a dry form, can comprise no more than 2.0, 1.5, 1.0, 0.5, 0.25, 0.10, 0.05, or 0.01 wt % water, for example. In some aspects, an alpha-1,3-glucan product is provided in an amount of at least 1 gram (e.g., at least about 2.5, 5, 10, 25, 50, 100, 250, 500, 750, 1000, 2500, 5000, 7500, 10000, 25000, 50000, or 100000 g); such an amount can be a dry amount, for example.

Examples of conditions and/or components suitable for synthesizing insoluble alpha-1,3-glucan herein are disclosed in U.S. Pat. No. 7,000,000, and U.S. Pat. Appl. Publ. Nos. 2013/0244288, 2013/0244287, 2013/0196384, 2013/0157316, 2015/0275256, 2015/0240278, 2015/0240279, 2014/0087431, 2017/0002335 and 2018/0072998, all of which are incorporated herein by reference.

Any of the disclosed conditions for synthesizing insoluble alpha-1,3-glucan, such as the foregoing or those described in the below Examples, can be applied to practicing a reaction composition as presently disclosed (and vice versa).

The present disclosure also concerns a reaction composition for producing insoluble alpha-1,3-glucan. This reaction composition comprises at least water, sucrose, a glucosyltransferase enzyme that synthesizes insoluble alpha-1,3-glucan, and oligosaccharides. The oligosaccharides are added during preparation of the reaction composition and:

(i) comprise alpha-1,3 and alpha-1,6 glycosidic linkages, and/or (ii) are derived from a glucosyltransferase reaction. Insoluble alpha-1,3-glucan is produced in the reaction composition.

A reaction composition herein can be practiced following any of the presently disclosed embodiments or below Examples regarding methods of producing insoluble alpha-1,3-glucan, for example. Thus, any of features of such embodiments can characterize embodiments of a reaction composition herein.

In certain embodiments, the yield of alpha-1,3-glucan produced by a glucosyltransferase reaction can be increased compared to the yield of alpha-1,3-glucan that would be produced if step (b) is performed without added oligosaccharides (i.e., without the oligosaccharides of step [a]). For example, the yield of alpha-1,3-glucan produced can be increased by at least about 1%, 2%, 3%, 4%, 5%, 6%, 7%, 8%, 9%, 10%, 20%, 30%, 40%, 50%, 60%, 70%, 80%, 90%, 100%, 110%, or 120% compared to the yield of alpha-1,3-glucan that would be produced if step (b) lacked added oligosaccharides. It would be understood that percent increase of alpha-1,3-glucan product yield in a method herein can be measured, if desired, with respect to a suitable control glucosyltransferase reaction (e.g., a reaction having the same parameters as in step [b], except for the addition of oligosaccharides). In some aspects, an increase in yield characterizes a reaction comprising a glucosyltransferase that does not have any catalytic domain amino acid substitutions as compared to its corresponding native amino acid sequence.

The relative reaction rate of the glucosyltransferase reaction of step (b) in certain embodiments can be increased compared to the reaction rate that would be observed if step (b) was performed without the oligosaccharides provided in step (a). For example, the relative reaction rate of the glucosyltransferase reaction of step (b) can be at least about 1.025, 1.05, 1.075, 1.10, 1.15, 1.20, 1.25, 1.30, 1.40, 1.50, 1.60, 1.70, 1.80, 1.90, 2.00, or 2.10 with respect to the reaction rate of a suitable control glucosyltransferase reaction. To illustrate, if the relative reaction rate of a reaction herein is at least about 1.25 with respect to a control reaction, the reaction rate of this reaction is at least about 25% higher than the reaction rate of the control reaction. The reaction rate of a reaction can be expressed in terms of the change in concentration/amount of reactant(s) (e.g., sucrose) and/or the change in concentration/amount of product(s) (e.g., alpha-1,3-glucan) per unit time per unit concentration of active glucosyltransferase enzyme.

Reaction rates can be measured, for example, in grams alpha-1,3-glucan produced per liter per hour (g $L^{-1}$ $h^{-1}$).

By-product formation can optionally be reduced in the glucosyltransferase reaction of step (b) of a method herein of producing insoluble alpha-1,3-glucan, compared to the by-product formation that would be observed if step (b) was performed without the oligosaccharides provided in step (a). For example, the amount of glucose, leucrose, and/or gluco-oligosaccharide by-products formed in step (b) can be reduced compared to a suitable control glucosyltransferase reaction. Such reduction can be by at least about 5%, 10%, 15%, 20%, 25%, 30%, 40%, 50%, or 60%, for example.

In certain embodiments, the viscosity of alpha-1,3-glucan produced by a glucosyltransferase reaction can be decreased compared to the viscosity of alpha-1,3-glucan that would be produced if step (b) is performed without added oligosaccharides (i.e., without the oligosaccharides of step [a]). This viscosity can be determined for alpha-1,3-glucan as mixed or dissolved in a liquid. The viscosity of an alpha-1,3-glucan product herein can be at least about 5%, 10%, 15%, 20%, or 25% less, for example, than the viscosity of alpha-1,3-glucan that would be produced if step (b) lacked added oligosaccharides. It would be understood that percent decrease of alpha-1,3-glucan product viscosity in a method herein can be measured, if desired, with respect to a suitable control glucosyltransferase reaction (e.g., a reaction having the same parameters as in step [b], except for the addition of oligosaccharides).

The viscosity of alpha-1,3-glucan herein can be determined as mixed or dissolved in a liquid. In certain aspects, such a determination can be made with alpha-1,3-glucan as mixed in an aqueous liquid such as water or aqueous solution that is not caustic (e.g., a non-caustic aqueous liquid can have a pH of about 4-10, 5-9, 6-8, or 7); mixing is recommended since alpha-1,3-glucan herein is typically insoluble in such aqueous conditions. This mixing can be performed using any suitable means for effectively mixing alpha-1,3-glucan in a non-caustic aqueous liquid, such as homogenization or microfluidization (e.g., as disclosed in any of International Pat. Appl. Publ. No. WO2016/126685 or U.S. Pat. Appl. Publ. Nos. 2015/0167243, 2005/0249853 2003/0153746 and 2018/0021238, which are all incorporated herein by reference), for example. Mixing of alpha-1, 3-glucan in a non-caustic aqueous liquid can typically be done to prepare an aqueous slurry and/or dispersion (colloidal dispersion) of the glucan. The viscosity of such aqueous compositions can optionally be measured as slurry viscosity, in units of cP, at a shear rate of about 5-250 $s^{-1}$ (e.g., 7-200 $s^{-1}$), at a temperature of about 15-25° C. (e.g., ~20° C.), and/or with a 2-10 wt % (e.g., ~4-5 wt %) alpha-1,3-glucan aqueous mixture.

In certain aspects, a viscosity determination can be made with alpha-1,3-glucan as dissolved in a liquid. Such a liquid can be a caustic aqueous solution having a pH of at least about 11, for instance. A caustic aqueous solution can comprise at least a hydroxide (e.g., NaOH, KOH, tetraethyl ammonium hydroxide), and/or be as disclosed in International Pat. Appl. Publ. Nos. WO2015/200612 or WO2015/200590, or U.S. Pat. Appl. Publ. Nos. 2017/0208823 or 2017/0204203 (all of which are incorporated herein by reference), for example. In some aspects, a liquid for dissolving alpha-1,3-glucan herein for measuring viscosity can be non-aqueous such as one comprising an organic solvent (e.g., organic ionic liquid). Examples of a suitable organic solvent herein can comprise N,N-dimethylacetamide (DMAc) (optionally with about 0.5%-5% LiCl), dimethyl sulfoxide (DMSO), N,N-dimethylformamide (DMF), pyridine, $SO_2$/diethylamine (DEA)/DMSO, LiCl/1,3-dimethyl-2-imidazolidinone (DMI), DMSO/tetrabutyl-ammonium fluoride trihydrate (TBAF), N-methylpyrrolidone, and/or N-methylmorpholine-N-oxide (NMMO). In some aspects, alpha-1,3-glucan can be dissolved to a concentration of about 5-15 mg/mL (e.g., 10 mg/mL) in a suitable organic solvent such as DMAc/0.5% LiCl for measuring viscosity. The viscosity of dissolved alpha-1,3-glucan herein can be measured as intrinsic viscosity (IV, symbolized as "q", provided in units of mL/g) in some embodiments. IV measurements herein can be obtained, for example, using any suitable method such as disclosed in U.S. Pat. Appl. Publ. Nos. 2017/0002335 and 2017/0002336, Weaver et al. (*J. Appl. Polyn. Sci.* 35:1631-1637), or Chun and Park (*Macromol. Chem. Phys.* 195:701-711), which are all incorporated herein by reference.

The present disclosure also concerns a composition comprising insoluble alpha-1,3-glucan produced according to any method herein of producing insoluble alpha-1,3-glucan. In certain embodiments, such a composition can be either an aqueous composition or a non-aqueous composition. In some aspects, the viscosity of an insoluble alpha-1,3-glucan product herein is less than the viscosity of insoluble alpha-1,3-glucan (control glucan) that would have been produced if the oligosaccharides were not provided in the method/reaction. Viscosity can be measured with any methodology as described above with respect to alpha-1,3-glucan as mixed or dissolved in a liquid. The viscosity of the present alpha-1,3-glucan product can be at least about 5%, 10%, 15%, 20%, or 25% less than the viscosity of the control glucan, for example. The viscosity/DPw relationship of the present alpha-1,3-glucan product can be, for example, as disclosed in the below Examples showing that adding gluco-oligosaccharides to a glucosyltransferase reaction reduces viscosity.

Non-limiting examples of compositions and methods disclosed herein include:

1. A method for producing insoluble alpha-1,3-glucan comprising:
(a) providing oligosaccharides that:
 (i) comprise alpha-1,3 and alpha-1,6 glycosidic linkages, and/or
 (ii) are produced from a glucosyltransferase reaction;
(b) contacting at least water, sucrose, a glucosyltransferase enzyme that synthesizes insoluble alpha-1,3-glucan, and the oligosaccharides, wherein insoluble alpha-1,3-glucan is produced; and
(c) optionally, isolating the insoluble alpha-1,3-glucan produced in step (b).

23

2. The method of embodiment 1, wherein the oligosaccharides comprise about 60-99% alpha-1,3 and about 1-40% alpha-1,6 glycosidic linkages.

3. The method of embodiment 1 or 2, wherein the oligosaccharides have a degree of polymerization (DP) of 2 to 10.

4. The method of embodiment 1, 2, or 3, wherein the oligosaccharides are purified or unpurified.

5. The method of embodiment 4, wherein the oligosaccharides are produced from the glucosyltransferase reaction of (a)(ii).

6. The method of embodiment 5, wherein the glucosyltransferase reaction of (a)(ii) synthesizes insoluble alpha-1,3-glucan.

7. The method of embodiment 5 or 6, wherein the oligosaccharides are provided as a soluble fraction of the glucosyltransferase reaction of (a)(ii), and wherein the soluble fraction is processed or unprocessed.

8. The method of embodiment 7, wherein the soluble fraction is a portion of, or all of, a filtrate of the glucosyltransferase reaction of (a)(ii).

9. The method of embodiment 1, 2, 3, 4, 5, 6, 7, or 8, wherein the oligosaccharides are provided in step (b) at an initial concentration of at least about 1 g/L.

10. The method of embodiment 1, 2, 3, 4, 5, 6, 7, 8, or 9, wherein the yield of insoluble alpha-1,3-glucan produced is increased compared to the yield of insoluble alpha-1,3-glucan that would be produced if step (b) lacked the oligosaccharides.

11. The method of embodiment 1, 2, 3, 4, 5, 6, 7, 8, 9, or 10, wherein the viscosity of the insoluble alpha-1,3-glucan produced is decreased compared to the viscosity of insoluble alpha-1,3-glucan that would be produced if step (b) lacked the oligosaccharides, wherein viscosity is measured with alpha-1,3-glucan as mixed or dissolved in a liquid.

12. The method of embodiment 1, 2, 3, 4, 5, 6, 7, 8, 9, 10, or 11, wherein the insoluble alpha-1,3-glucan produced has at least 50% alpha-1,3 glycosidic linkages and a weight-average degree of polymerization (DPw) of at least 100.

13. The method of embodiment 1, 2, 3, 4, 5, 6, 7, 8, 9, 10, 11, or 13, wherein steps (a) and (b) are repeated one or more times, and wherein the oligosaccharides in each repeated step (a) are provided from the products (by-products) resulting from each immediately preceding step (b).

14. A reaction composition for producing insoluble alpha-1,3-glucan, the reaction composition comprising at least water, sucrose, a glucosyltransferase enzyme that synthesizes insoluble alpha-1,3-glucan, and oligosaccharides, wherein the oligosaccharides are added during preparation of the reaction composition and:

(i) comprise alpha-1,3 and alpha-1,6 glycosidic linkages, and/or (ii) are produced from a glucosyltransferase reaction, wherein insoluble alpha-1,3-glucan is produced in the reaction composition, optionally wherein the reaction composition is characterized by any feature of any one of embodiments 2-13.

15. A composition comprising insoluble alpha-1,3-glucan produced according to the method of any one of embodiments 1-13, or produced in the reaction composition of embodiment 14.

16. The composition of embodiment 15, wherein the viscosity of the insoluble alpha-1,3-glucan is less than the viscosity of insoluble alpha-1,3-glucan that would have been produced if the oligosaccharides are not provided in the method or reaction composition, wherein viscosity is measured with alpha-1,3-glucan as mixed or dissolved in a liquid.

EXAMPLES

The present disclosure is further exemplified in the following Examples. It should be understood that these Examples, while indicating certain preferred aspects herein, are given by way of illustration only. From the above discussion and these Examples, one skilled in the art can ascertain the essential characteristics of the disclosed embodiments, and without departing from the spirit and scope thereof, can make various changes and modifications to adapt the disclosed embodiments to various uses and conditions.

General Methods

All reagents were obtained from Sigma-Aldrich (St. Louis, Mo.) unless stated otherwise. Sucrose was obtained from VWR (Radnor, Pa.).

Preparation of Crude Extracts of Glucosyltransferase (GTF) Enzymes

The *Streptococcus salivarius* GTFJ enzyme (SEQ ID NO:2) used in certain of the following examples was expressed in *E. coli* strain DH10B using an isopropyl beta-D-1-thiogalactopyranoside (IPTG)-induced expression system. SEQ ID NO:2 has an N-terminal 42-residue deletion compared to the *S. salivarius* GTFJ amino acid sequence in GENBANK Identification No. 47527. Briefly, *E. coli* DH10B cells were transformed to express SEQ ID NO:2 from a DNA sequence (SEQ ID NO:1) codon-optimized for expression in *E. coli*. This DNA sequence was contained in the expression vector, pJexpress 404® (DNA 2.0, Menlo Park Calif.). The transformed cells were inoculated to an initial optical density (OD at 600 nm) of 0.025 in LB medium (10 g/L Tryptone; 5 g/L yeast extract, 10 g/L NaCl) and allowed to grow at 37° C. in an incubator while shaking at 250 rpm. The cultures were induced by addition of 1 mM IPTG when they reached an $OD_{600}$ of 0.8-1.0. Induced cultures were left on the shaker and harvested 3 hours post induction.

GTFJ enzyme (SEQ ID NO:2) was harvested by centrifuging cultured cells (25° C., 16,000 rpm) in an Eppendorf® centrifuge, re-suspending the cells in 5.0 mM phosphate buffer (pH 7.0) and cooling to 4° C. on ice. The cells were broken using a bead beater with 0.1-mm silica beads, and then centrifuged at 16,000 rpm at 4° C. to pellet the unbroken cells and cell debris. The crude extract (containing soluble GTFJ enzyme, SEQ ID NO:2) was separated from the pellet and analyzed by Bradford protein assay to determine protein concentration (mg/mL).

The GTF enzymes used in Example 5 were prepared as follows. *E. coli* TOP10® cells (Invitrogen, Carlsbad Calif.) were transformed with a pJexpress404®-based construct containing a particular GTF-encoding DNA sequence. Each sequence was codon-optimized to express the GTF enzyme in *E. coli*. Individual *E. coli* strains expressing a particular GTF enzyme were grown in LB medium with ampicillin (100 mg/mL) at 37° C. with shaking to $OD_{600}$=0.4-0.5, at which time IPTG was added to a final concentration of 0.5 mM. The cultures were incubated for 2-4 hours at 37° C. following IPTG induction. Cells were harvested by centrifugation at 5,000×g for 15 minutes and resuspended (20% w/v) in 50 mM phosphate buffer pH 7.0 supplemented with DTT (1.0 mM). Resuspended cells were passed through a French Pressure Cell (SLM Instruments, Rochester, N.Y.) twice to ensure >95% cell lysis. Lysed cells were centrifuged for 30 minutes at 12,000×g at 4° C. The resulting supernatant was analyzed by the BCA protein assay and SDS-PAGE to confirm expression of the GTF enzyme, and the supernatant was stored at ~20° C.

Analysis of Reaction Profiles

Periodic samples from reactions were taken and analyzed using an Agilent® 1260 HPLC equipped with a refractive index detector. An Aminex® HPX-87C column (BioRad, Hercules, Calif.) having deionized water at a flow rate of 0.6 mL/min and 85° C. was used to quantitate the level of sucrose, glucose, leucrose and fructose in the reaction mixtures. An Aminex® HPX-42A column (BioRad) having deionized water at a flow rate of 0.6 mL/min and 85° C. was used to quantitate soluble oligosaccharide by-products.

Analysis of Glucan Molecular Weight

Insoluble glucan polymer isolated from glucosyltransferase reactions was treated with N,N-dimethylacetamide (DMAc) with 5% lithium chloride (LiCl) at 100° C. for 16 hours to form a glucan polymer solution. This solution (100 µL) was then injected into an Alliance™ 2695 HPLC (Waters Corporation, Milford, Mass.) equipped with a differential refractometer detector operating at 50° C. The mobile phase (DMAc containing 0.11 wt % LiCl) passed at a flow rate of 0.5 mL/min through four styrene-divinyl benzene columns in series; specifically, one KD-802, one KD-801, and two linear KD-806M columns (Shodex, Japan). The molecular weight distribution of the glucan polymer sample was determined by comparison of retention time to a broad glucan standard.

Example 1

Glucan Polymerization Reactions Using GTFJ Enzyme (SEQ ID NO:2)

This example discloses information on the conversion of sucrose to insoluble alpha-1,3-glucan polymer and soluble sugars, and details how the raw material utilized in Example 2 was generated.

Sucrose (3000 g) was added to a clean 5-gallon polyethylene bucket. Water (18.1 L) and Fermasure™ (10 mL) were added to the bucket, and the pH was adjusted to 7.0 by addition of 5 vol % NaOH and 5 vol % $H_2SO_4$. The final volume was ~20 L and the initial concentration of sucrose as measured by HPLC was 152.5 g/L. The glucan polymerization reaction was initiated by adding 0.3 vol % of crude GTFJ enzyme (SEQ ID NO:2) extract prepared as described in the General Methods section. This extract contained about 2.9 mg/mL of protein. Agitation to the reaction solution was provided using an overhead mechanical motor equipped with a glass shaft and PTFE blade.

After 48 hours, HPLC analysis revealed that 96% of the sucrose had been consumed and the reaction was deemed to be complete. Insoluble alpha-1,3-glucan was removed by filtration, and the mother liquor (filtrate) was then concentrated using a rotary evaporator (bath temperature of 40-50° C.) to a total sugar concentration of 320 g/L sugars. The composition of the concentrated sugar solution is provided in Table 2.

Table 2 indicates that the concentrated filtrate obtained upon completion of the above glucan synthesis reaction contained saccharides in which about 14-15 wt % thereof were oligosaccharide (DP2-DP7) by-products. This concentrated filtrate was used in Example 2 for chromatographic isolation of oligosaccharides.

Example 2

Isolation and Analysis of Oligosaccharides Using Ion-Exchange Resins

This example discloses how oligosaccharides were isolated from a concentrated filtrate of a glucan synthesis reaction by chromatographic separation, and analyzed for glycosidic linkage profile. These isolated oligosaccharides were used in Examples 3, 5 and 7.

Chromatographic separation employing a strong acid cation-exchange resin was used to isolate the oligosaccharide fraction of the concentrated filtrate prepared in Example 1. The physical parameters of the column used for this separation appear in Table 3.

TABLE 3

| Physical Parameters of the Column Used for Chromatographic Separation | |
|---|---|
| Resin Type | FINEX CS11GC, #227 |
| Ion form | $Na^+$ |
| Crosslinking, % divinyl benzene | 5% |
| Particle size (mm) | 0.34 |
| Bed length (m) | 1.64 |
| Column diameter (m) | 0.093 |

The concentrated sugar solution (i.e., concentrated filtrate) prepared in Example 1 was filtered and diluted to 25 g dry solids/100 g solution using tap water. Prior to addition of the sugar solution to the column resin, the resin was washed with six bed volumes (BV) of sodium chloride solution (three BV at 10 wt % sodium chloride followed by three BV at 5 wt % sodium chloride) to convert the resin to the sodium form. The sugar solution (0.6 L) was then fed to the column, after which the column was eluted using water at a flow rate of 50 mL/min. The run conditions of the chromatographic separation are summarized in Table 4.

TABLE 4

| Chromatographic Separation Run Conditions | |
|---|---|
| Feed size (L) | 0.6 |
| Feed dry solids (g/100 g) | 25 |
| Column temp (° C.) | 65 |
| Flow rate (mL/min) | 50 |

TABLE 2

Composition of a Concentrated Filtrate of a Glucan Synthesis Reaction

| | Sucrose | Leucrose | Glucose | Fructose | DP2 | DP3 | DP4 | DP5 | DP6 | DP7 | Total |
|---|---|---|---|---|---|---|---|---|---|---|---|
| g/L | 13.5 | 130.6 | 25.5 | 103.8 | 18.3 | 14.1 | 8.2 | 3.6 | 1.5 | 0.9 | 320.1 |
| wt %[a] | 4.2 | 40.8 | 8 | 32.4 | 5.7 | 4.4 | 2.6 | 1.1 | 0.5 | 0.3 | 100 |

[a]Weight percentage is with respect to the measured saccharide components.

An oligosaccharide solution eluted between 11 and 21 minutes. A small amount of salts—indicated by an increase in conductivity—was eluted at the same time. The oligosaccharide fraction thus prepared was analyzed by HPLC to determine its product distribution. In total, the fraction contained >89% of oligosaccharides containing three or more hexose units and less than 1.5% of identifiable mono- and di-saccharides. This fraction was concentrated to a total dry weight of 317 g/L using a thin film evaporator (LCI Corporation, Charlotte, N.C.) followed by rotary evaporation with a ROTAVAPOR (R-151; Buchi, New Castle, Del.). The product distribution of the concentrated fraction as measured by HPLC appears in Table 5.

TABLE 5

Product Distribution of Concentrated Oligosaccharide Fraction

|   | Sucrose | Leucrose | Glucose | Fructose | DP2 | DP3 | DP4 | DP5 | DP6 | DP7 | Total |
|---|---------|----------|---------|----------|------|------|-------|------|------|------|-------|
| g/L | 0.0 | 2.5 | 0.0 | 0.7 | 31.5 | 75.9 | 101.8 | 62.1 | 26.9 | 15.3 | 316.7 |
| wt %[a] | 0.0 | 0.8 | 0.0 | 0.2 | 9.9 | 23.9 | 32.1 | 19.6 | 8.5 | 4.8 | 100 |

[a]Weight percentage is with respect to the measured saccharide components.

The concentrated oligosaccharide solution of Table 5 was analyzed using $^1$H NMR. NMR data were acquired on an Agilent® DD2 spectrometer operating at 500 MHz for $^1$H using a 5-mm cryogenic triple-resonance pulsed-field gradient (PFG) probe. Water suppression was obtained by carefully placing the observe transmitter frequency on resonance for the residual water signal in a "presat" experiment, and then using the first slice of a NOESY experiment with a full phase cycle (multiple of 32) and a mix time of 10 ms. One-dimensional $^1$H spectra were acquired with a spectral width of 6410 Hz, acquisition time of 5.1 s, 65536 data points, 4 s presaturation and a 90-degree pulse of 5.85 μs. Sample temperature was maintained at 25° C. Chemical shift assignments for different anomeric linkages were taken from Goffin et al. (2009, Bull Korean Chem. Soc. 30:2535-2541. Analysis of the spectra for this sample, which appears in FIG. 1, reveals that the oligosaccharides comprised about 78% alpha-1,3 and about 22% alpha-1,6 glycosidic linkages.

Thus, oligosaccharides from a concentrated filtrate of a glucan synthesis reaction were isolated and analyzed. The above concentrated oligosaccharide solution was used in Examples 3, 5 and 7.

Example 3

Comparison of Glucosyltransferase Reactions Lacking or Containing Added Oligosaccharides This example discloses that adding purified oligosaccharides (Example 2) containing a significant fraction of DP2+ material to alpha-1,3-glucan synthesis reactions results in increased insoluble alpha-1,3-glucan product yields compared to reactions lacking such added oligosaccharides. This example also demonstrates that this benefit (increased glucan product yield) is conferred across a wide variety of reaction conditions and oligosaccharide loadings.

Glucan synthesis reactions were prepared as follows. Sucrose (10 g), 0.27 g dihydrogen potassium phosphate ($KH_2PO_4$), 94 mL water, and 50 micro-L Fermasure™ were added to a 125-mL clean glass bottles equipped with a polypropylene cap. No oligosaccharides were added to the preparation in comparative Example 3A (Table 6). In Examples 3.1 and 3.2 (Table 6), certain amounts of the oligosaccharide solution prepared in Example 2 (Table 5) were added to each respective preparation; the amount of water added to each respective preparation was reduced by an equivalent volume. Each of the preparations contained a trace amount of glucose that came primarily from the sucrose component; no additional glucose was added to any of the preparations. Each preparation was agitated in an incubator shaker (temperature-controlled to 25° C.) until a solution formed, at which point the pH of each preparation was adjusted to 5.5 using 5 wt % aqueous sodium hydroxide or 5 wt % aqueous sulfuric acid. A sample of each preparation was taken for analysis by HPLC, after which 0.3 vol % of crude GTFJ enzyme (SEQ ID NO:2) extract prepared as described in the General Methods section was added to each preparation to initiate a polymerization reaction. Samples of each reaction were periodically taken and analyzed by HPLC as the reactions progressed. The initial rate of reaction was calculated by the amount of sucrose that was consumed in the first two hours of the polymerization. Once each reaction was deemed complete, insoluble polymer product was isolated from the reaction by filtration, washed with 200 mL water, washed with 100 mL acetone, and then dried.

Results for each reaction are shown in Table 6, which demonstrate that the yield of insoluble alpha-1,3-glucan polymer product is increased when oligosaccharides were added to the reaction (compare Examples 3.1 and 3.2 with Example 3A). The results also demonstrate that the yield of insoluble alpha-1,3-glucan obtained was further improved upon adding an additional amount of oligosaccharides (compare Example 3.2 with 3.1).

TABLE 6

Profiles of Glucosyltransferase Reactions Lacking or Containing Added Oligosaccharides

|   | Example | | |
|---|---|---|---|
|   | 3A | 3.1 | 3.2 |
| Nominal sucrose (g/L) | 100 | 100 | 100 |
| Actual sucrose (g/L) | 97.2 | 104.6 | 107.1 |
| Initial oligosaccharides, DP2+ (g/L) | 0.0 | 5.3 | 22.0 |
| Initial glucose (g/L) | 1.3 | 1.1 | 1.6 |
| Initial rate (g sucrose consumed/L-hr) | 5.3 | 14.1 | 12.3 |

TABLE 6-continued

Profiles of Glucosyltransferase Reactions Lacking
or Containing Added Oligosaccharides

| | Example | | |
|---|---|---|---|
| | 3A | 3.1 | 3.2 |
| % sucrose reacted | 94.3 | 96.4 | 98.1 |
| Yield polymer (g/L) | 15.4 | 24.6 | 27.5 |
| Yield glucose (g/L) | 8.1 | 5.9 | 4.9 |
| Yield oligomers (g/L) | 8.2 | 8.9 | 24.6 |
| Yield polymer (g/g sucrose reacted) | 0.17 | 0.24 | 0.26 |
| Yield glucose (g/g sucrose reacted) | 0.075 | 0.048 | 0.031 |
| Yield oligomer (g/g sucrose reacted) | 0.090 | 0.035 | 0.025 |

The benefits conferred upon adding oligosaccharides to an alpha-1,3-glucan synthesis reaction were obtained over a range of temperature and sucrose loadings. Reactions in Examples 3.3-3.5 were prepared and carried out in the same manner as described above, except that the initial sucrose concentration or temperature were modified. The results of these reactions, as well as those of the reactions of comparative Examples 3B, 3C and 3D (controls for Examples 3.3, 3.4 and 3.5, respectively) which did not have any added oligosaccharides, are summarized in Table 7.

TABLE 7

Profiles of Glucosyltransferase Reactions Lacking or Containing Added Oligosaccharides
Performed under Different Sucrose or Temperature Conditions

| Example | 3B | 3.3 | 3C | 3.4 | 3D | 3.5 |
|---|---|---|---|---|---|---|
| Nominal sucrose (g/L) | 50 | 50 | 150 | 150 | 100 | 100 |
| Actual sucrose (g/L) | 50.1 | 50.2 | 150.8 | 148.7 | 96.0 | 103.2 |
| Temperature (° C.) | 25 | 25 | 25 | 25 | 37 | 37 |
| Initial oligosaccharides, DP2+ (g/L) | 0.0 | 6.0 | 0.0 | 5.8 | 0.0 | 5.8 |
| Initial glucose (g/L) | 0.0 | 0.4 | 0.0 | 1.2 | 0.0 | 0.8 |
| % sucrose reacted | 96.9 | 99.5 | 95.8 | 97.6 | 97.0 | 97.2 |
| Yield polymer (g/L) | 9.5 | 14.2 | 23.0 | 33.4 | 21.7 | 27.5 |
| Yield polymer (g/g sucrose reacted) | 0.20 | 0.28 | 0.16 | 0.23 | 0.23 | 0.27 |

Thus, adding oligosaccharide by-products of an alpha-1,3-glucan synthesis reaction to a new alpha-1,3-glucan synthesis reaction can increase the yield of alpha-1,3-glucan produced by the new reaction and increase the rate of the polymerization while simultaneously decreasing the yield of unwanted oligomers and glucose. This reaction modulation occurs over a variety of conditions.

Example 4

Insoluble Alpha-1,3-Glucan Yields are Reduced in Glucosyltransferase Reactions in which Glucose is Added Instead of Oligosaccharides This example discloses that addition of glucose to a glucosyltransferase reaction, in an amount equivalent to the amount of oligosaccharides used in Example 3, is detrimental to the yield of insoluble alpha-1,3-glucan produced by the glucosyltransferase reaction.

Glucan synthesis reactions were prepared as follows. Sucrose (75 g) was weighed out and diluted to 0.75 L with deionized water in a 1-L unbaffled jacketed flask that was connected to a LAUDA RK20 recirculating chiller. Fermasure™ was then added (0.5 mL/L reaction), and the pH was adjusted to 5.5 using 5 wt % aqueous sodium hydroxide or 5 wt % aqueous sulfuric acid. In comparative Example 4A (Table 8), the trace amount of glucose came primarily from the sucrose component; no additional glucose was added to the preparation. In Example 4.1 (Table 8), glucose (18.8 g) was added to the preparation in addition to a trace amount of glucose present from the sucrose component. A polymerization reaction was initiated in each preparation by adding 0.3 vol % of crude GTFJ enzyme (SEQ ID NO:2) extract.

Agitation to each reaction was provided using an overhead mechanical motor attached to a 4-blade PTFE blade, and the temperature was controlled at 25° C. After the reactions were determined to be complete by HPLC, insoluble polymer product of each reaction was isolated by filtration. The polymer product was then washed with water (1.5 L), then washed with acetone (0.5 L), and then dried under a vacuum oven. The mass of the dry alpha-1,3-glucan product was recorded.

Results for each reaction are shown in Table 8, demonstrating that the yield of insoluble alpha-1,3-glucan polymer obtained in a glucosyltransferase reaction is reduced when glucose is added to the reaction.

TABLE 8

Profiles of Glucosyltransferase Reactions Containing
Various Amounts of Glucose

| | Example | |
|---|---|---|
| | 4A | 4.1 |
| Initial sucrose (g/L) | 97 | 96.32 |
| Initial glucose (g/L) | 2.5 | 27.8 |
| % sucrose reacted | 96.3 | 92.4 |
| Yield polymer (g/L) | 17.4 | 13.6 |
| Yield polymer (g/g sucrose reacted) | 0.19 | 0.15 |

Thus, addition of glucose to a glucosyltransferase reaction is detrimental to the yield of insoluble alpha-1,3-glucan produced by the glucosyltransferase reaction. It is noteworthy that the amount of glucose in the reaction of Example 4.1 was equivalent to the amount of oligosaccharides added to certain reactions in Example 3. The negative result in Example 4.1 thus indicates that it is oligomeric nature of the oligosaccharides used in Example 3 that is required for the observed glucan polymer yield-enhancing effect (i.e., the monomeric component, glucose, of the oligosaccharides most likely needs to be oligomerized in order to enhance glucan product yield in a reaction).

Example 5

Insoluble Alpha-1,3-Glucan Yields in Reactions Containing Added Oligosaccharides and Different GTF Enzymes This example discloses that the glucan polymer yield-enhancing effect of adding purified oligosaccharides (from Example 2) to a glucosyltransferase reaction applies generally to reactions containing enzymes besides GTFJ that produce insoluble alpha-1,3-glucan.

The different types of GTF enzymes used in this example were GTF 0874 (SEQ ID NO:4), GTF 1724-T1 (SEQ ID NO:7) and GTFJ-T1 (SEQ ID NO:8). Each of these glucosyltransferases can synthesize, or is expected to be able to synthesize, insoluble alpha-1,3-glucan polymer with about 100% alpha-1,3 glycosidic linkages (e.g., refer to U.S. Patent Appl. Nos. 2014/0087431 and 2016/0002693, which are incorporated herein by reference).

Glucan synthesis reactions were prepared as follows. Sucrose (10 g), 0.27 g dihydrogen potassium phosphate ($KH_2PO_4$), and 94 mL water were added to a 125-mL clean glass bottle equipped with a polypropylene cap. No oligosaccharides were added to the preparations in comparative Examples 5A, 5B, and 5C (Table 9). In Examples 5.1, 5.2, and 5.3, certain amounts of the oligosaccharide solution prepared in Example 2 (Table 5) were added to each respective preparation; the amount of water added to each respective preparation was reduced by an equivalent volume. Each of the preparations contained a trace amount of glucose that came primarily from the sucrose component; no additional glucose was added to any of the preparations. Each preparation was agitated in an incubator shaker (temperature-controlled to ° C.) until a solution formed, at which point the pH was adjusted to 5.5 using 5 wt % aqueous sodium hydroxide or 5 wt % aqueous sulfuric acid. A sample of each preparation was taken for analysis by HPLC, after which 0.3 vol % of a crude GTF enzyme extract prepared as described in the General Methods section was added to each preparation to initiate a polymerization reaction. Samples of each reaction were periodically taken and analyzed by HPLC as the reactions progressed. Once each reaction was deemed complete, the insoluble polymer product was isolated from the reaction by filtration, washed with 200 mL water, washed with 100 mL acetone, and then dried.

Results for each reaction are shown in Table 9, which demonstrate that the yield of insoluble alpha-1,3-glucan polymer product is increased when oligosaccharides were added to the reaction. This yield enhancement occurred in reactions employing different types of glucosyltransferase enzymes. It is notable that the approximate respective catalytic domains of each of GTF 1724-T1 and GTF 0874 share roughly only 50% amino acid sequence identity with the approximate catalytic domain of GTFJ (refer to U.S. Patent Appl. No. 2017/0002335, which is incorporated herein by reference). Despite this significant difference in sequence identity, each enzyme exhibited the insoluble alpha-1,3-glucan product yield increase.

TABLE 9

Profiles of Reactions Containing Different Types of GTF Enzymes, and Lacking or Containing Added Oligosaccharides

| Example | 5A | 5.1 | 5B | 5.2 | 5C[a] | 5.3 |
|---|---|---|---|---|---|---|
| Enzyme | GTFJ-T1 | | GTF 1724-T1 | | GTF 0874 | |
| | (SEQ ID NO: 8) | | (SEQ ID NO: 7) | | (SEQ ID NO: 4) | |
| Initial sucrose (g/L) | 141.0 | 150.2 | 149.5 | 150.2 | 142.6 | 150.2 |
| Initial oligosaccharides, DP2+ (g/L) | 0 | 5.7 | 0 | 5.7 | 0 | 5.7 |
| Initial glucose, (g/L) | 1.8 | 0.8 | 0.6 | 0.8 | 4.1 | 0.8 |
| % sucrose reacted | 93.7 | 96.4 | 99.5 | 99.4 | 90.0 | 97.6 |
| Yield polymer (g/L) | 21.1 | 30.5 | 11.5 | 19.9 | 9.0 | 18.9 |
| Yield polymer (g/g sucrose reacted) | 0.16 | 0.21 | 0.08 | 0.13 | 0.07 | 0.13 |

[a]Comparative Example 5C was run at pH 7.0 instead of pH 5.5.

Thus, adding oligosaccharide by-products of an alpha-1,3-glucan synthesis reaction to a new alpha-1,3-glucan synthesis reaction can increase the yield of alpha-1,3-glucan produced by the new reaction. This yield increase occurs in reactions employing various types of glucosyltransferase enzymes.

Example 6

Insoluble Alpha-1,3-Glucan Yields in Reactions Containing Other Types of Added Oligosaccharides This example discloses that oligosaccharides likely must contain alpha-1,3 glucosidic linkages to enable the shift in selectivity of a glucosyltransferase reaction towards insoluble alpha-1,3-glucan polymer. Oligosaccharides different from those produced in Example 2 (Table 5) were added to glucosyltransferase reactions to determine whether they can affect alpha-1,3-glucan yield.

Maltodextrin (5.5, 15, or 18 dextrose equivalents; Sigma-Aldrich), which has 100% alpha-1,4 linkages and typically contains mostly oligosaccharides (~DP2-DP20), was used in alpha-1,3-glucan polymerization reactions without further purification. Dextran (Dextran T-10, average molecular weight of 10000 Daltons, Sigma Aldrich), which is a polysaccharide containing >95% alpha-1,6 linkages, and hydrolyzed dextran, were also used in polymerization reactions. Hydrolyzed dextran was prepared by heating a solution containing 15 g Dextran T-10 in 141 mL water to 90° C. at pH 1.0. The distribution of oligosaccharides in the hydrolyzed dextran preparation appears in Table 10.

TABLE 10

Composition of Hydrolyzed Dextran Preparation

| | Glucose | DP2 | DP3 | DP4 | DP5 | DP6 | DP7 | DP8-10 | DP10+ | Total |
|---|---|---|---|---|---|---|---|---|---|---|
| g/L | 3.8 | 13.2 | 14.3 | 11.7 | 10.2 | 16.6 | 7.7 | 26.2 | 10.2 | 113.9 |
| wt %[a] | 3.4 | 11.6 | 12.5 | 10.3 | 8.9 | 14.6 | 6.8 | 23.0 | 8.9 | 100.0 |

[a]Weight percentage is with respect to the measured sacchande components.

GTFJ reactions were conducted following the protocol described in Example 3, except that maltodextrin, dextran, or hydrolyzed dextran was used instead of the oligosaccharides produced in Example 2 (Table 5). Table 11 provides the results of these reactions. Yields of insoluble alpha-1,3-glucan polymer in reactions using hydrolyzed dextran (Examples 6.1 and 6.2) and maltodextrins of various dextrose equivalents (Examples 6.3-6.5) were not affected or only marginally affected by the addition of these different types of oligosaccharides (Table 11, compare Examples 6.1-6.5 with Example 6A).

TABLE 11

Profiles of Glucosyltransferase Reactions Containing Different Types of Added Oligosaccharides or Polysaccharides

| Example | 6A | 6.1 | 6.2 | 6.3 | 6.4 | 6.5 | 6.6 | 6.7 |
|---|---|---|---|---|---|---|---|---|
| Oligosaccharide or polysaccharide tested | — | Hydrolyzed dextran | Hydrolyzed dextran | Maltodextrin, DE[b] 18 | Maltodextrin, DE[b] 5.5 | Maltodextrin, DE[b] 15 | Dextran T-10 | Dextran T-10 |
| Initial sucrose (g/L) | 97.2 | 98.6 | 102.1 | 100.4 | 100.4 | 102.5 | 95.7 | 98.5 |
| Initial oligosaccharides (DP2+) or polysaccharides, (g/L) | 0.0 | 1.6 | 2.3 | 6.5 | 6.5 | 6.2 | 6.2 | 27.9 |
| Initial glucose, (g/L)[a] | 1.3 | 2.3 | 2.8 | 0.6 | 0.6 | 0.6 | 2.8 | 2.6 |
| % sucrose reacted | 94.3 | 95.7 | 85.3 | 96.6 | 96.4 | 86.3 | 95.8 | 91.7 |
| Yield polymer (g/L) | 15.4 | 15.9 | 14.2 | 17.5 | 17.4 | 10.8 | 21.8 | 23.7 |
| Yield polymer (g/g sucrose reacted) | 0.17 | 0.17 | 0.16 | 0.18 | 0.18 | 0.12 | 0.24 | 0.26 |

[a]Trace glucose that was present in the sucrose component of each reaction.
[b]DE, dextrose equivalent.

The results in Table 11 indicate that oligosaccharides containing predominantly alpha-1,6 linkages (hydrolyzed dextran, Examples 6.1 and 6.2) or alpha-1,4 linkages (maltodextrin, Examples 6.3-6.5), when added to glucosyltransferase reactions, do not significantly enhance the yield of insoluble alpha-1,3-glucan polymer. Also, it appears that in order for an alpha-1,6-linked saccharide molecule to increase glucan product yield, such a saccharide molecule must be in the form of a larger polysaccharide (~10000 Daltons), since Dextran T-10 (Examples 6.6-6.7) increased insoluble alpha-1,3-glucan product yield, whereas its oligosaccharide counterparts (Examples 6.1-6.2) did not.

Tables 6, 7 (Example 3), and 9 (Example 5) on the other hand indicate that oligosaccharides comprising alpha-1,3 and alpha-1,6 linkages are able to significantly increase insoluble alpha-1,3-glucan yield in glucosyltransferase reactions. Based on these data, and that oligosaccharides with only alpha-1,6 linkages did not significantly affect alpha-1,3-glucan product yield (Table 11), it appears that the alpha-1,3 linkage component of the oligosaccharides of Table 5 are required for enhancing insoluble alpha-1,3-glucan product yield.

Thus, oligosaccharides likely must contain at least some fraction of alpha-1,3 glycosidic linkages to enhance insoluble alpha-1,3-glucan yield in a glucosyltransferase reaction.

Example 7

Isolation and Recycle of Oligosaccharides in Alpha-1,3-Glucan Synthesis Reactions This example discloses that oligosaccharides generated from a glucan polymerization reaction can be used to obtain consistent glucan product yield increases over multiple cycles of running polymerization reactions.

A first glucan synthesis reaction was prepared as follows. Sucrose (75 g) was weighed out and diluted to 0.75 L with deionized water in a 1-L unbaffled jacketed flask that was connected to a LAUDA RK20 recirculating chiller. Fermasure™ was then added (0.5 mL/L reaction), and the pH was adjusted to 5.5 using 5 wt % aqueous sodium hydroxide or 5 wt % aqueous sulfuric acid. Purified oligosaccharides obtained from a glucan polymerization reaction (Table 5, Example 2) were added to the preparation to a total concentration of DP2+ of ~5 g/L. Agitation to the preparation was provided using an overhead mechanical motor attached to a four-blade PTFE blade, and the temperature was controlled at 25° C. A polymerization reaction was initiated by adding 0.3 vol % of crude GTFJ enzyme (SEQ ID NO:2) extract. After the reaction was determined to be complete by HPLC, insoluble polymer product was isolated by filtration. The polymer product was then washed with water (1.5 L), then washed with acetone (0.5 L), and then dried under a vacuum oven. The mass of dry alpha-1,3-glucan product was recorded.

The filtrate from the reaction was concentrated to ~30 wt % dry solids using a rotary evaporator. A 25-mL fraction of this filtrate was purified by column-chromatography using an ÄKTA EXPLORER system (General Electric, Fairfield, Conn.). The run conditions of the chromatographic purification are summarized in Table 12.

TABLE 12

| Chromatographic Purification Run Conditions | |
|---|---|
| Resin Type | BioRad BIO-GEL P-2 Gel |
| Particle size (micron) | 45-90 |
| Bed length (cm) | 100 |
| Column diameter (m) | 0.026 |
| Feed size (mL) | 25 |
| Approximate feed dry solids (g/100 g) | 30 |
| Column temp (° C.) | 50 |
| Flow rate (mL/min) | 50 |

The fractions isolated from the chromatography were collected in 10-mL portions and analyzed by HPLC. Fractions containing oligosaccharides were combined and concentrated by rotary evaporation at 40° C.

These purified oligosaccharides were then used as the oligosaccharide source in a new glucan synthesis reaction (Example 7.1, Table 13) following the protocol of the first reaction (above); about 5 g/L of oligosaccharides were provided to the reaction. After this reaction was complete, oligosaccharides (DP2+) were purified therefrom by the above protocol and employed in a subsequent reaction. This cycle of running glucan polymerization reactions comprising oligosaccharides (DP2+) purified from the immediate previous reaction was repeated an additional four times: oligosaccharides from the reaction of Example 7.1 were added to the reaction of Example 7.2, oligosaccharides from the reaction of Example 7.2 were added to the reaction of Example 7.3, oligosaccharides from the reaction of Example 7.3 were added to the reaction of Example 7.4, oligosaccharides from the reaction of Example 7.4 were added to the reaction of Example 7.5. Data from these experiments are summarized in Table 13, showing improved alpha-1,3-glucan yields over comparative Example 7A, which did not have any oligosaccharides added to the reaction.

TABLE 13

Profiles of Glucosyltransferase Reactions Using Oligosaccharides Recycled from Previous Reactions

| Example | 7A | 7.1 | 7.2 | 7.3 | 7.4 | 7.5 |
|---|---|---|---|---|---|---|
| Initial sucrose (g/L) | 141.5 | 152.8 | 152.0 | 152.4 | 154.0 | 150.4 |
| Initial oligosaccharides, DP2+ (g/L) | 0.0 | 5.4 | 6.7 | 8.7 | 6.7 | 7.0 |
| Initial glucose, (g/L) | 0.0 | 0.0 | 0.9 | 1.0 | 0.0 | 1.1 |
| % sucrose reacted | 99.2 | 99.1 | 89.1 | 96.8 | 91.0 | 92.5 |
| Yield polymer (g/L) | 23.4 | 27.6 | 29.2 | 29.1 | 26.8 | 33.0 |
| Yield polymer (g/g sucrose reacted) | 0.17 | 0.18 | 0.22 | 0.20 | 0.19 | 0.24 |

Thus, based on the results shown in Table 13, oligosaccharides (DP2+) generated from a glucan polymerization reaction can be used to obtain fairly consistent glucan product yield increases over multiple cycles of running polymerization reactions.

Example 8

Glucan Polymerization Reactions Using an Improved GTF Enzyme

This example discloses the oligosaccharide composition of filtrate produced in an alpha-1,3-glucan synthesis reaction catalyzed by an improved glucosyltransferase.

The amino acid sequence of an *S. salivarius* glucosyltransferase enzyme that produces alpha-1,3-glucan with about 100% alpha-1,3 linkages was modified in its catalytic domain such that the enzyme could produce more products (alpha-1,3-glucan and fructose), and less by-products (e.g., glucose, oligosaccharides such as leucrose and DP2-7 gluco-oligosaccharides), from sucrose substrate, as compared to the enzyme's unmodified counterpart (refer to U.S. Pat. Appl. Publ. No. 2018/0072998, which is incorporated herein by reference).

An alpha-1,3-glucan synthesis reaction using the improved glucosyltransferase was run in a 5000-gal stainless steel vessel comprising 94 g/L white crystalline sucrose dissolved in water. The pH of the reaction was maintained using 10 mM potassium phosphate as a buffer and adjusted to 5.5 using 2 N $H_2SO_4$. An antimicrobial, FermaSure® XL, was added at 100 ppmv to prevent contamination during the reaction. The reactor contained three pitched blade impellers set to 33 rpm and was controlled at 23° C. using cooled water flowing into the jacket of the reactor. The reaction was initiated by adding 30 pounds of the improved glucosyltransferase enzyme, and deemed complete after 14 hours at which time the sucrose concentration reached less than 2 g/L. At the end of the reaction, the glucosyltransferase enzyme was deactivated by heating the reaction contents to 65° C. for 30 minutes using an external heat exchanger.

The insoluble alpha-1,3-glucan polymer (i.e., insoluble fraction) produced in the reaction was separated from the soluble fraction using a filter press, thereby providing a filtrate. Table 14 provides the carbohydrate content (dwb) of the filtrate.

TABLE 14

Carbohydrate Composition of Filtrate (wt % - Dry Weight Basis)

| Fructose | Glucose | Leucrose | DP2[a] | DP3+ | Total |
|---|---|---|---|---|---|
| 68.8 | 7.6 | 13.1 | 3.5 | 7.0 | 100 |

[a]Includes, in addition to DP2 gluco-oligosaccharides, at least sucrose.

Chromatographic separation employing a strong acid cation-exchange resin was used to isolate the oligosaccharide fraction of the filtrate. The physical parameters of the column used for this separation are in Table 15.

TABLE 15

Physical Parameters of the Column Used for Chromatographic Separation

| Resin Type | FINEX CS11GC, #296 |
|---|---|
| Ion form | Na+ |

TABLE 15-continued

Physical Parameters of the Column Used for Chromatographic Separation

| Crosslinking, % divinyl benzene | 5.5% |
|---|---|
| Particle size (mm) | 0.35 |
| Bed length (m) | 5.2 |
| Column diameter (m) | 0.225 |

The filtrate was modified accordingly to 30 g dry solids/100 g solution using ion-exchanged tap water. Prior to addition of this modified filtrate to the column resin, the resin was washed with six bed volumes (BV) of sodium chloride solution (three BV at 10 wt % sodium chloride followed by three BV at 5 wt % sodium chloride) to convert the resin to the sodium form. The modified filtrate (15 L) was then fed to the column, after which the column was eluted using ion-exchanged water at a flow rate of 30 L/h and at a column temperature of 70° C.

An oligosaccharide solution eluted between 140 and 185 minutes and was recovered. The oligosaccharide fraction thus prepared was analyzed by HPLC to determine its product distribution. Briefly, the composition of the oligosaccharide fraction was measured using an Agilent 1260 HPLC equipped with a refractive index detector. Separation of the oligosaccharides was realized using a BioRad AMINEX HPX-42A column using water as an eluent at 85° C. and a flow rate of 0.6 mL/min. The compositional profile of the oligosaccharides is provided in Table 16.

TABLE 16

Composition of Oligosaccharides Recovered by Fractionation (wt % - Dry Weight Basis)

| DP2 | DP3 | DP4 | DP5 | DP6 | DP7+ |
|---|---|---|---|---|---|
| 11 | 23 | 28 | 21 | 12 | 5 |

The oligosaccharide fraction described in Table 16 was subjected to partially methylated alditol acetate (PMAA) analysis (following methodology in Pettolino et al., *Nature Protocols* 7:1590-1607) and analyzed by GC-MS. Briefly, the sample was treated with DMSO anion and iodomethane to methylate hydroxyl groups, and then hydrolyzed with trifluoroacetic acid. The hydroxyl groups resulting from the broken glycosidic linkages were then acetylated with acetic anhydride, and the resulting glucitols were analyzed by GC/MS. The oligosaccharides were found to have the distribution described in Table 17 (all linkages therein believed to be alpha). The dominant linkage was alpha-1,3. No terminal fructose was detected in this oligosaccharide fraction.

TABLE 17

Linkage Distribution of Oligosaccharides

| Linkage | Linkage % |
|---|---|
| 1→3 | 87.5 |
| 1→6 | 7.3 |
| 1→3,6 | 2.8 |
| 1→4 | 1.0 |
| 1→2,3 | 0.7 |
| 1→2 | 0.6 |
| 1→3,4 | 0.3 |

Thus, DP2+ oligosaccharides present in the filtrate from a glucan synthesis reaction employing an improved glucosyltransferase were characterized. Such oligosaccharides, or a filtrate comprising them, for example, can be used as a source of added oligosaccharides for performing a glucosyltransferase reaction as presently disclosed.

Example 9

Effect of Glucose, Leucrose, Fructose, or Gluco-Oligosaccharide Additives on Alpha-1,3-Glucan Synthesis Reactions This example discloses comparing the individual effects of various sugars or oligosaccharides on enzymatic reactions for synthesizing alpha-1,3-glucan. Consistent with the above data (e.g., Examples 3, 5, 7), this example shows that the addition of certain oligosaccharides to an alpha-1,3-glucan synthesis reaction can increase product yield. Further, the alpha-1,3-glucan product of this higher yield reaction had significantly reduced intrinsic viscosity.

A 100 g/L sucrose/10 mM $KH_2PO_4$ solution (500 mL, pH-adjusted to 5.5 with sodium hydroxide or sulfuric acid) was added to individual 500-mL resin kettles serviced with overhead agitation. The following material was then added: glucose to 10 g/L, leucrose to 10 g/L, purified gluco-oligosaccharides to 10 g/L (produced similarly as in Example 8), fructose to 5 g/L, fructose to 10 g/L, fructose to 15 g/L, or fructose to 30 g/L. One kettle did not receive any additional material and was set as the control. The temperature of each kettle was adjusted to 25° C. Each reaction was then initiated by adding an aliquot (610 piL) of the glucosyltransferase enzyme used in Example 8 and allowed to run for about 16 hours at 25° C. with moderate agitation. A sample from each reaction was then taken, centrifuged and liquid-analyzed by HPLC for sugar content. The insoluble alpha-1,3-glucan produced in each reaction was then filtered, washed with about 1 L of water, and dried for several days in a vacuum oven at 45° C. The reaction filtrates were discarded.

Greater than 99% of sucrose was converted in each reaction. Table 18 provides the alpha-1,3-glucan yield of each reaction on an HPLC basis (difference in glucosyl consumption) and dried solids weight basis. Both these yield measurements were fairly consistent with each other.

TABLE 18

Effect of Glucosyltransferase Reaction Additives on Alpha-1,3-Glucan Yield

| Reaction Additive | Alpha-1,3-Glucan Yield | |
|---|---|---|
| | HPLC basis | Dried Solids basis |
| Control (no additive) | 65% | 63% |
| Glucose (10 g/L) | 58% | 59% |
| Leucrose (10 g/L) | 63% | 63% |
| Gluco-Oligosaccharides (10 g/L) | 83% | 79% |
| Fructose (5 g/L) | 64% | 60% |
| Fructose (10 g/L) | 62% | 58% |
| Fructose (15 g/L) | 60% | 57% |
| Fructose (30 g/L) | 53% | 52% |

Table 18 shows that alpha-1,3-glucan yield is reduced with the addition of glucose (consistent with Example 4) or increasing amounts of fructose, the latter of which served to increase the yield of leucrose by-product (data not shown). While the addition of leucrose did not have an effect, the addition of gluco-oligosaccharides purified from a separate glucosyltransferase reaction increased the yield of alpha-1,3-glucan.

The molecular weight (DPw) and intrinsic viscosity (q, provided in mL/g) (abbreviated as "IV") of alpha-1,3-glucan produced in some of the above reactions were measured and are shown in Table 19. IV measurements in the present Examples were made according to U.S. Pat. Appl. Publ. No. 2017/0002335, which is incorporated herein by reference.

TABLE 19

Effect of Glucosyltransferase Reaction Additives on Alpha-1,3-Glucan Product IV and DPw

| Reaction Additive | IV (mL/g) | DPw |
|---|---|---|
| Control-1 (no additive)[a] | — | 780 |
| Control-2 (no additive)[b] | 162 | 747 |
| Glucose (10 g/L) | 157 | 713 |
| Leucrose (10 g/L) | 187 | 704 |
| Gluco-Oligosaccharides (10 g/L) | 129 | 630 |
| Fructose (30 g/L) | 161 | 628 |

[a]Same control reaction as described above (Table 18). IV was not measured for the alpha-1,3-glucan product of this reaction.
[b]A separate control reaction that was run in a similar manner to the Control-1 reaction.

Table 19 shows that the IV of alpha-1,3-glucan is significantly reduced with the addition of gluco-oligosaccharides purified from a separate glucosyltransferase reaction. Though the DPw of this alpha-1,3-glucan also decreased, it is not believed this change accounts for the decrease in IV, as other additives also reduced DPw, but did not significantly reduce IV. This is quite apparent with the fructose addition (30 g/L), for example, which effected virtually the same reduction in alpha-1,3-glucan DPw, but had no noticeable effect on IV.

Thus, adding gluco-oligosaccharide by-products of an alpha-1,3-glucan synthesis reaction to a new alpha-1,3-glucan synthesis reaction can both (i) increase the yield, and (ii) decrease the IV, of alpha-1,3-glucan produced by the new reaction.

Example 10

Comparison of Alpha-1,3-Glucan Produced in Glucosyltransferase Reactions Lacking or Containing Added Gluco-Oligosaccharides This example discloses that adding gluco-oligosaccharides generated from an alpha-1,3-glucan polymerization reaction can be used to obtain an alpha-1,3-glucan product with lower aqueous slurry viscosity and lower dissolved polymer solution viscosity than alpha-1,3-glucan produced with a reaction that otherwise does not have the added gluco-oligosaccharides.

Each of the reactions prepared in this example employed the glucosyltransferase used in Example 8.

A first alpha-1,3-glucan reaction without the addition of gluco-oligosaccharides was prepared in a 4-L jacketed glass reactor with overhead stirring and an external chiller/heater to maintain a constant temperature. The reaction media was prepared by adding 299 g of sucrose to 2412 g of water, after which 3.54 g of potassium phosphate and 130 ipL of Fermasure® were added; the solution pH was then adjusted to 5.5 using sodium hydroxide or sulfuric acid. The reactor was maintained at a constant temperature of 20° C. with constant stirring with three 45° pitched blade impellers stirring at 250 rpm. The reaction was initiated by addition of 0.1 vol % glucosyltransferase enzyme solution to the stirred solution. The reaction was completed when the sucrose was below 5 g/L, after which the entire reactor was heated above 65° C. for a minimum of 1 hour followed by cooling down to room temperature.

The alpha-1,3-glucan produced in the first reaction was filtered in a vacuum Buchner funnel with filter paper, and the filtrate (which contains gluco-oligosaccharides) was collected to be used in the subsequent reaction. The alpha-1,3-glucan cake was then washed and filtered with more than 8 L of water to separate the sugars from the alpha-1,3-glucan to provide a cake with greater than 10 wt % solids (percent solids was measured accordingly).

A second reaction was prepared in the same reactor vessel by adding 299 g of sucrose to 780 g of filtrate from the first reaction and 1632 g of water. Since the filtrate contained 1.03 g of potassium phosphate, 2.51 g of potassium phosphate was added to the second reaction. The solution was mixed and temperature controlled to 20° C. followed by the addition of 130 ipL of Fermasure® and 0.1 vol % glucosyltransferase enzyme solution. The heating and filtration steps from the first reaction were repeated for the second reaction.

A third reaction was set up that was a repeat of the second reaction, but using filtrate collected from the second reaction. Table 20 summarizes the components of each of the first-third reactions (Reactions 1-3, respectively).

TABLE 20

Saccharide Components of Reactions 1-3

| Component | Reaction 1 | Reaction 2 | Reaction 3 |
|---|---|---|---|
| Initial Sucrose (g/L) | 114 | 115 | 116 |
| Initial Leucrose (g/L) | 0.0 | 4.9 | 9.0 |
| Initial Glucose (g/L) | 0.5 | 2.0 | 1.4 |
| Initial Fructose (g/L) | 0.3 | 16.0 | 19.6 |
| Initial Gluco-Oligosaccharides (g/L) | 0.0 | 3.5 | 3.9 |

The aqueous slurry viscosity of the alpha-1,3-glucan products of each of the first, second and third reactions was measured by first adding glucan cake with enough water to make a 4 wt % aqueous mixture, and then homogenizing the mixture. The viscosity of each mixture was then measured on a rheometer at 20° C., ramping the shear rate from 7 s$^{-1}$ to 200 s$^{-1}$ and measuring viscosity in centipoise (cP). The measurements are shown in FIG. 2, which shows a decrease in aqueous slurry viscosity of the alpha-1,3-glucan products as successively made in the first through third reactions.

The molecular weight (DPw) and intrinsic viscosity (IV) of each of the alpha-1,3-glucan products of the first-third reactions were measured (Table 21, Reactions 1-3, respectively) following their dissolution to a concentration of 10 mg/mL in DMAc/0.5% LiCl.

TABLE 21

Molecular Weight and IV of the Alpha-1,3-Glucan Products of Reactions 1-3

| | Reaction 1 | Reaction 2 | Reaction 3 |
|---|---|---|---|
| DPw | 773 | 753 | 736 |
| IV (mL/g) | 292 | 262 | 248 |

Thus, consistent with the results of Example 9 above, adding gluco-oligosaccharide by-products of an alpha-1,3-glucan synthesis reaction to a new alpha-1,3-glucan synthesis reaction can decrease the viscosity of alpha-1,3-glucan (as measured in both aqueous slurry and dissolved polymer formats) produced by the new reaction.

Example 11

Comparison of Alpha-1,3-Glucan Polymers Produced in Glucosyltransferase Reactions in which Gluco-Oligosaccharides are Added in Batch or Fed-Batch Manner This example discloses that adding gluco-oligosaccharides generated from an alpha-1,3-glucan polymerization reaction can be used in further reactions in either batch or fed-batch mode. In particular, this example discloses that adding gluco-oligosaccharides over the course an alpha-1,3-glucan polymerization reaction (fed-batch addition) reduces the viscosity of the glucan polymer produced over the reaction time. However, the final alpha-1,3-glucan polymer produced at the end of the reaction has a higher viscosity than alpha-1,3-glucan polymer produced in a reaction where all the added gluco-oligosaccharides are provided in a batch at the beginning of the reaction (batch addition). The higher final intrinsic viscosity (IV) of the polymer product of the fed-batch mode reaction is likely due to the reaction's lower initial gluco-oligosaccharide concentration compared to that of the batch reaction.

Each of the reactions prepared in this example employed the glucosyltransferase used in Example 8. The gluco-oligosaccharides used in these reactions were provided in the form of a glucosyltransferase reaction filtrate as prepared in Example 10, for example.

A fed-batch reaction was prepared in a 4-L jacketed glass reactor with overhead stirring and an external chiller/heater to maintain a constant temperature. The reaction media was prepared by adding 260 g of sucrose to 1656 g of water, after which 2.51 g of potassium phosphate and 130 µL of Fermasure® were added; the solution pH was then adjusted to 5.5 using sodium hydroxide or sulfuric acid. The reactor was maintained at a constant temperature of 23° C. with constant stirring with three 45° pitched blade impellers at 200 rpm. The reaction was initiated by addition of 0.1 vol % glucosyltransferase enzyme solution to the stirred solution. Gluco-oligosaccharides were added at a rate of 78 mL/hr after the start of the reaction. Samples were removed from the reactor every hour for the first six hours; alpha-1,3-glucan product in each sample was separated from the liquid by filtration and then washed three times with water. The reaction was completed when the sucrose was below 5 g/L (~22 hours), after which the entire reactor was heated above 65° C. for a minimum of 1 hour followed by cooling to room temperature.

A batch reaction was prepared in the same reactor vessel with 260 g of sucrose mixed with 1656 g of water and 780 g of liquid containing gluco-oligosaccharides. The solution was mixed and temperature controlled to 20° C. followed by the addition of 130 µL of Fermasure® and 0.1 vol % glucosyltransferase enzyme solution. Samples were obtained and processed, and the reaction was terminated, in the same manner as done with the fed-batch reaction.

Table 22 shows the change in gluco-oligosaccharide concentration during the fed-batch and batch reactions, and confirms that the initial gluco-oligosaccharide concentration was higher initially in the batch reaction compared to the fed-batch reaction.

TABLE 22

Gluco-Oligosaccharide Concentrations during the
Fed-Batch and Batch Reactions

| Reaction Time (hr) | Gluco-Oligosaccharide Concentration (g/L) | |
| --- | --- | --- |
| | Fed-Batch Reaction | Batch Reaction |
| 0 | 0 | 4 |
| 1 | 2 | 5 |
| 2 | 4 | 5 |
| 3 | 5 | 6 |
| 4 | 7 | 7 |
| 5 | 8 | 8 |
| 6 | 9 | 9 |

The molecular weight (MW) and intrinsic viscosity (IV) of the respective alpha-1,3-glucan products of the fed-batch and batch reactions were measured (Tables 23 and 24) following their dissolution to a concentration of 10 mg/mL in DMAc/0.5% LiCl.

TABLE 23

Viscosity of the Alpha-1,3-Glucan Products of
Fed-Batch and Batch Reactions

| Reaction | Reaction Time (hr) | IV (mL/g) |
| --- | --- | --- |
| Fed-Batch | 1 | 331 |
| Fed-Batch | 2 | 284 |
| Fed-Batch | 3 | 256 |
| Fed-Batch | 4 | 212 |
| Fed-Batch | 5 | 222 |
| Fed-Batch | 6 | 225 |
| Fed-Batch | 22 | 205 |
| Batch | 22 | 174 |

Table 23 shows that there was a decrease in alpha-1,3-glucan polymer viscosity as a function of time for the fed-batch reaction. However, the fed-batch final alpha-1,3-glucan viscosity was higher than the batch final alpha-1,3-glucan viscosity (both measured at 22-hour timepoints, Table 23).

TABLE 24

Molecular Weight of the Alpha-1,3-Glucan Products of
Fed-Batch and Batch Reactions

| Reaction Time (hr) | DPw | |
| --- | --- | --- |
| | Fed-Batch | Batch |
| 1 | 1130 | 876 |
| 2 | 1021 | 849 |
| 3 | 955 | 816 |
| 4 | 905 | 783 |
| 5 | 848 | 771 |
| 6 | 831 | 746 |
| 22 | 753 | 682 |

Thus, consistent with the results of Examples 9-10 above, adding gluco-oligosaccharide by-products of an alpha-1,3-glucan synthesis reaction in either batch or fed-batch mode to a new alpha-1,3-glucan synthesis reaction can decrease the viscosity of alpha-1,3-glucan produced by the new reaction. It is noteworthy, though, that such addition in batch mode has a greater effect on reducing polymer viscosity.

Example 12

Comparison of Alpha-1,3-Glucan Polymers
Produced in Glucosyltransferase Reactions with
Added Gluco-Oligosaccharides at Varying
Temperatures This example discloses that adding gluco-oligosaccharides generated from an alpha-1,3-glucan polymerization reaction to other alpha-1,3-glucan polymerization reactions at varying temperatures reduces the viscosity of the glucan polymer products of the latter reactions. This change in viscosity was significantly higher at lower reaction temperatures.

Each of the reactions prepared in this example employed the glucosyltransferase used in Example 8. The gluco-oligosaccharides used in these reactions were provided in the form of a glucosyltransferase reaction filtrate as prepared in Example 10, for example.

Reactions were run in 500-mL jacketed glass reactor with overhead stirring and an external chiller/heater to maintain a constant temperature. The reaction media was prepared by adding 50 g of sucrose to 469 g of water, after which 0.68 g of potassium phosphate and 25 µL of Fermasure® were added; the solution pH was then adjusted to 5.5 using sodium hydroxide or sulfuric acid. The reactors were maintained at a constant temperature with constant stirring with three 45° pitched blade impellers at 200 rpm. Each reaction was initiated by addition of 0.1 vol % glucosyltransferase enzyme solution to the stirred solution. Each reaction was completed when the sucrose was below 5 g/L, after which the entire reactor was heated above 65° C. for a minimum of 1 hour followed by cooling to room temperature.

The reactions (1-9) were run with three temperatures and three concentrations of gluco-oligosaccharides. The gluco-oligosaccharide concentration was changed by addition of appropriate amounts of filtrate from a previous alpha-1,3-glucan polymerization. The liquid added to each reaction was an appropriate mixture of water and filtrate. Table 25 shows the reaction temperatures and initial gluco-oligosaccharide concentrations of reactions 1-9. Following completion of all the reactions, the alpha-1,3-glucan products were filtered and washed with more than 1 L of water to prepare glucan wet cakes with greater than 10 wt % solids. Each cake was dissolved to a concentration of 10 mg/mL in DMAc/0.5% LiCl, after which the molecular weight and intrinsic viscosity of the glucan polymer products were measured (Table 25).

TABLE 25

Molecular Weight and Viscosity of Alpha-1,3-Glucan Produced in
Reactions with Varying Temperature and Initial
Gluco-Oligosaccharide Concentrations

| Reaction | Reaction Temperature (° C.) | Initial Gluco-Oligosaccharide Concentration (g/L) | DPw | IV (mL/g) |
| --- | --- | --- | --- | --- |
| 1 | 10 | 0.65 | 985 | 325 |
| 2 | 10 | 3.03 | 923 | 264 |
| 3 | 10 | 5.08 | 795 | 228 |
| 4 | 20 | 0.91 | 896 | 221 |
| 5 | 20 | 3.41 | 804 | 196 |
| 6 | 20 | 5.13 | 753 | 176 |
| 7 | 30 | 0.51 | 515 | 138 |
| 8 | 30 | 2.67 | 469 | 128 |
| 9 | 30 | 4.54 | 432 | 119 |

Table 25 shows that alpha-1,3-glucan product viscosity is lower in reactions (held at the same temperature) with higher initial gluco-oligosaccharide concentrations, which is consistent with above results. It is evident that this viscosity change was more pronounced (percentage-wise) in reactions held at a lower temperature.

Example 13

Alpha-1,3-Glucan Polymer Produced in Glucosyltransferase Reactions with Delayed Addition of Gluco-Oligosaccharides This example discloses that adding gluco-oligosaccharides generated from an alpha-1,3-glucan polymerization reaction to another alpha-1,3-glucan polymerization reaction four hours after the latter reaction has commenced (initiated by addition of glucosyltransferase enzyme) produces glucan polymer with similar viscosity compared to alpha-1,3-glucan polymerization reactions with no added gluco-oligosaccharides.

The reaction prepared in this example employed the glucosyltransferase used in Example 8. The gluco-oligosaccharides used in this reaction were provided in the form of a glucosyltransferase reaction filtrate as prepared in Example 10, for example.

A reaction was prepared in a 500-mL jacketed glass reactor with overhead stirring and an external chiller/heater to maintain a constant temperature. The reaction media was prepared by adding 46 g of sucrose to 364 g of water, after which 0.44 g of potassium phosphate and 20 µL of Fermasure® were added; the solution pH was then adjusted to 5.5 using sodium hydroxide or sulfuric acid. The reactor was maintained at a constant temperature of 19° C. with constant stirring with three 45° pitched blade impellers at 150 rpm. The reaction was initiated by adding 0.1 vol % glucosyltransferase enzyme solution to the stirred solution. Four hours after reaction initiation, liquid containing 11.5 g of sucrose, 0.11 g potassium phosphate, and 100 g of liquid with gluco-oligosaccharides was added to the reaction. The reaction was completed when the sucrose was below 5 g/L, after which the entire reactor was heated above 65° C. for a minimum of 1 hour followed by cooling to room temperature.

Following completion of the reaction, the alpha-1,3-glucan product was filtered and washed with more than 1 L of water to prepare a glucan wet cake with greater than 10 wt % solids. The cake was dissolved to a concentration of 10 mg/mL in DMAc/0.5% LiCl, after which the molecular weight and intrinsic viscosity of the glucan polymer product were measured (Table 26).

TABLE 26

Molecular Weight and Viscosity of Alpha-1,3-Glucan Produced in a Reaction with Delayed Gluco-Oligosaccharide Addition

| Reaction Description | DPw | IV (mL/g) |
| --- | --- | --- |
| Delayed Gluco-Oligosaccharide Addition (this Example) | 830 | 219 |
| Modest Gluco-Oligosaccharide Addition (Example 12, Reaction 4) | 896 | 221 |
| Gluco-Oligosaccharide Addition at Reaction Beginning (Example 12, Reaction 6) | 753 | 176 |

It is apparent from Table 26 that adding gluco-oligosaccharides generated from an alpha-1,3-glucan polymerization reaction to another alpha-1,3-glucan polymerization reaction some time after the latter reaction has commenced produces glucan polymer with similar viscosity compared to alpha-1,3-glucan polymerization reactions with only a modest amount of added gluco-oligosaccharides.

What is claimed is:

1. A method for producing insoluble alpha-1,3-glucan comprising:
   (a) providing oligosaccharides produced from a glucosyltransferase reaction that produces insoluble alpha-1,3-glucan having at least 50% alpha-1,3 glycosidic linkages and a weight-average degree of polymerization (DPw) of at least 100; and
   (b) contacting at least water, sucrose, said oligosaccharides, and a glucosyltransferase enzyme that produces insoluble alpha-1,3-glucan having at least 50% alpha-1,3 glycosidic linkages and a DPw of at least 100, thereby producing said insoluble alpha-1,3-glucan;
   wherein:
   steps (a) and (b) are repeated one or more times;
   the oligosaccharides in each repeated step (a) comprise oligosaccharides that are provided from the products resulting from a preceding step (b);
   the glucosyltransferase of the glucosyltransferase reaction of step (a) comprises an amino acid sequence that is at least 90% identical to SEQ ID NO:2, 4, 6, 7, 8, or 9; and the glucosyltransferase of step (b) comprises an amino acid sequence that is at least 90% identical to SEQ ID NO:2, 4, 6, 7, 8, or 9.

2. The method of claim 1, wherein the oligosaccharides are purified.

3. The method of claim 1, wherein the oligosaccharides are unpurified.

4. The method of claim 1, wherein said glucosyltransferase reaction of step (a) produces insoluble alpha-1,3-glucan having at least 80% alpha-1,3 glycosidic linkages, and said glucosyltransferase of step (b) produces insoluble alpha-1,3-glucan having at least 80% alpha-1,3 glycosidic linkages.

5. The method of claim 1, wherein the oligosaccharides are provided as a soluble fraction of said glucosyltransferase reaction of step (a).

6. The method of claim 5, wherein the soluble fraction is a portion of, or all of, a filtrate of said glucosyltransferase reaction of step (a).

7. The method of claim 1, wherein said oligosaccharides are provided in step (b) at an initial concentration of at least about 1 g/L.

8. The method of claim 1, wherein the yield of said insoluble alpha-1,3-glucan produced is increased compared to the yield of insoluble alpha-1,3-glucan that would be produced if step (b) lacked said oligosaccharides.

9. The method of claim 1, wherein the viscosity of said insoluble alpha-1,3-glucan produced is decreased compared to the viscosity of insoluble alpha-1,3-glucan that would be produced if step (b) lacked said oligosaccharides, wherein viscosity is measured with alpha-1,3-glucan as mixed or dissolved in a liquid.

10. The method of claim 4, wherein the glucosyltransferase reaction of step (a) produces insoluble alpha-1,3-glucan having at least 90% alpha-1,3 glycosidic linkages, and said glucosyltransferase of step (b) produces insoluble alpha-1,3-glucan having at least 90% alpha-1,3 glycosidic linkages.

11. The method of claim 1, wherein the method further comprises isolating the insoluble alpha-1,3-glucan produced in step (b).

12. The method of claim 1, wherein the oligosaccharides in each repeated step (a) comprise oligosaccharides that are provided from the products resulting from each immediately preceding step (b).

13. The method of claim 1, wherein the glucosyltransferase of
   the glucosyltransferase reaction of step (a) comprises an amino acid sequence that is at least 95% identical to SEQ ID NO:2, 4, 6, 7, 8, or 9, and
   the glucosyltransferase of step (b) comprises an amino acid sequence that is at least 95% identical to SEQ ID NO:2, 4, 6, 7, 8, or 9.

14. The method of claim 13, wherein the glucosyltransferase of
   the glucosyltransferase reaction of step (a) comprises an amino acid sequence that is at least 96% identical to SEQ ID NO:2, 4, 6, 7, 8, or 9, and the glucosyltransferase of step (b) comprises an amino acid sequence that is at least 96% identical to SEQ ID NO:2, 4, 6, 7, 8, or 9.

15. The method of claim 14, wherein the glucosyltransferase of the glucosyltransferase reaction of step (a) comprises an amino acid sequence that is at least 97% identical to SEQ ID NO:2, 4, 6, 7, 8, or 9, and the glucosyltransferase of step (b) comprises an amino acid sequence that is at least 97% identical to SEQ ID NO:2, 4, 6, 7, 8, or 9.

16. The method of claim 15, wherein the glucosyltransferase of
the glucosyltransferase reaction of step (a) comprises an amino acid sequence that is at least 98% identical to SEQ ID NO:2, 4, 6, 7, 8, or 9, and
the glucosyltransferase of step (b) comprises an amino acid sequence that is at least 98% identical to SEQ ID NO:2, 4, 6, 7, 8, or 9.

17. The method of claim 16, wherein the glucosyltransferase of the glucosyltransferase reaction of step (a) comprises an amino acid sequence that is at least 99% identical to SEQ ID NO:2, 4, 6, 7, 8, or 9, and the glucosyltransferase of step (b) comprises an amino acid sequence that is at least 99% identical to SEQ ID NO:2, 4, 6, 7, 8, or 9.

18. The method of claim 10, wherein the glucosyltransferase reaction of step (a) produces insoluble alpha-1,3-glucan having at least 95% alpha-1,3 glycosidic linkages, and said glucosyltransferase of step (b) produces insoluble alpha-1,3-glucan having at least 95% alpha-1,3 glycosidic linkages.

* * * * *